(12) United States Patent
Huang

(10) Patent No.: US 11,468,194 B2
(45) Date of Patent: Oct. 11, 2022

(54) METHODS AND SYSTEMS FOR ANONYMIZING GENOME SEGMENTS AND SEQUENCES AND ASSOCIATED INFORMATION

(71) Applicant: Ethan Huang, Cupertino, CA (US)

(72) Inventor: Ethan Huang, Cupertino, CA (US)

( * ) Notice: Subject to any disclaimer, the term of this patent is extended or adjusted under 35 U.S.C. 154(b) by 161 days.

(21) Appl. No.: 16/889,794

(22) Filed: Jun. 1, 2020

(65) Prior Publication Data

US 2020/0364371 A1    Nov. 19, 2020

Related U.S. Application Data

(63) Continuation of application No. 15/526,159, filed on May 11, 2017, now Pat. No. 10,713,383.

(51) Int. Cl.
    G06F 21/62        (2013.01)
    G16B 50/30        (2019.01)
    G16B 50/00        (2019.01)

(52) U.S. Cl.
    CPC ......... *G06F 21/6254* (2013.01); *G16B 50/00* (2019.02); *G16B 50/30* (2019.02)

(58) Field of Classification Search
    None
    See application file for complete search history.

(56) References Cited

U.S. PATENT DOCUMENTS

| | | | |
|---|---|---|---|
| 10,713,383 B2 * | 7/2020 | Huang | G06F 21/6254 |
| 2003/0065156 A1 | 4/2003 | Williams | |
| 2005/0158767 A1 | 7/2005 | Haskell | |
| 2006/0057586 A1 * | 3/2006 | Sung | G16B 20/00 435/6.15 |
| 2008/0077604 A1 | 3/2008 | Bharara | |
| 2009/0117542 A1 | 5/2009 | Maybruck | |
| 2013/0085681 A1 * | 4/2013 | Deciu | G16B 20/10 702/19 |
| 2013/0325666 A1 | 12/2013 | Carrino | |

(Continued)

OTHER PUBLICATIONS

Kris Popendorf, Hachiya Tsuyoshi, Yasunori Osana, Yasubumi Sakakibara "Murasaki: A Fast, Parallelizable Algorithm to Find Anchors from Multiple Genomes", Sep. 2010, Plos One, vol. 5, Issue 9. (Year: 2010).*

*Primary Examiner* — Kaveh Abrishamkar
(74) *Attorney, Agent, or Firm* — Eric Kelly

(57) ABSTRACT

Various methods and systems for processing at least some of genome sequences and at least some of associated information, for an individual, may include one or more of: segmenting genome sequences for at least a purpose of anonymizing genome information; using anchor segments for a purpose of minimizing electronic storage space in storing of genetic sequence information; generating at least one linkage record; generating at least one anonymized linkage record; processing a request for genetic study results; processing genetic study results received; and/or generating personalized information of interest pertaining to the individual. A purpose of such processing may be to prevent, minimize, and/or mitigate against (1) identification of the individual from such genome sequence information and/or from associated information; and/or (2) using such genome sequence information and/or associated information as a basis for discriminating against the individual.

20 Claims, 39 Drawing Sheets

Specification includes a Sequence Listing.

(56) References Cited

U.S. PATENT DOCUMENTS

| | | | |
|---|---|---|---|
| 2014/0075183 A1* | 3/2014 | Wang | G16B 30/10 |
| | | | 713/150 |
| 2014/0200166 A1* | 7/2014 | Van Rooyen | G16B 30/10 |
| | | | 702/19 |
| 2014/0344195 A1* | 11/2014 | Drew | G06F 16/35 |
| | | | 706/12 |
| 2014/0371110 A1* | 12/2014 | Van Rooyen | G16B 50/30 |
| | | | 438/618 |
| 2015/0315645 A1 | 11/2015 | Gaasterland | |

* cited by examiner

| DNA Markers | | Allele Frequency | | | Genotype Frequency | |
|---|---|---|---|---|---|---|
| Locus | Alleles | Observed | Samples | Freq | Formula | Freq |
| TPOX | 8,8 | 189 | 1000 | p=.189 | $p^2$ | 0.036 |
| VWA | 15 | 127 | 1000 | p=.127 | 2pq | 0.033 |
|  | 16 | 131 | 1000 | q=.131 |  |  |
| D13S317 | 11,11 | 110 | 1000 | p=.11 | $p^2$ | 0.012 |
| D16S539 | 11,11 | 308 | 1000 | p=.308 | $p^2$ | 0.095 |
| D18S51 | 12 | 175 | 1000 | p=.175 | 2pq | 0.043 |
|  | 13 | 122 | 1000 | q=.122 |  | .000000058 |

302 → DNA Markers
304 → Allele Frequency
306 → Genotype Frequency
310, 320, 330

FIG. 3

```
                        SEQUENCE LISTING

<160> NUMBER OF SEQ ID NOS: 4

<210> SEQ ID NO 1
<211> LENGTH: 20
<212> TYPE: DNA
<213> ORGANISM: Homo sapiens

<400> SEQUENCE: 1
gatcctccat atacaacggt                                                20

<210> SEQ ID NO 2
<211> LENGTH: 50
<212> TYPE: DNA
<213> ORGANISM: Homo sapiens

<400> SEQUENCE: 2
gatcctctat atacaacggt atctccacct caggtttaga tctcaacaac              50

<210> SEQ ID NO 3
<211> LENGTH: 50
<212> TYPE: DNA
<213> ORGANISM: Homo sapiens

<400> SEQUENCE: 3
gatcctccat atacacgacg gtatccaccg actgtttaga tctcaacaac              50

<210> SEQ ID NO 4
<211> LENGTH: 20
<212> TYPE: DNA
<213> ORGANISM: Homo sapiens

<400> SEQUENCE: 4
agatagatag atagatagat                                                20
```

METHODS AND SYSTEMS FOR ANONYMIZING GENOME SEGMENTS AND SEQUENCES AND ASSOCIATED INFORMATION

PRIORITY NOTICE

The present patent application is a continuation of U.S. non-provisional patent application Ser. No. 15/526,159 filed on May 11, 2017, and claims priority to said U.S. non-provisional patent application under 35 U.S.C. § 120. The above-identified patent application is incorporated herein by reference in its entirety as if fully set forth below.

TECHNICAL FIELD OF THE INVENTION

The present invention generally relates to the area of genome sequences, and more particularly relates to methods and systems for anonymizing genome sequences, including portions thereof (e.g., segments) and associated information.

COPYRIGHT AND TRADEMARK NOTICE

A portion of the disclosure of this patent application may contain material that is subject to copyright protection. The owner has no objection to the facsimile reproduction by anyone of the patent document or the patent disclosure, as it appears in the Patent and Trademark Office patent file or records, but otherwise reserves all copyrights whatsoever.

Certain marks referenced herein may be common law or registered trademarks of third parties affiliated or unaffiliated with the applicant or the assignee. Use of these marks is by way of example and should not be construed as descriptive or to limit the scope of this invention to material associated only with such marks.

BACKGROUND OF THE INVENTION

The present (circa 2015) price of sequencing an individual's genome may have dropped dramatically. Such individual genome sequencing may open a new era of genome-wide association studies (GWAS) (as well as other less than full genome genetic studies) based on a plurality of such individual's sequenced genomes (or portions thereof), along with their associated information (e.g., medical records) stored in various databases. Such individual genome sequencing may open a new era of personalized medicine, in which preventive and/or therapeutic interventions for complex diseases may be tailored to individuals based on their specific and particular genetic information.

However, because of a wealth of information that may be learned from or that inherently associates with the individual's own sequenced genome, handling of such individual genome sequence information may carry inherent risks of certain abuses. For example, the individual's genome sequence information itself may act as a unique "fingerprint" allowing the individual to be identified from their own genome sequence information. Thus, the handling of the individual's genome sequence information may provide opportunities for privacy breaches and/or intrusion into the individual's privacy. Some countries and/or states, by law, mandate that such sensitive and identifying information be managed, stored, transmitted, disclosed, published, processed, handled, and the like in particular manners that mitigate against such privacy abuses. For example, in the United States, there is a federal law known as the Health Insurance Portability and Accountability Act (HIPAA). HIPAA may establish standards for privacy and security of health information, as well as, standards for electronic data interchange (EDI) of such health information. HIPAA may specify a list of 18 identifiers as Protected Health Information (PHI) that must be encrypted by law, and must be stored only in encrypted form, and transmitted only through secure means. Biometric identifiers may be included in this list of 18 identifiers. Commonly, biometric identifiers may comprise an individual's fingerprints. Biometric identifiers may also comprise an individual's DNA sequences. For example, an example of using the individual's DNA sequences to identify the individual may be depicted in the FIG. 2 and FIG. 3 figures as well as discussed in the disclosure discussing those figures. HIPAA has specified two different de-identification techniques to minimize re-identification of a given individual. In particular, a safe harbor method may require removal of all 18 identifiers so no actual knowledge, including possibly residual information, can identify an individual. Since the biometric identifier, one of the 18 identifiers, has to be removed, the safe harbor method is not suitable for genetic studies, such as, but not limited to, GWAS. On the other hand, an expert determination method may apply statistical, mathematical, and/or scientific principles such that treated health information may carry an appropriately very small risk to re-identify an individual. This may comprise various data cleansing and/or anonymizing methods to minimized re-identification of any given individual. One example may be of anonymizing a geographic location like an individual's address to retain only the state of the address before transmission of such address information to others. However, HIPAA does not provide for explicit nor specific instructions for anonymizing the biometric identifier. Note, other nations, states, and/or regions may have laws similar to HIPAA, that may require certain results must be achieved when dealing with biometric identifiers in order to protect individuals privacy and minimize the potential for genetic abuse and/or genetic discrimination.

There then is a need, by law, and from the individual's perspective, for methods and/or systems for one or more of: managing, storing, transmitting, disclosing, publishing, processing, handling, and/or the like of genome sequence information such that an ability to learn the individual's identify is minimized or mitigated against.

In another example, the individual's genome sequence information may provide a means to associate various predispositions and/or active phenotypes in that individual. And others (e.g., third parties, like employers, insurance carriers, educational institutions, and/or the like) may use such information to discriminate against the individual. For example, such discrimination could be in the employment context and/or in a context admission into various programs, schools, insurance coverage and/or the like. There then is a need to prevent, minimize, and/or mitigate against such discrimination.

U.S. Pat. No. 8,019,620 issued to Miller et al. teaches an integrated platform for privacy management of electronic medical records, encompassing the entire life cycle of privacy management. U.S. Pat. No. 8,326,849 issued to El Emam et al. teaches a method, system and computer memory for optimally de-identifying a dataset of medical records where a lattice of information may be determined to define the anonymization strategies. U.S. Pat. No. 7,823,207 issued to Evenhaim teaches a privacy preserving data-mining protocol for querying privacy-sensitive micro-data. However, these platforms, systems, methods, and/or protocols were not specifically designed to manage nor process genome sequences and associated information. These platforms, systems, methods, and/or protocols are very poorly equipped to manage and/or process genome sequences and associated information in a way to achieve the desired goals. With about 3 million base pairs per individual of their own genome, portions of which may be of varying degrees of uniqueness, very specific methods and/or systems must be used to achieve the desired goals of preventing, minimizing, and/or mitigating against identification of a given individual; and/or of preventing, minimizing, and/or mitigating against discrimination.

U.S. Pat. No. 8,589,437 issued to Khomenko et al. teaches a system for separating identifying data from personal data in which a set of mapping data is introduced to associate a first set of stored identifying data such as account data and a second set of stored personal data such as phenotype data and genotype data. U.S. Pat. No. 8,600,683 issued to George teaches methods and systems for obtaining, processing, and managing sequence data in which a unique identifier is used to store the original sequence in one database and the same unique identifier is used to index information for identifying the source of the sequence in another database. However, how to further separate and associate the genotype data has never been taught in these systems and methods.

There is a need in the art for methods and/or systems for processing genome sequence information and associated information in a manner that achieves the desired goals of preventing, minimizing, and/or mitigating against identification of a given individual; and/or of preventing, minimizing, and/or mitigating against discrimination. Accordingly, methods and/or system for anonymizing at least a portion of a given genome sequence and/or at least a portion of associated information are required.

It is to these ends that the present invention has been developed.

BRIEF SUMMARY OF THE INVENTION

To minimize the limitations in the prior art, and to minimize other limitations that will be apparent upon reading and understanding the present specification, the present invention describes various methods and systems for processing at least some of one or more genome sequences and at least some of associated information, for at least one individual. A purpose of such processing may be to prevent, minimize, and/or mitigate against identification of the at least one individual from the at least some of the one or more genome sequences and/or from associated information. For example, some such methods and/or systems may be compliant with HIPAA with respect to at least some biometric identifiers like genome sequence information. Another purpose of such processing may be to prevent, minimize, and/or mitigate against using the at least some of one or more genome sequences and/or associated information as a basis for discriminating against the individual. In some embodiments, such processing may comprise one or more of: (1) segmenting the at least some of one or more genome sequences for at least a purpose of anonymizing the at least some of one or more genome sequences; (2) using anchor segments for a purpose of minimizing storage space in storing of genetic sequence information; (3) generating at least one linkage record for accessing the at least some of one or more genome sequences and/or the at least some of associated information from storage, wherein the at least some of one or more genome sequences and/or the at least some of associated information may have been organized into various organizational units for storage in a manner that minimizes opportunity for identification and/or discrimination; (4) generating at least one anonymized linkage record, which may entail further processing (e.g., modifying and/or anonymizing) of at least some of the organizational units; (5) processing requests for genetic study results to be provided and providing those genetic study results in a manner that may not compromise anonymity; (6) processing genetic study results received; and/or (7) generating personalized information of interest pertaining to the individual pursuant to a request for such information.

It is an objective of the present invention to prevent, minimize, and/or mitigate against identification of the at least one individual from the at least some of the one or more genome sequences and/or from associated information.

It is another objective of the present invention to provide methods and/or systems which may be compliant with HIPAA with respect to at least some biometric identifiers such as, but not limited to, genome sequence information.

It is another objective of the present invention to prevent, minimize, and/or mitigate against using the at least some of one or more genome sequences and/or associated information as a basis for discriminating against the individual.

It is another objective of the present invention to provide methods and systems for processing the at least some of one or more genome sequences and the at least some of associated information, for the at least one individual.

It is another objective of the present invention to provide methods and systems for segmenting the at least some of one or more genome sequences for at least a purpose of anonymizing the at least some of one or more genome sequences.

It is another objective of the present invention to provide methods and systems for using anchor segments for the purpose of minimizing storage space in storing of genetic sequence information.

It is another objective of the present invention to provide methods and systems for generating the at least one linkage record for accessing the at least some of one or more genome sequences and/or the at least some of associated information from storage, wherein the at least some of one or more genome sequences and/or the at least some of associated information may have been organized into the various organizational units for storage in a manner that minimizes opportunity for identification and/or discrimination.

It is another objective of the present invention to provide methods and systems for generating the at least one anonymized linkage record, which may entail further processing (e.g., modifying and/or anonymizing) of the at least some of the organizational units.

It is another objective of the present invention to provide methods and systems for processing the requests for the genetic study results to be provided and providing those genetic study results in a manner that may not compromise anonymity.

It is another objective of the present invention to provide methods and systems for processing genetic study results received.

It is yet another objective of the present invention to provide methods and systems for generating personalized information of interest pertaining to the individual pursuant to a request for such information.

These and other advantages and features of the present invention are described herein with specificity so as to make the present invention understandable to one of ordinary skill in the art, both with respect to how to practice the present invention and how to make the present invention.

Note, the subject matter of the various embodiments, including both method and system embodiments, of the present invention are not abstract ideas under 35 USC § 101 as presently (circa 2015) understood by *Alice Corp. Pty. Ltd. v. CLS Bank Int'l et al.,* 134 S.Ct. 2347, No. 13-298 (2014) and its progeny. For example, US patent law presently understand mathematical algorithms in isolation executed on a generic computer, and some fundamental economic and conventional business practices are abstract ideas and thus not patent eligible subject matter under 35 USC § 101. See *DDR HOLDINGS, LLC v. Hotels.com, LP,* 773 F. 3d 1245 (Fed. Cir. 2014). In DDR asserted claims in a U.S. Pat. No. 7,818,399 patent were upheld as patent eligible subject matter under 35 USC § 101. Id. These DDR claims do not recite a mathematical algorithm, nor do they recite a fundamental economic nor longstanding commercial practice; however those claims do address a business challenge and involve both a computer and the internet. Id. But the DDR claims "stand apart because they do not merely recite the performance of some business practice known from the pre-Internet world along with the requirement to perform it on the Internet. Instead, the claimed solution is necessarily rooted in computer technology in order to overcome a problem specifically arising in the realm of computer networks." Id. Likewise, the subject matter herein, that of methods and systems for anonymizing genome sequences, segments, and associated information for purposes of protecting identity and minimizing discrimination also not do exclusively employ mathematical algorithms, nor claim fundamental economic nor longstanding commercial practices; and because of the sheer amount of information conveyed in such sequences of nucleotides, including how such sequence information gets transcribed, translated and regulated to produce various phenotypes, similarly requires computers and/or computer systems to function. And the problems of compromised identity and/or of being discriminated against because of one's genome is a new problem that is only now manifesting as genetic studies mature and come to fruition, at least with respect to mapping, such as the Human Genome Project. Furthermore, such anonymization methods and systems must balance the desired purposes of identity protection and minimizing likelihood of discrimination with genetic researchers and medical community needs that prefer genetic data to be non-anonymized, as anonymization may result in some loss of information.

For example, at least some of the present subject matter may be drawn to processing (via one or more computer systems) genetic information, such as nucleotide sequence information, as well as a multitude of sequence-associated-information and associated information of that genetic information; wherein at least some of such processing may be directed to receiving, modifying, anonymizing, providing, and non-transitory storage of such genetic information, and its nucleotide sequence information, sequence-associated-information, and associated information. This processing, at least in part, may be specifically aimed at protecting an individual's anonymity and/or minimizing discrimination against that individuals from abuses related to interacting with that individual's genetic information (and associated information). Such genetic information and particularly such processing are not abstract under 35 USC § 101 and its interpretive cases, because for one, there is no long human history of dealing with such genetic information and its processing. For example, DNA (deoxyribonucleic acid) was only discovered as a molecule in about 1869. However, it was not until 1943 that DNA was demonstrated as capable of coding for inheritance information. And then it was not until 1953 that Watson and Crick were credited with determining the double helix structure of some DNA. Then it was not until the mid-1970s that Sanger developed techniques to sequence DNA. Advancements in nucleotide sequencing technology are still presently an active area of commercial as well as academic research and development. In 2001, the Human Genome Project announced that about 90 percent of the three billion human base-pairs had been sequenced. However, presently, variations (e.g., polymorphisms) in the human genome are continually being uncovered. And presently we do not fully understand significances of the entire human genome including its variations; particularly with respect to identifying predispositions (including both desirable and undesirable [e.g., genetic diseases]), safely preventing undesirable predispositions from manifesting, safely correcting undesirable manifestations once they occur, and/or safely achieving desired phenotypes through intentional and direct genetic manipulation. These are all presently active areas of genetic research. However, we are beginning to learn and understand that genetic information may pose a threat the individual's privacy and/or provide information that others might use as a basis for discriminating against the individual, which is where the present need for various embodiments of the present invention arise from. Secondly, because of the sheer volume of data involved, even for a single individual's own genome and its nucleotide sequence information, sequence-associated-information, and associated information, necessarily requires that processing of such data must utilize various computer systems as disclosed herein.

BRIEF DESCRIPTION OF THE SEVERAL VIEWS OF THE DRAWINGS

Elements in the figures have not necessarily been drawn to scale in order to enhance their clarity and improve understanding of these various elements and embodiments of the invention. Furthermore, elements that are known to be common and well understood to those in the industry are not depicted in order to provide a clear view of the various embodiments of the invention.

FIG. 3 may depict a follow-on example from FIG. 2, wherein allele frequency for a subset of the set of loci may be used to calculate a final genotype frequency.

Figure 4A:
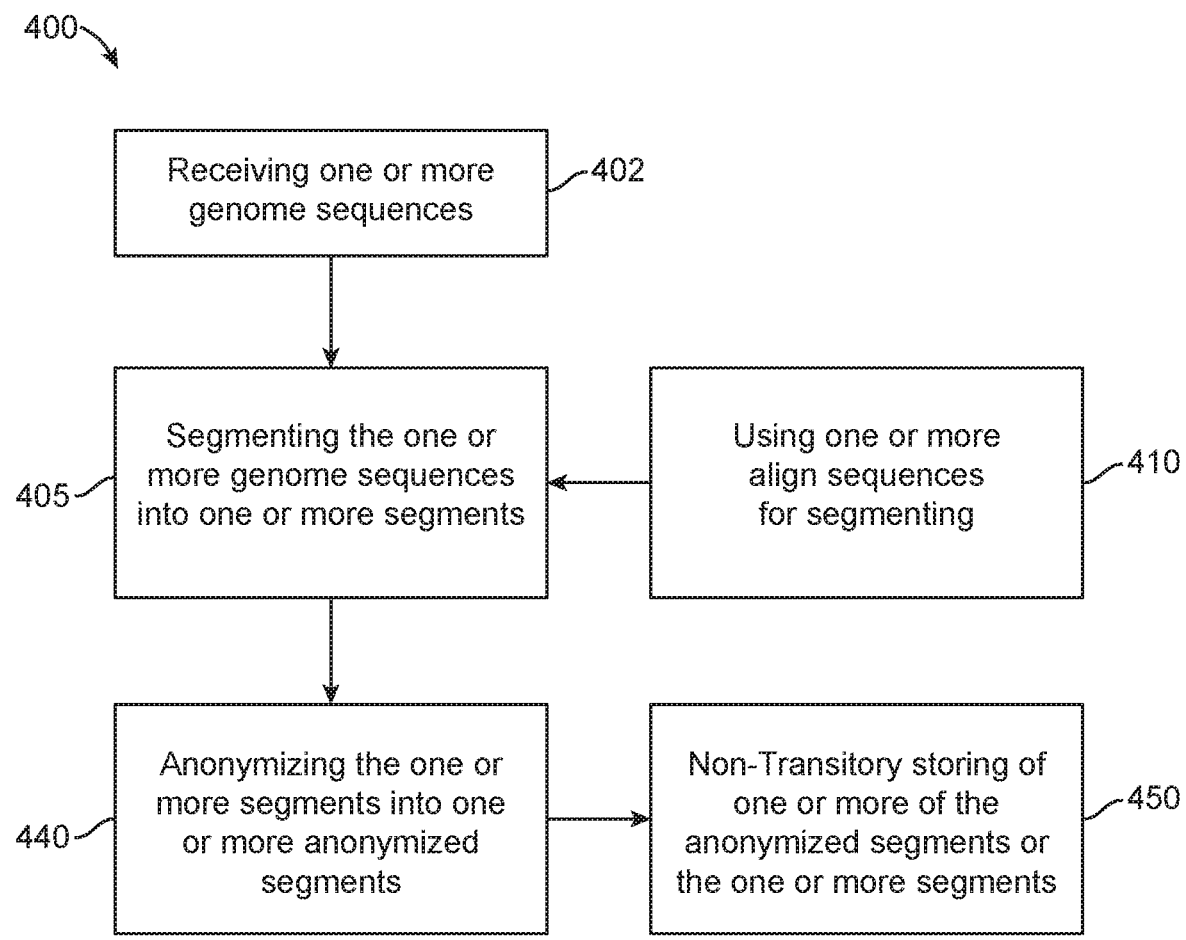
Figure 4B:
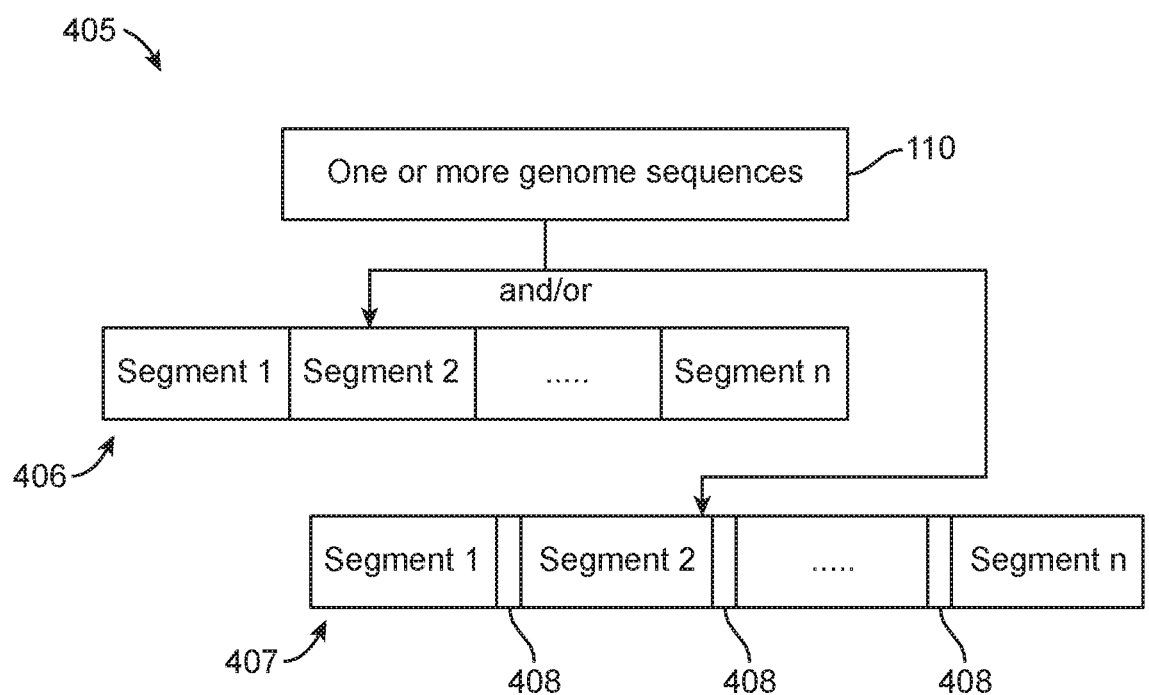
Figure 4C:
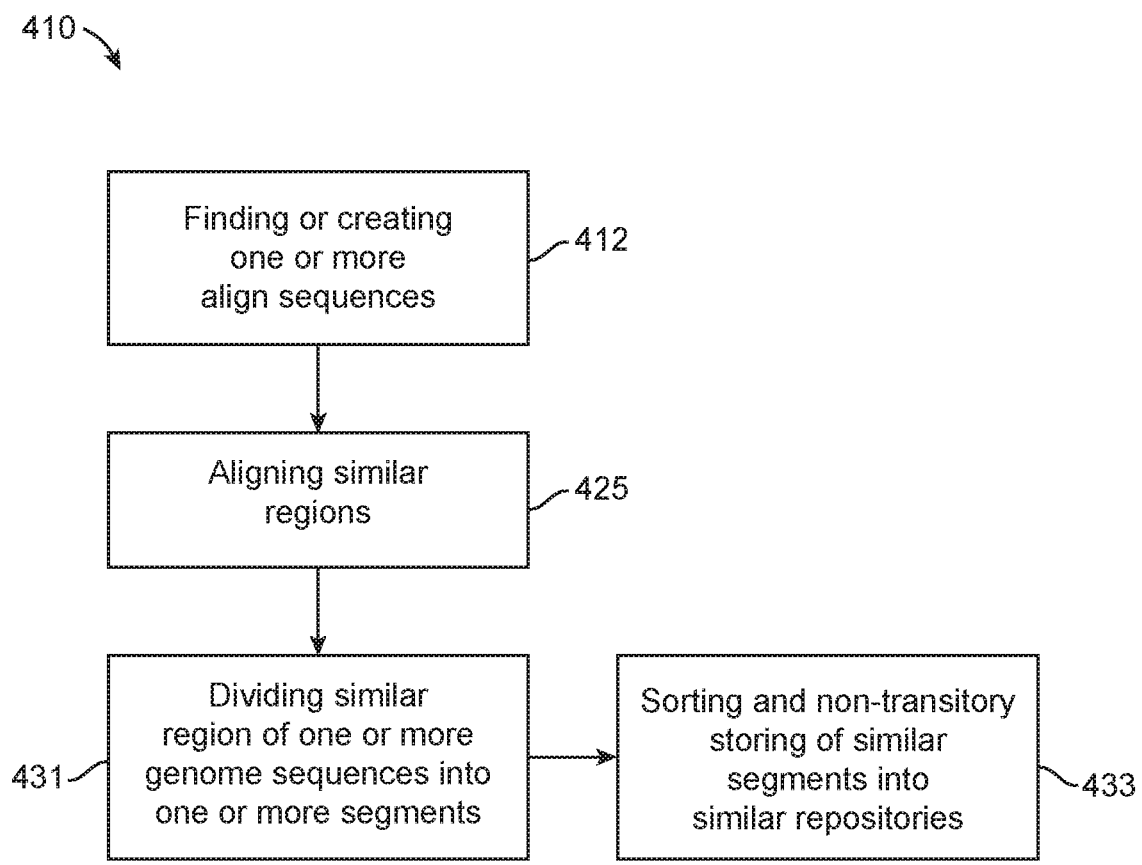
Figure 4D:
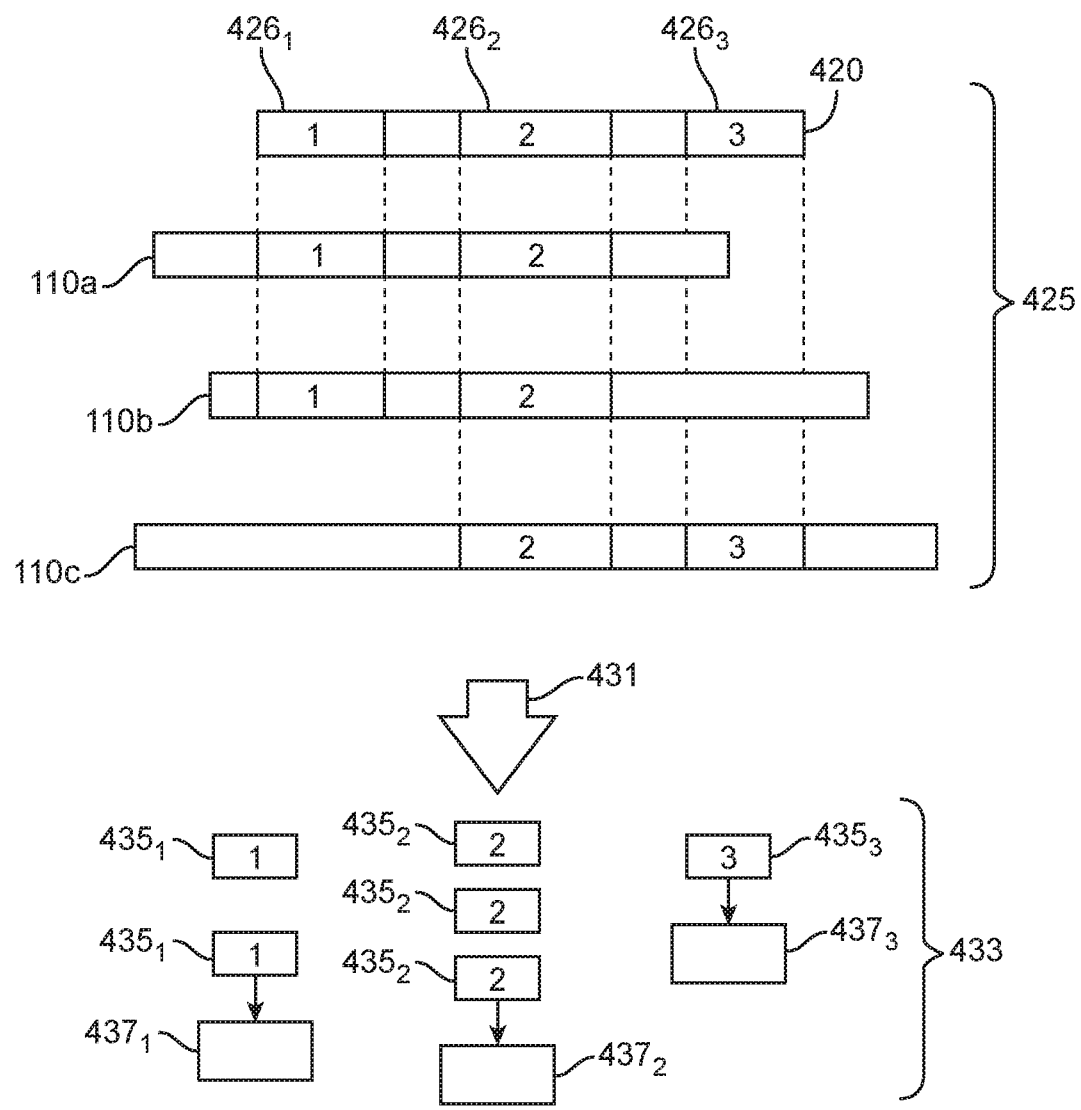
Figure 4E:
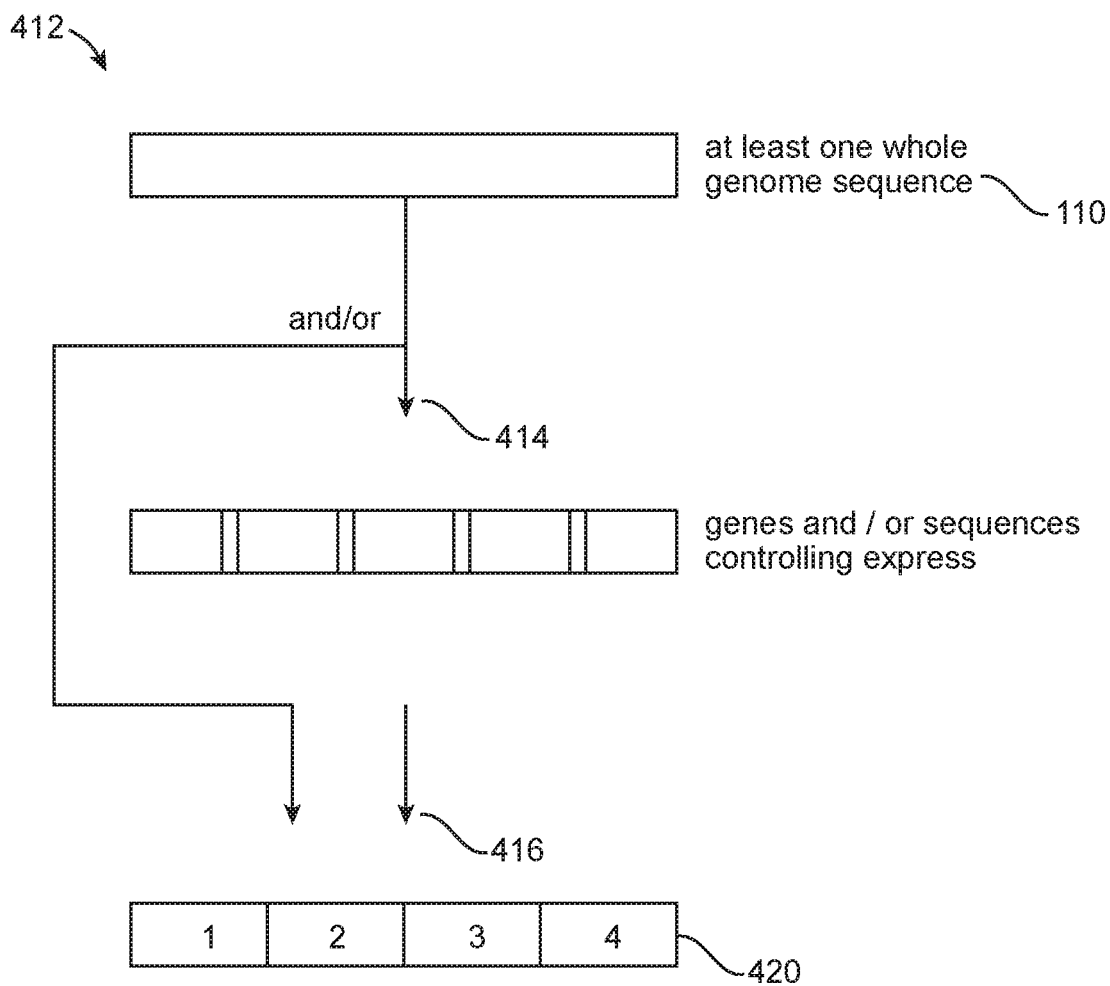

A FIG. 4 series of figures may comprise FIG. 4A through and including FIG. 4E. These FIG. 4 series of figures may address a process of segmenting one or more genome sequences into one or more segments.

FIG. 4A may depict a flow diagram of exemplary steps for the process of segmenting the one or more genome sequences into the one or more segments.

FIG. 4B may depict a representation of the process of segmenting the one or more genome sequences into the one or more segments.

FIG. 4C may depict a flow diagram of exemplary steps for a process of using one or more align sequences to aid in the segmenting process.

FIG. 4D may depict a representation of segmenting at least three genome sequences, using align sequences, and how resulting like segments may be grouped together and non-transitorily stored in like grouped repositories.

FIG. 4E may depict a schematic for finding and/or creating the one or more align sequences from a genome sequence.

Figure 5A:
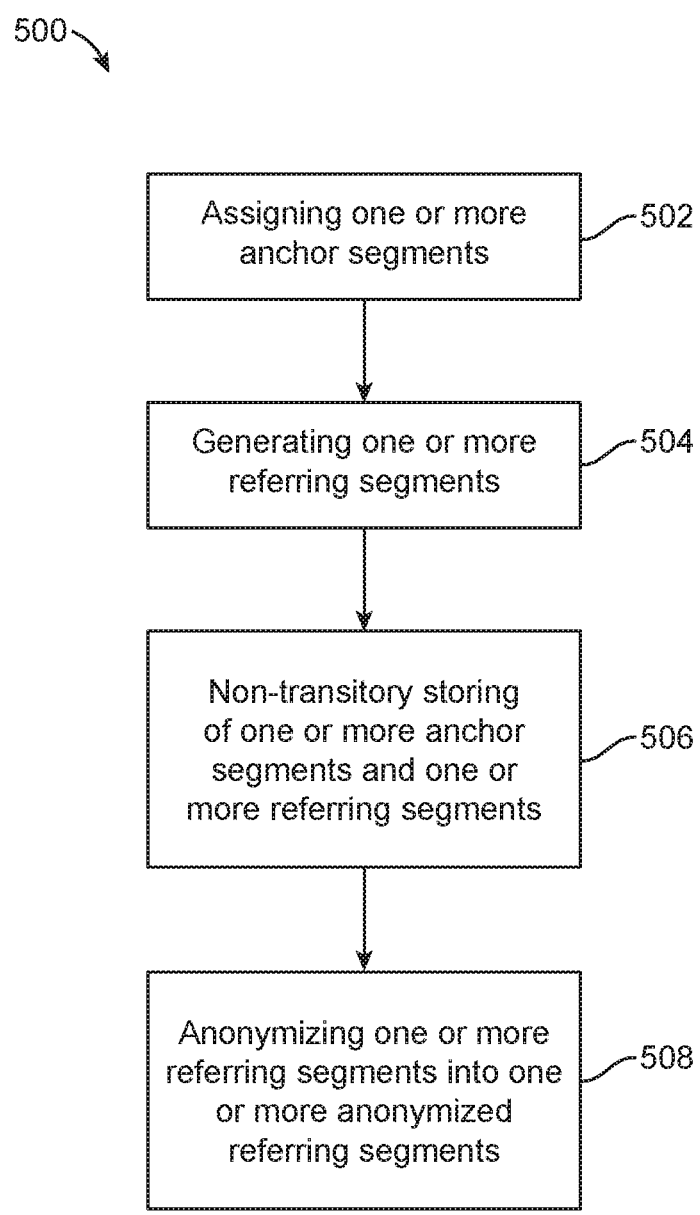
Figure 5B:
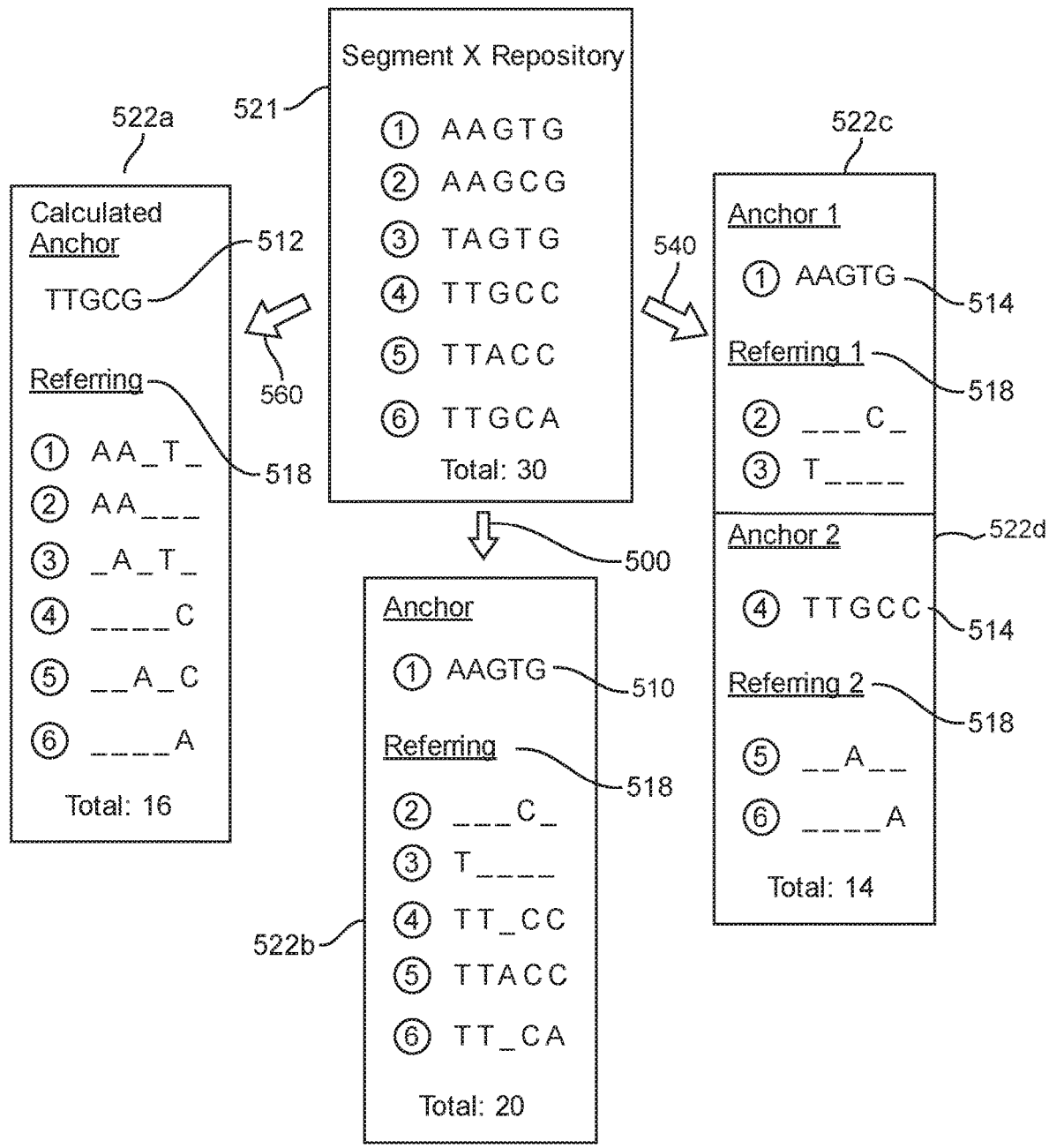
Figure 5C:
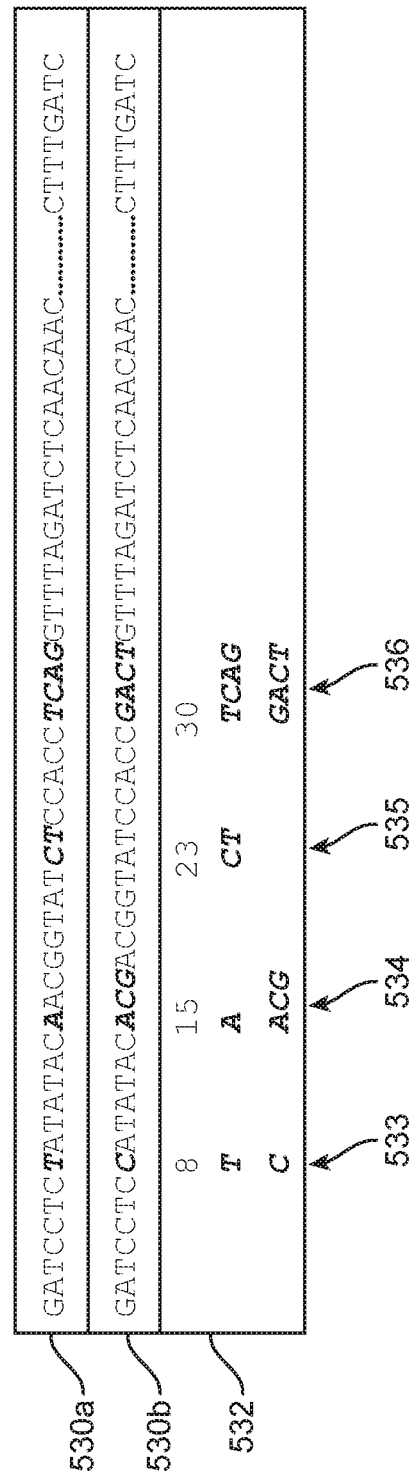
Figure 5D:
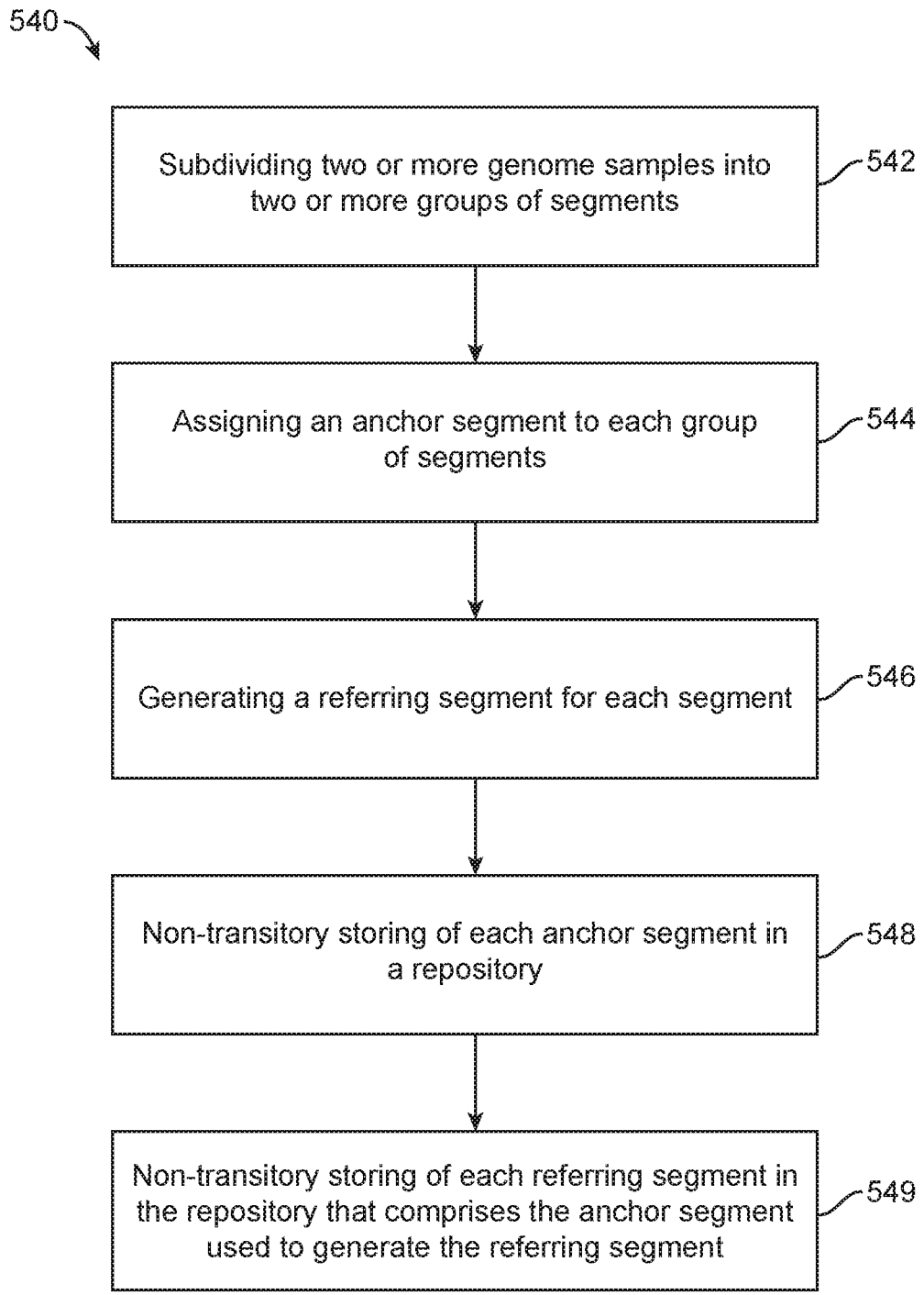
Figure 5E:
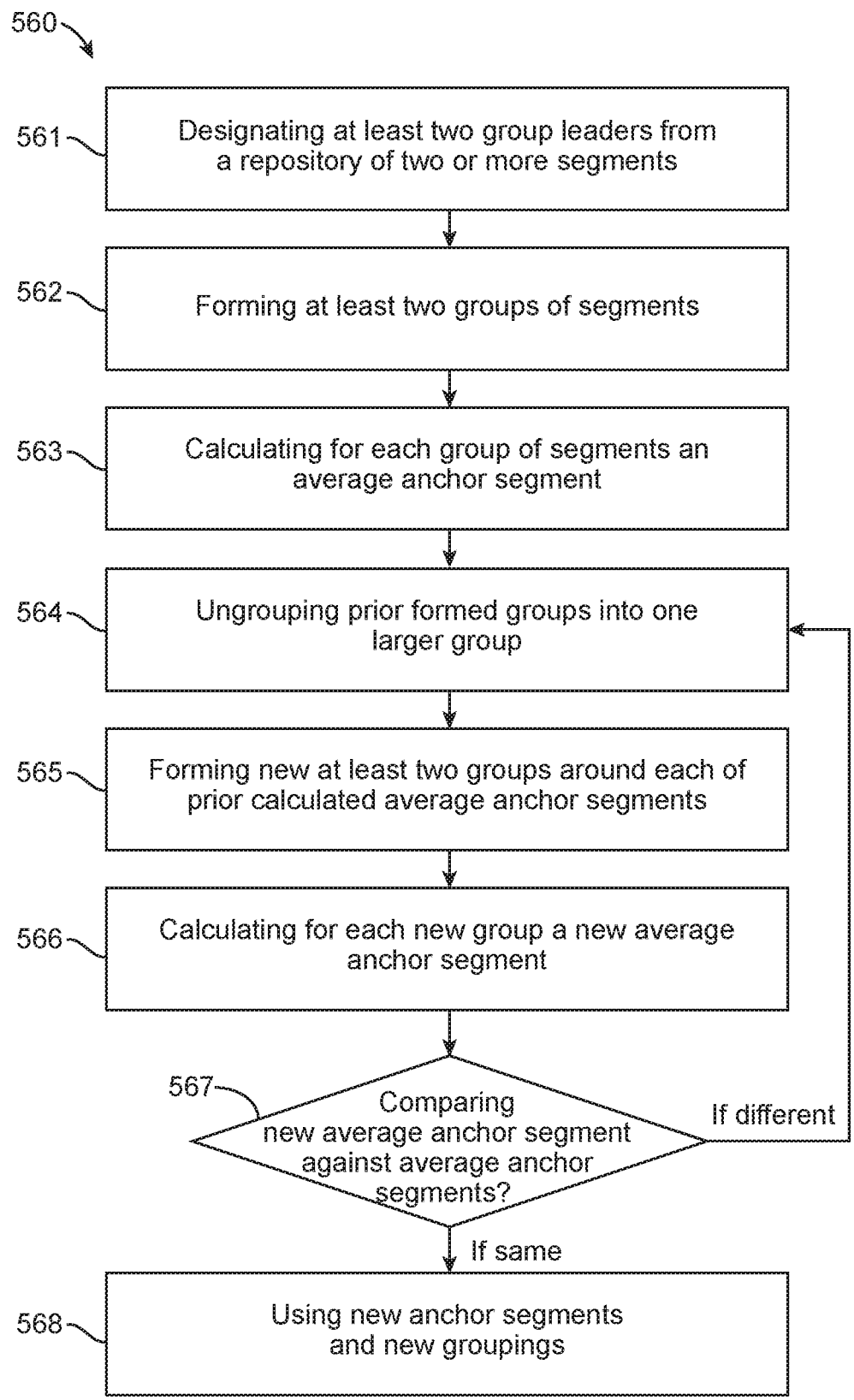

A FIG. 5 series of figures may comprise FIG. 5A through and including FIG. 5E. These FIG. 5 series of figures may address a process of using anchor segments and referring segments for at least a purpose of minimizing storage space as related to non-transitory storing of segments and/or sequences.

FIG. 5A may depict a flow diagram of exemplary steps for the process of using anchor segments and referring segments to minimize storage space.

FIG. 5B may depict results from three different examples of utilizing anchor segments and referring segments to minimize storage space.

FIG. 5C may depict two example genome samples and one or more variations as between those two genome samples. FIG. 5C may also depict various examples of different types of the one or more variations. Alternatively, FIG. 5C may depict an example of aligning a genome sample with an anchor segment in accordance with one or more embodiments of the invention.

FIG. 5D may depict a flow diagram of exemplary steps for a process of using multiple anchor segments and multiple referring segments to minimize storage space.

FIG. 5E may depict a flow diagram of exemplary steps for a process of using calculated average anchor segments to maximize storage savings.

Figure 6:
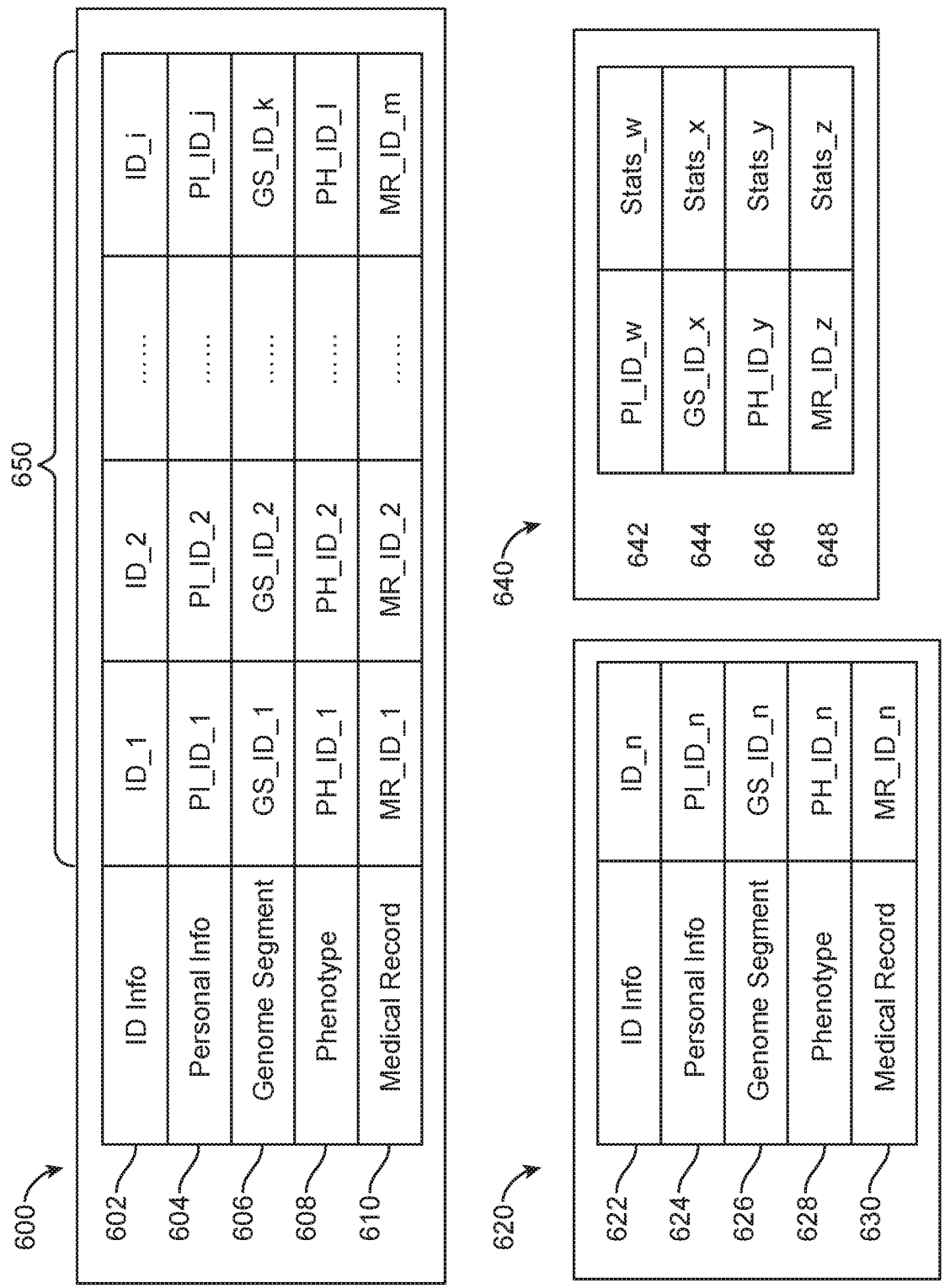

FIG. 6 may depict an example of a linkage record with a set of IDs in accordance with one or more embodiments of the invention.

Figure 7:
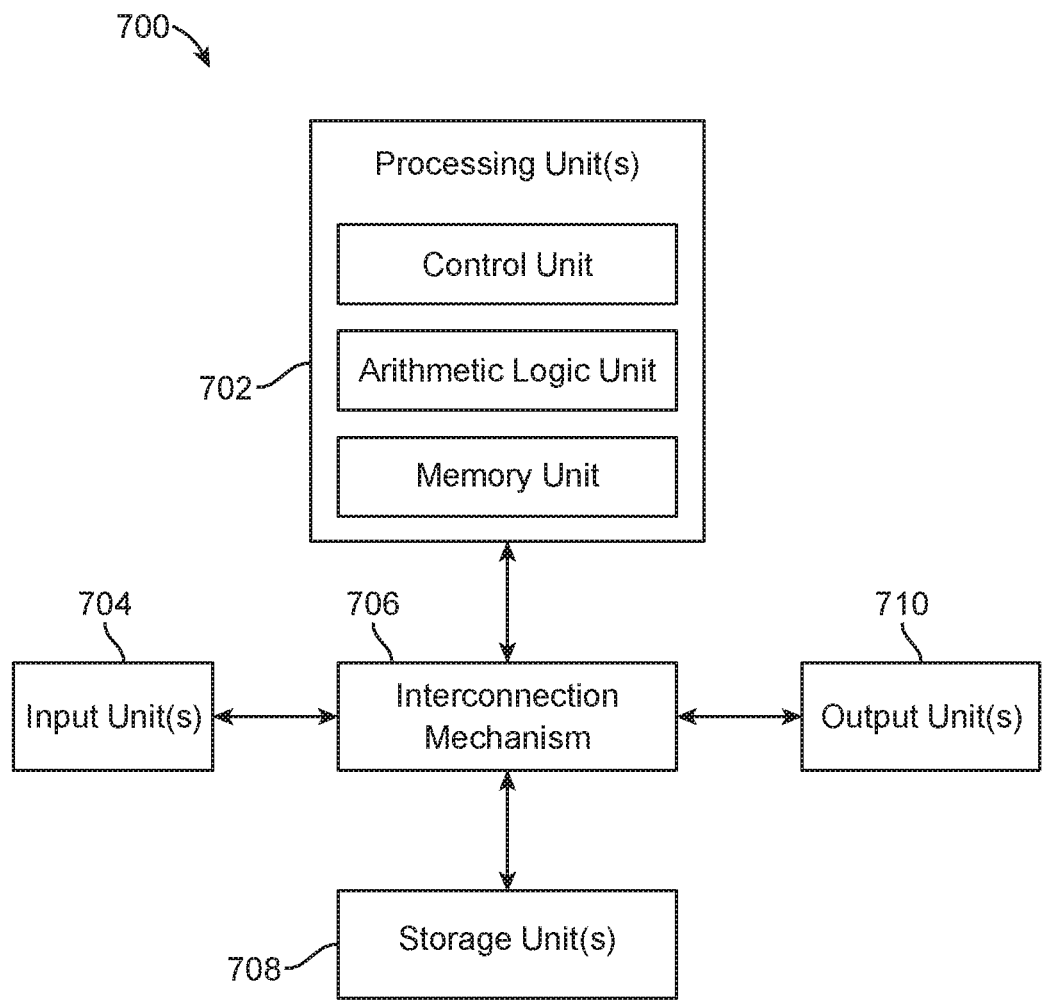

FIG. 7 may depict an example of a computer system to process and non-transitorily store one or more of the following: genome sequences, segments, associated information, anchor segments, referring segments, and align segments in accordance with one or more embodiments of the invention.

Figure 8A:
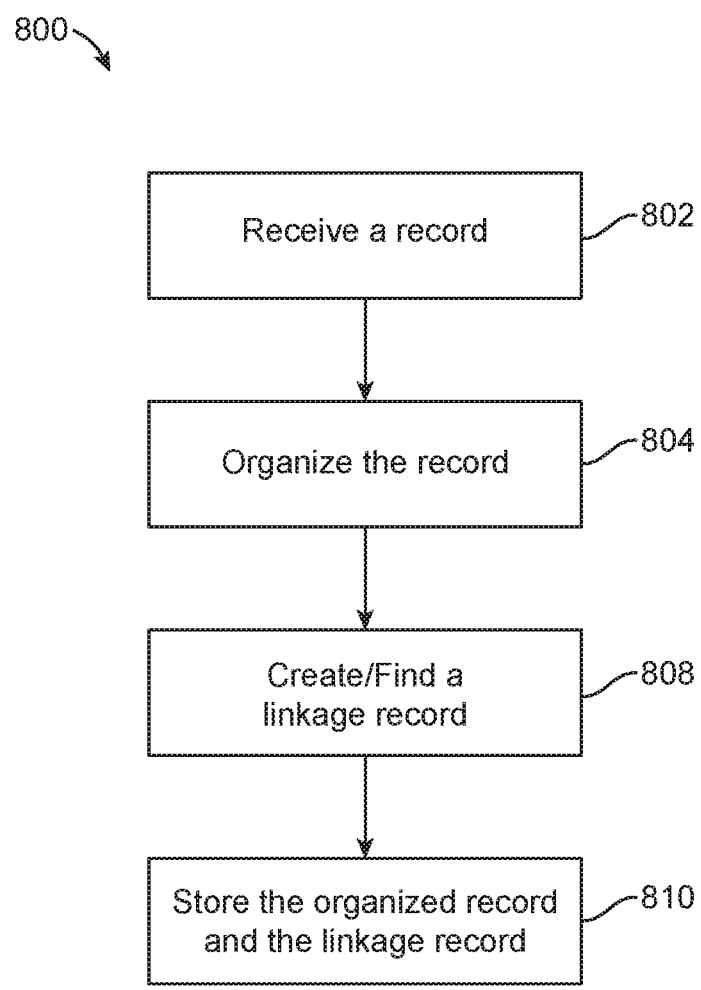
Figure 8B:
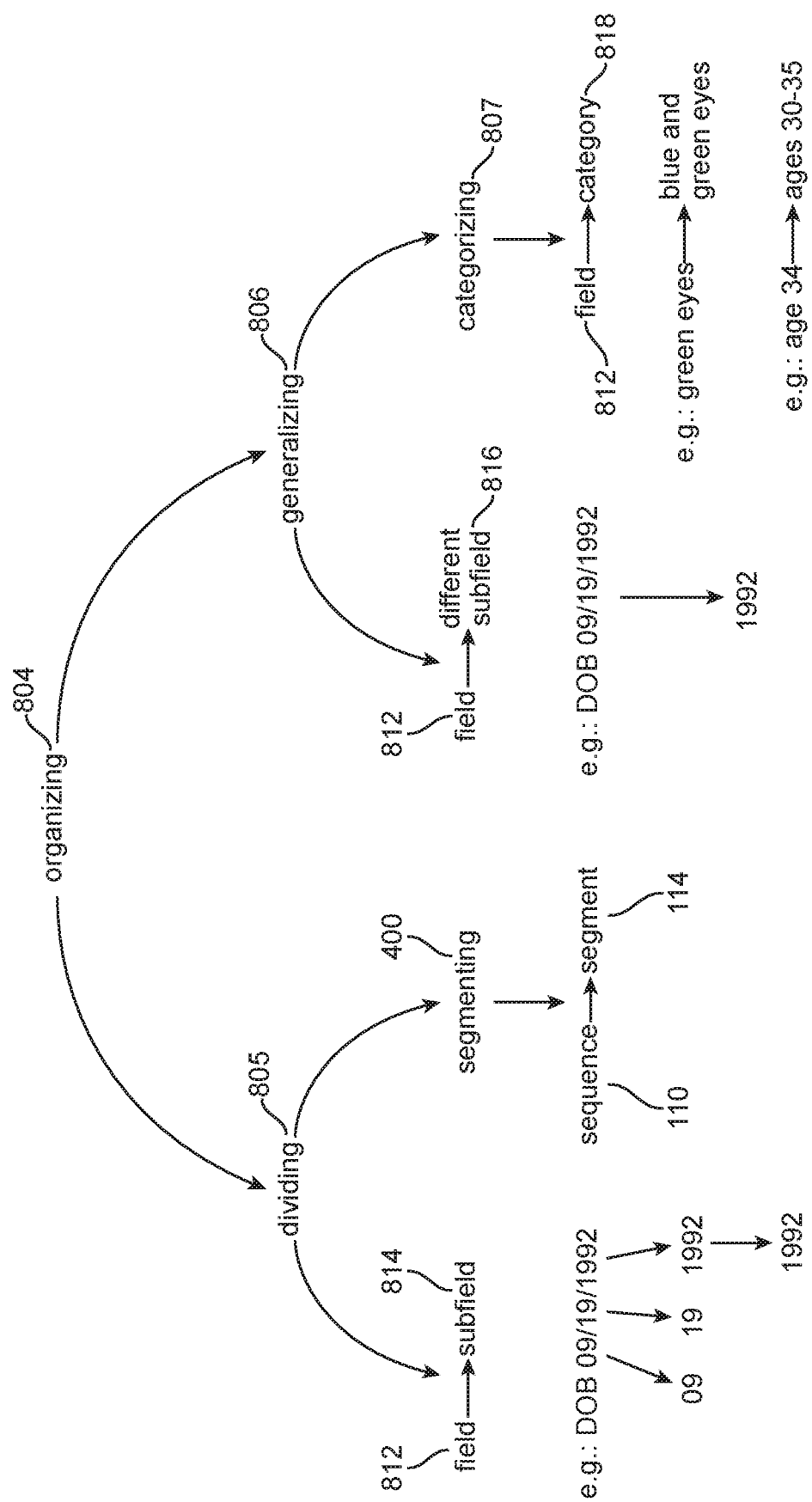

A FIG. 8 series of figures may comprise FIG. 8A through and including FIG. 8B. These FIG. 8 series of figures may address a process for processing the one or more genome sequences and associated information.

FIG. 8A may depict a flow diagram of exemplary steps for the process for processing the one or more genome sequences and the associated information, beginning with a step of receiving a record.

FIG. 8B may depict relationships among organizing, dividing, segmenting, generalizing, and categorizing.

Figure 9:
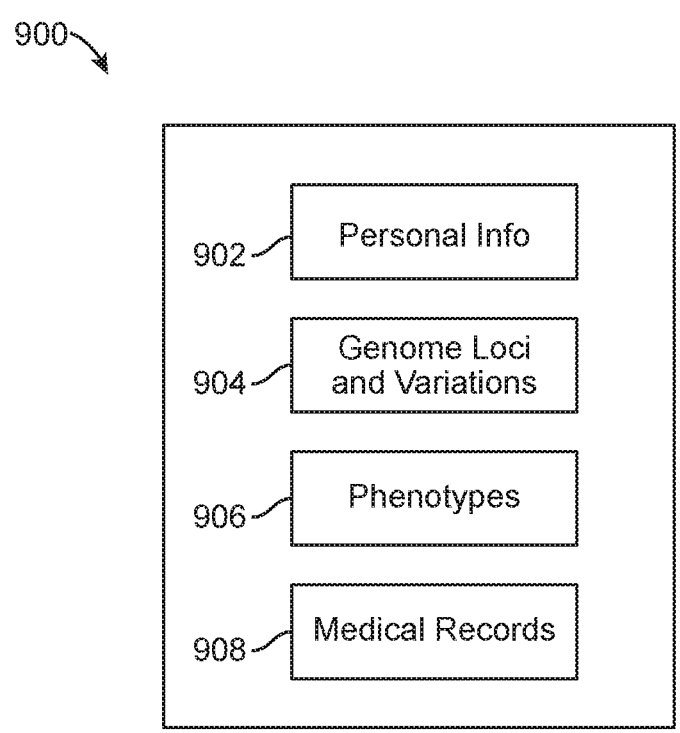

FIG. 9 may depict an example of typical data that may be found in a genome wide association study (GWAS) record or other genetic study results record in accordance with one or more embodiments of the invention.

Figure 10:
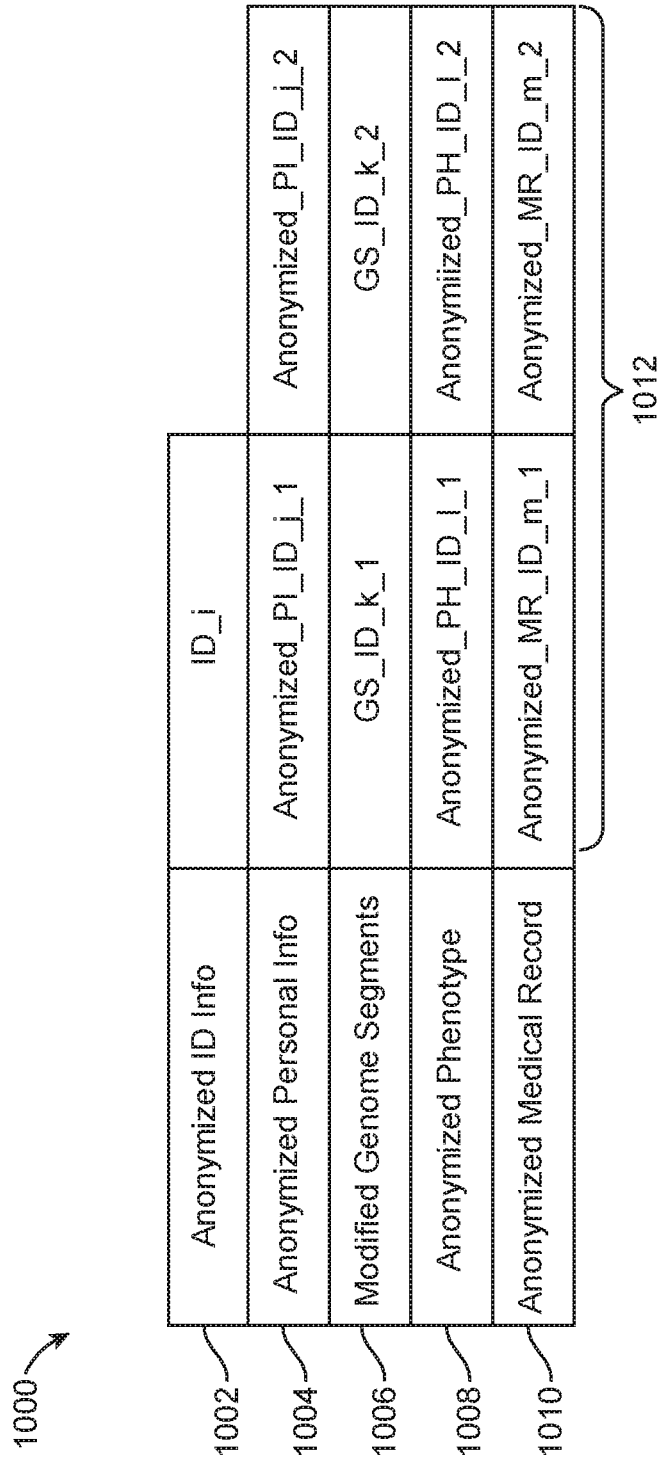

FIG. 10 may depict an example of an anonymized linkage record in accordance with one or more embodiments of the invention.

Figure 11A:
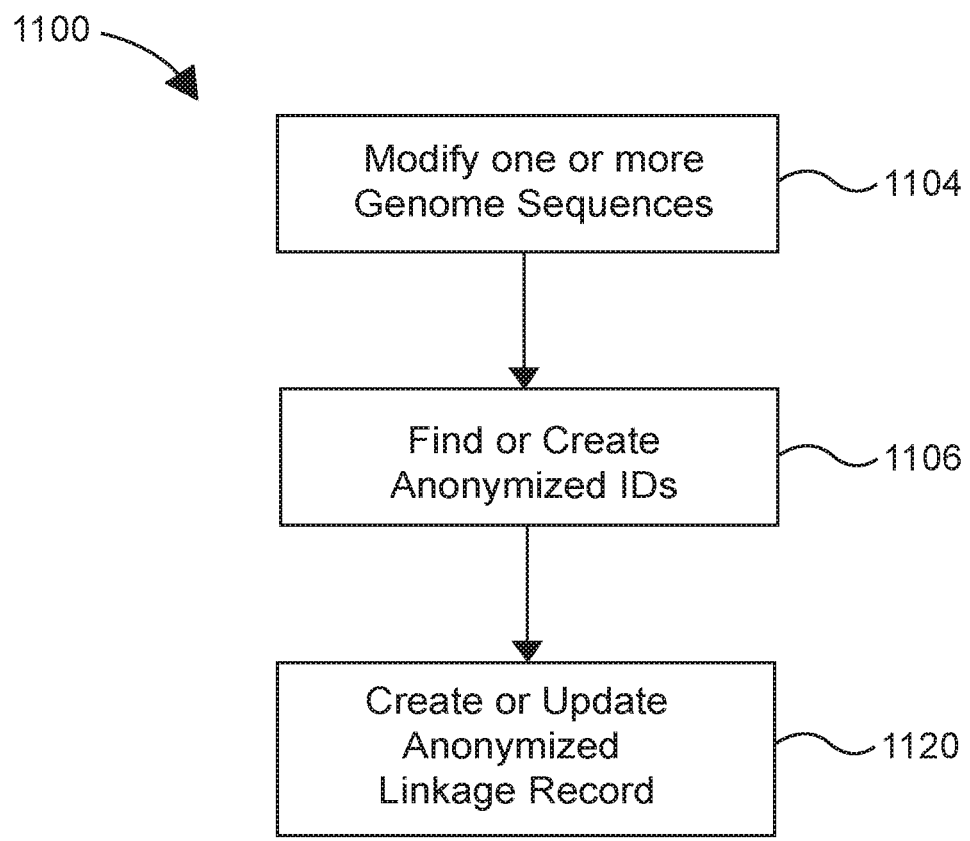
Figure 11B:
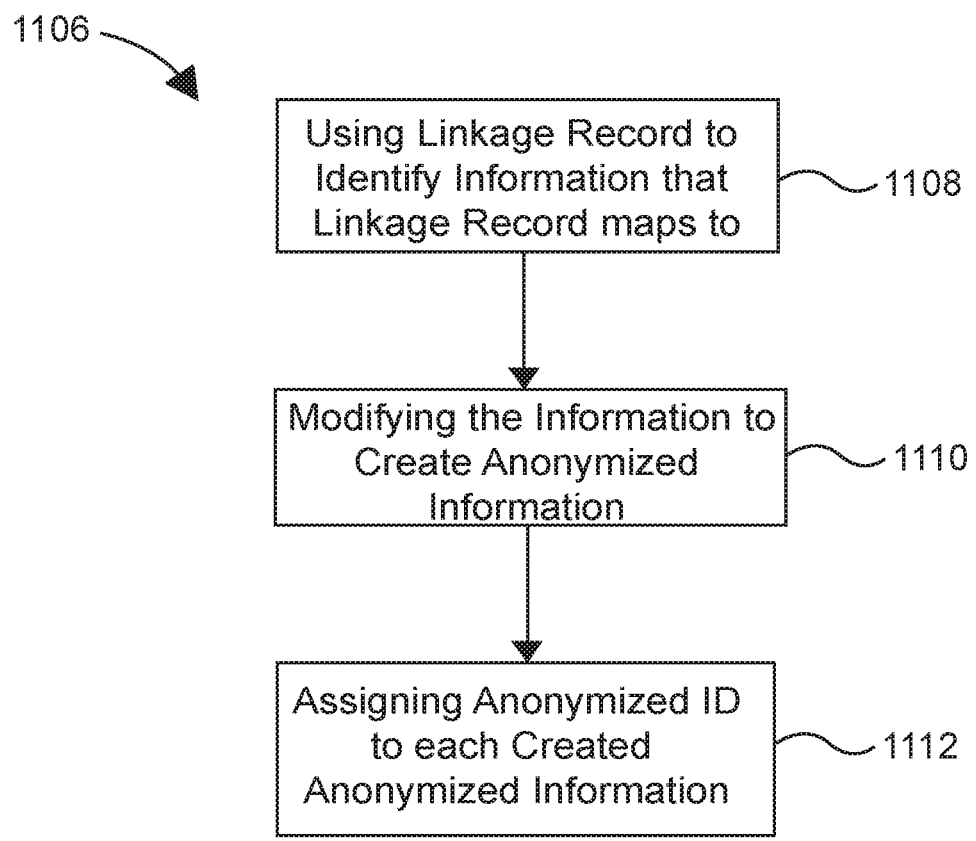
Figure 11C:
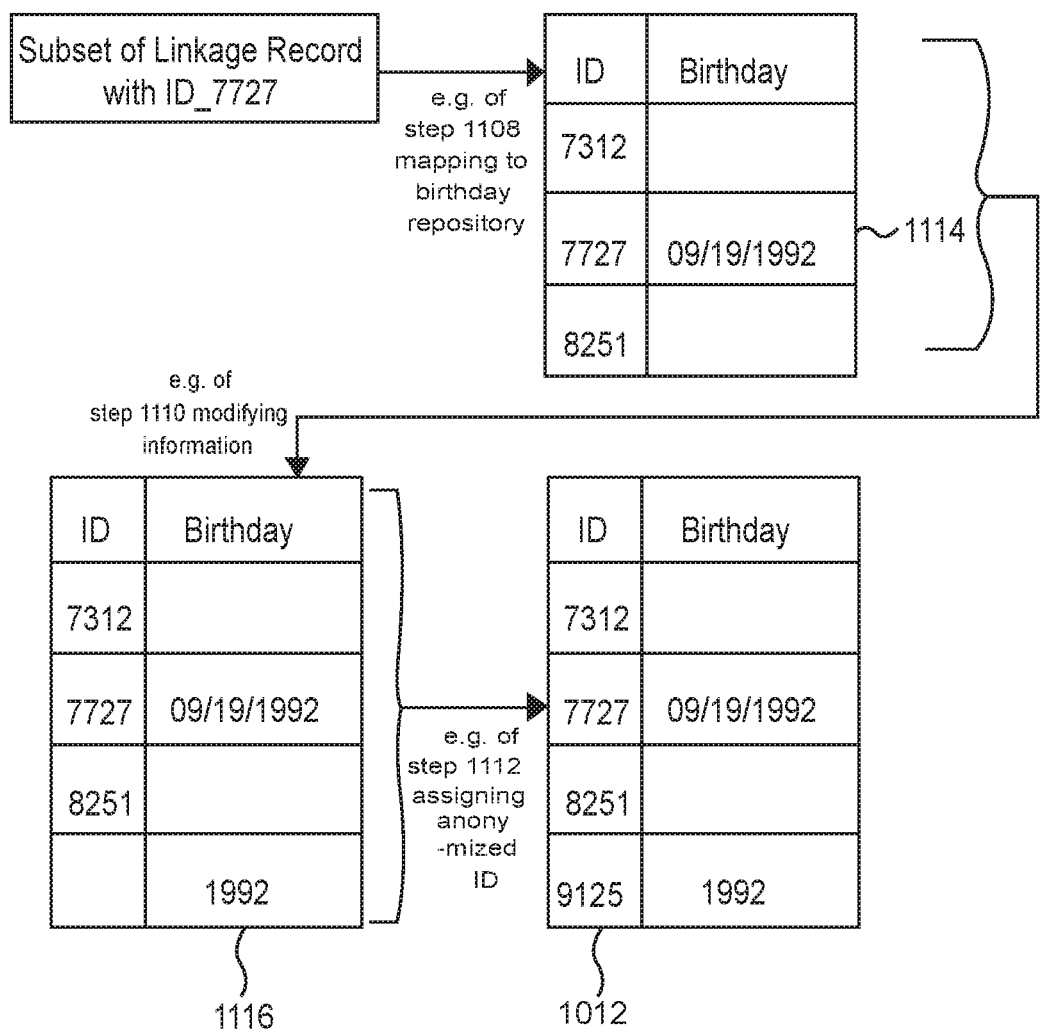
Figure 11D:
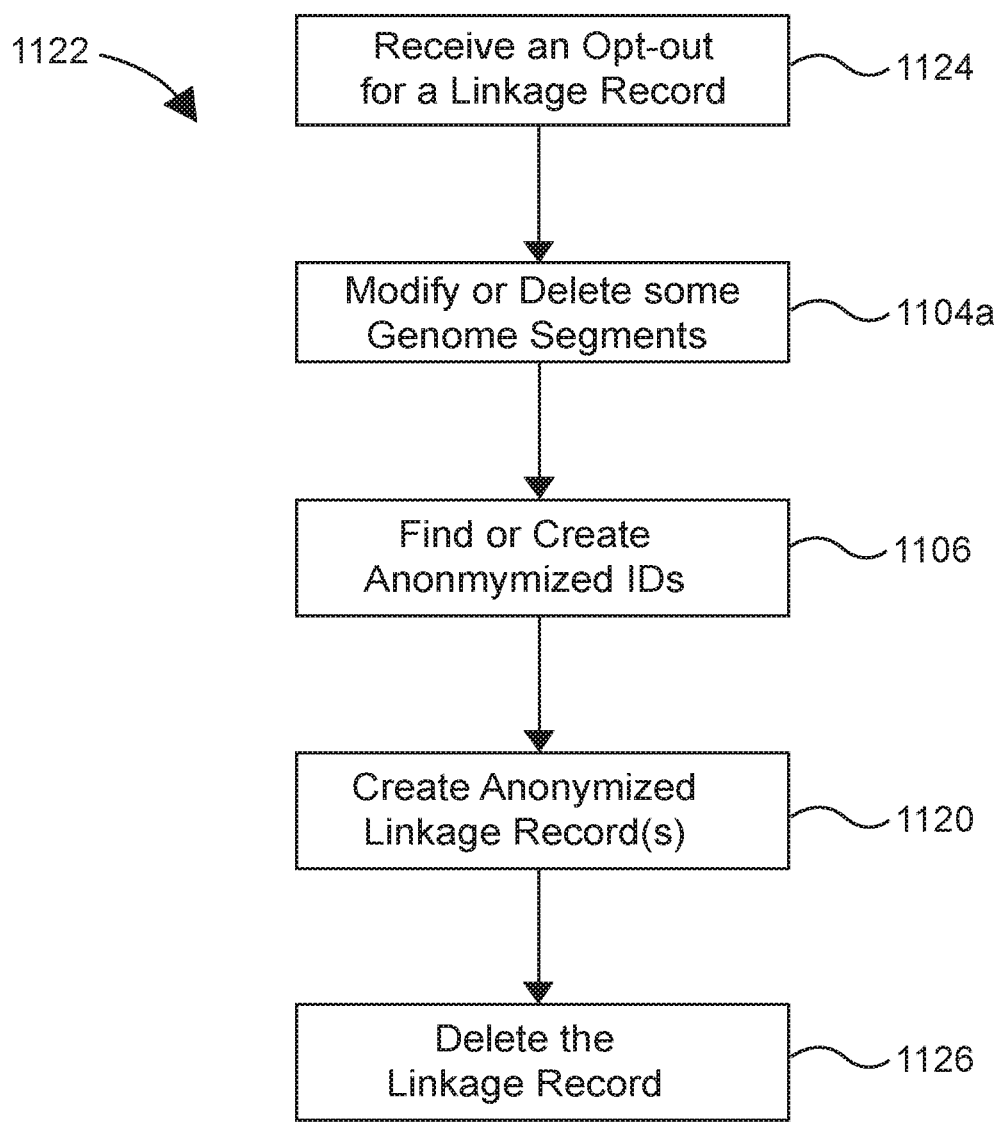

A FIG. 11 series of figures may comprise FIG. 11A through and including FIG. 11D. These FIG. 11 series of figures may address a process for anonymizing a linkage record.

FIG. 11A may depict a flow diagram of exemplary steps for the process for anonymizing the linkage record which may result in creation or updating of the anonymized linkage record of FIG. 10.

FIG. 11B may depict a flow diagram of exemplary steps for a process of finding and/or creating anonymized IDs.

FIG. 11C may depict an example of how a given anonymized linkage record may be created from a given linkage record.

FIG. 11D may depict a flow diagram of exemplary steps of an example of an opt-out procedure to convert a linkage record into at least one anonymized linkage record in accordance with one or more embodiments of the invention.

Figure 12A:
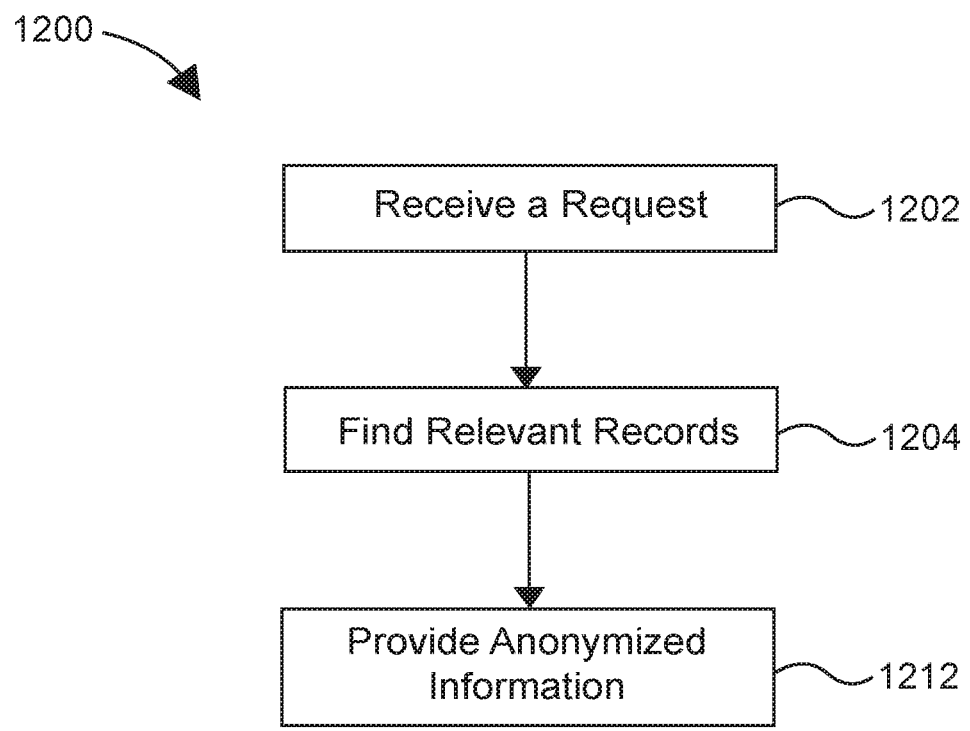
Figure 12B:
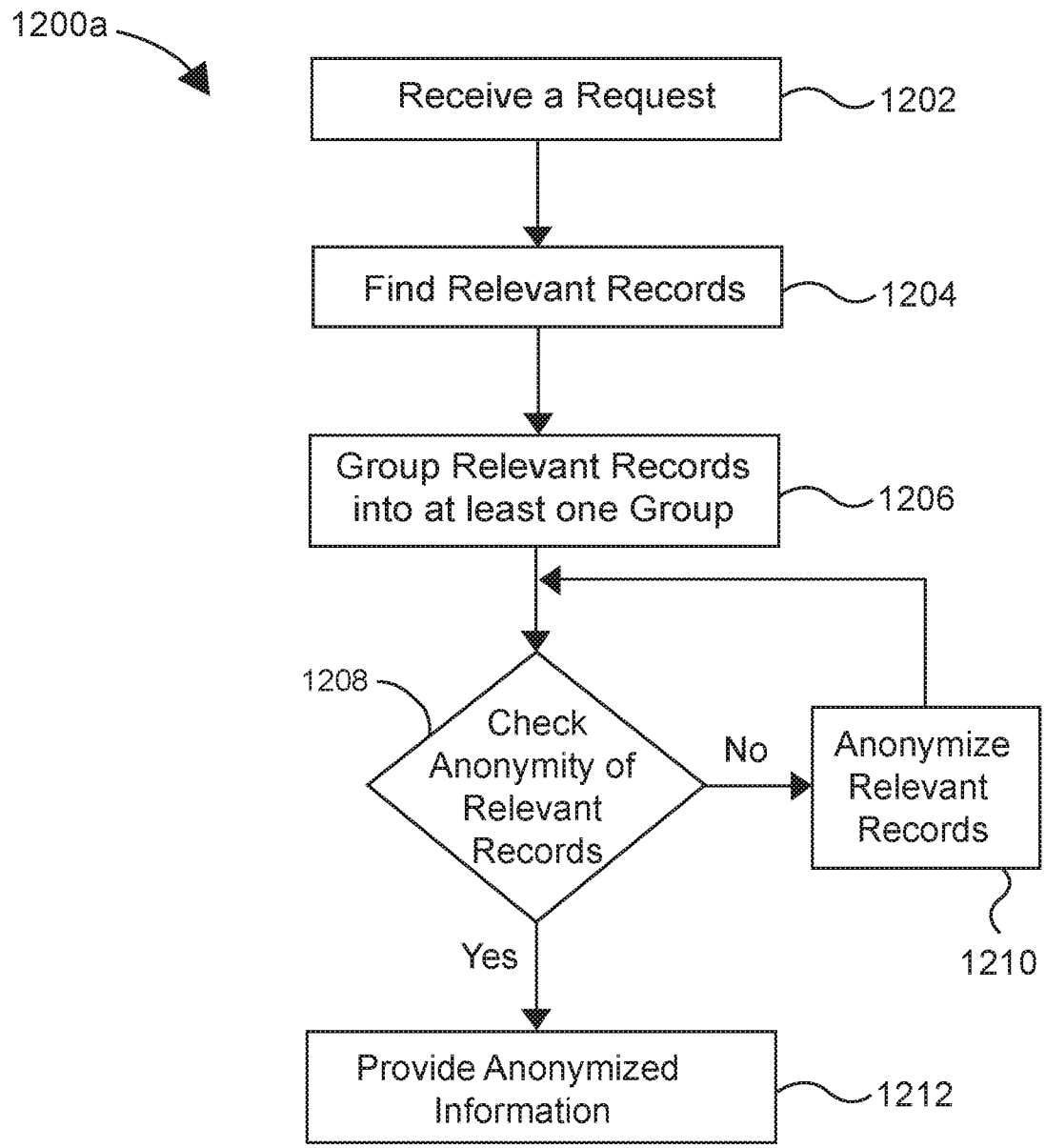
Figure 12C:
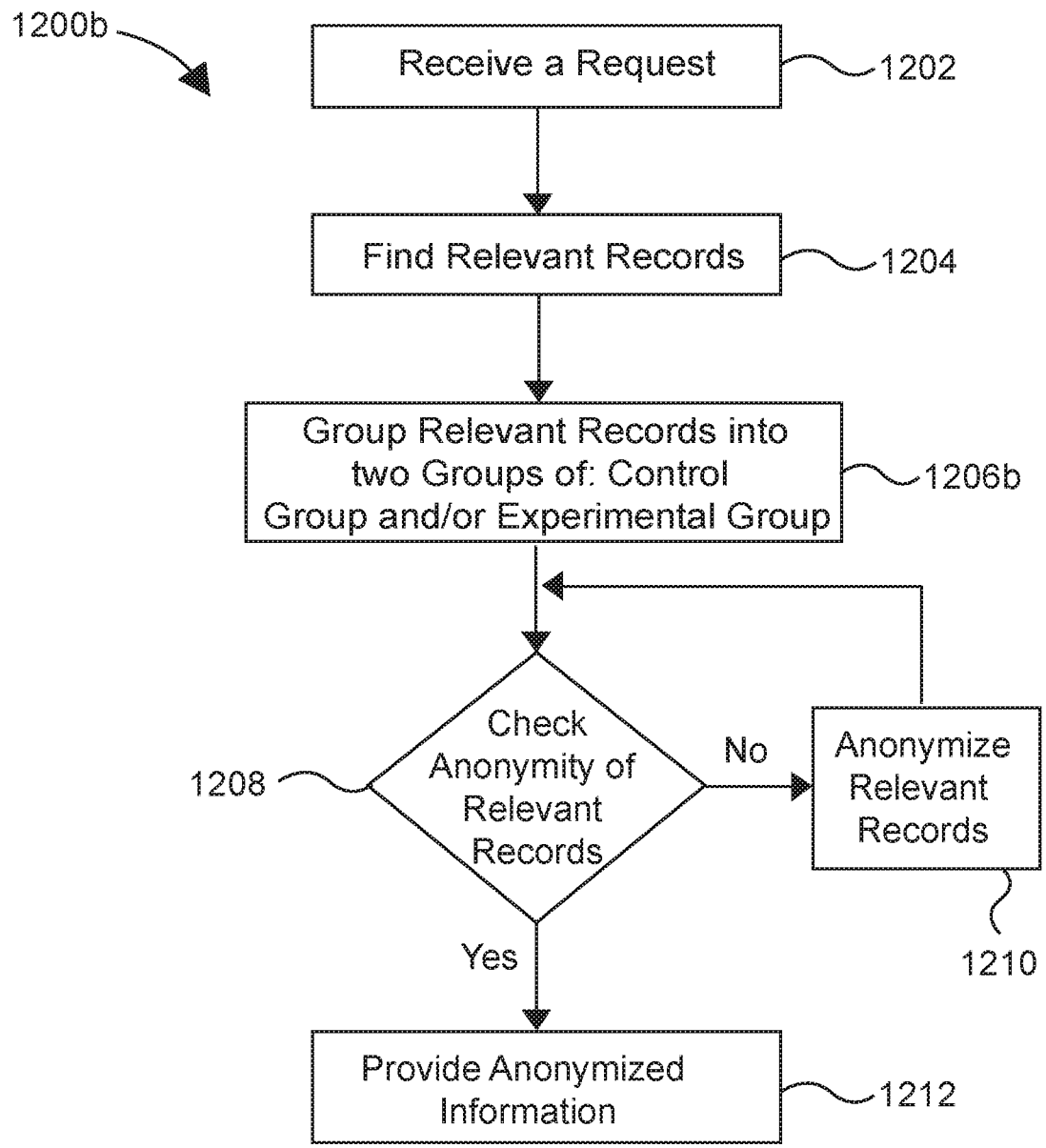
Figure 12D:
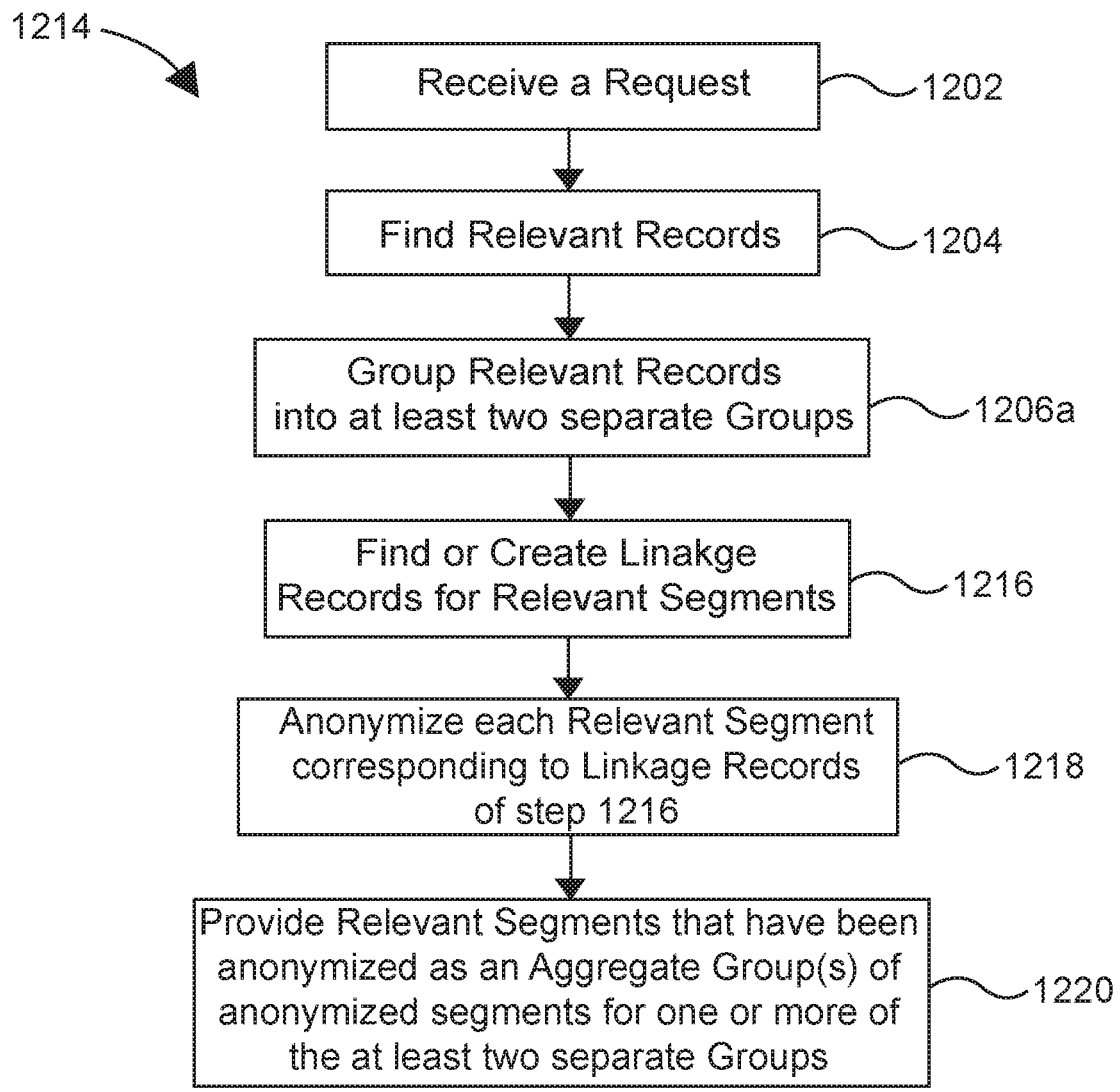
Figure 12E:
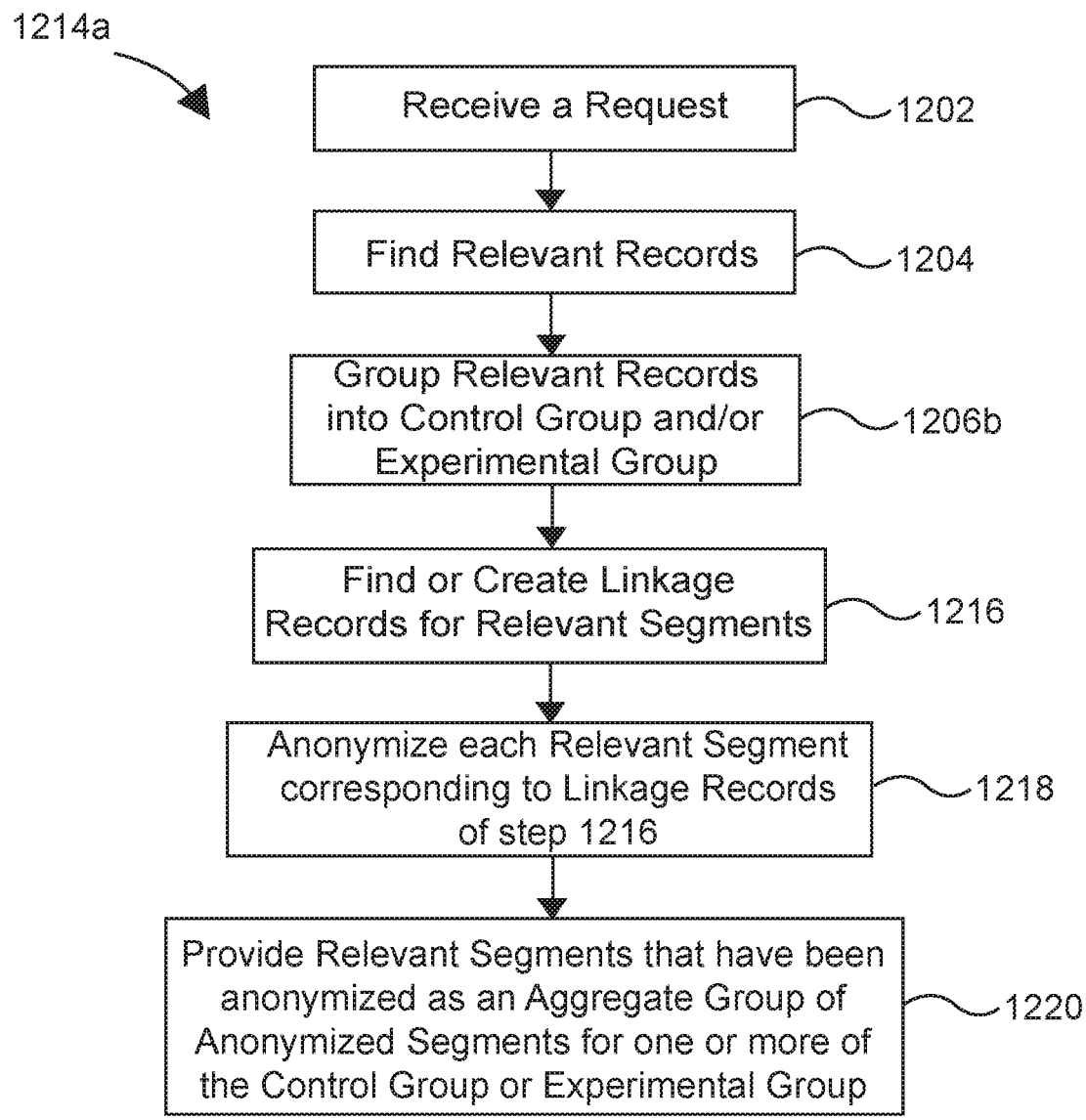

A FIG. 12 series of figures may comprise FIG. 12A through and including FIG. 12E. These FIG. 12 series of figures may address processes for processing a request for genetic study results of genetic variants, such as, but not limited to, GWAS results.

FIG. 12A may depict a flow diagram of exemplary steps for processing the request for the genetic study results of the genetic variants.

FIG. 12B may depict a flow diagram of exemplary steps for processing the request for the genetic study results of the genetic variants.

FIG. 12C may depict a flow diagram of exemplary steps for processing the request for the genetic study results of the genetic variants.

FIG. 12D may depict a flow diagram of exemplary steps for processing the request for the genetic study results of the genetic variants; wherein the process may comprise a grouping step.

FIG. 12E may depict a flow diagram of exemplary steps for processing the request for the genetic study results of the genetic variants; wherein the process may comprise a grouping step.

Figure 13A:
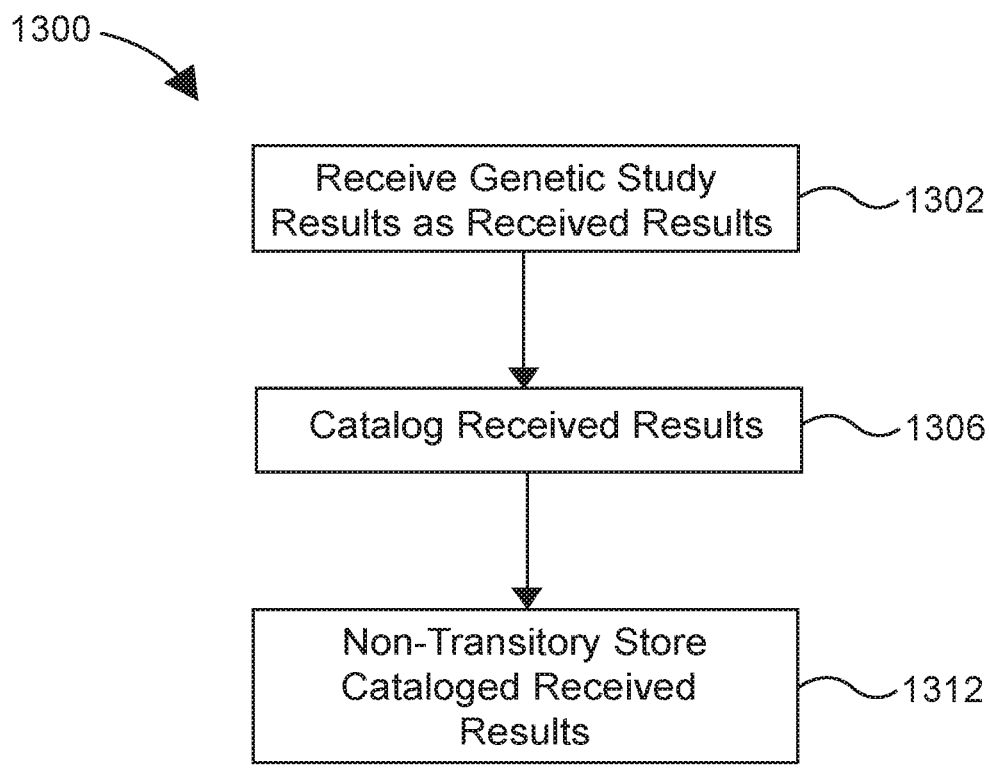
Figure 13B:
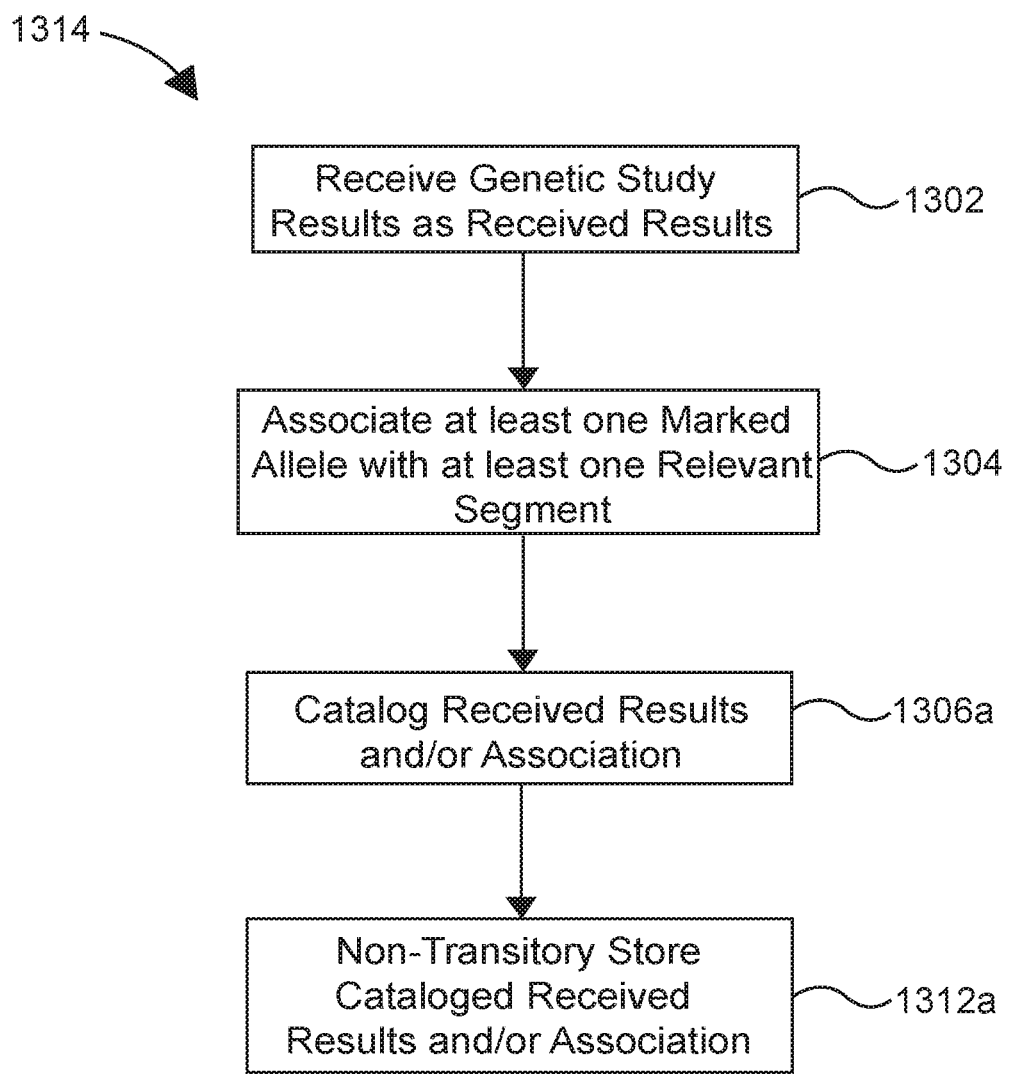
Figure 13C:
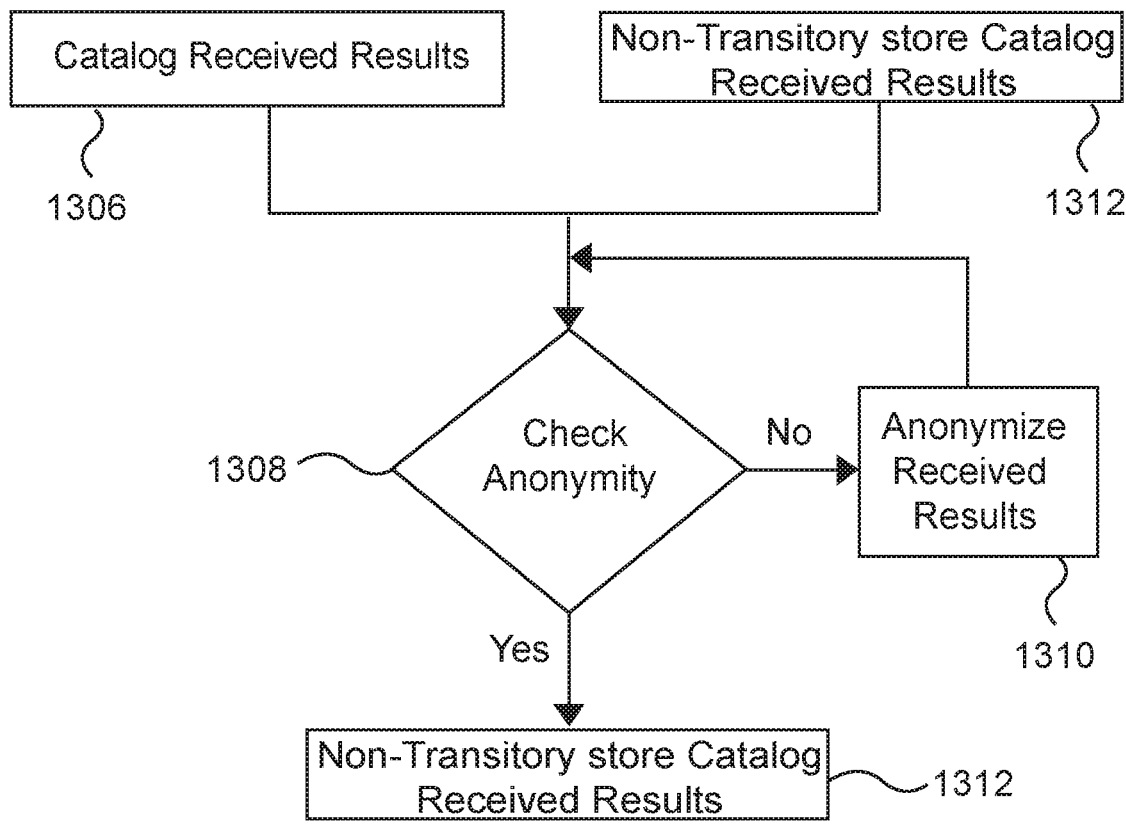

A FIG. 13 series of figures may comprise FIG. 13A through and including FIG. 13C. These FIG. 13 series of figures may address a process for processing received genetic study results.

FIG. 13A may depict a flow diagram of exemplary steps for processing the received genetic study results.

FIG. 13B may depict a flow diagram of exemplary steps for processing the received genetic study results.

FIG. 13C may depict additional steps for checking and/or anonymizing the received genetic study results.

Figure 14A:
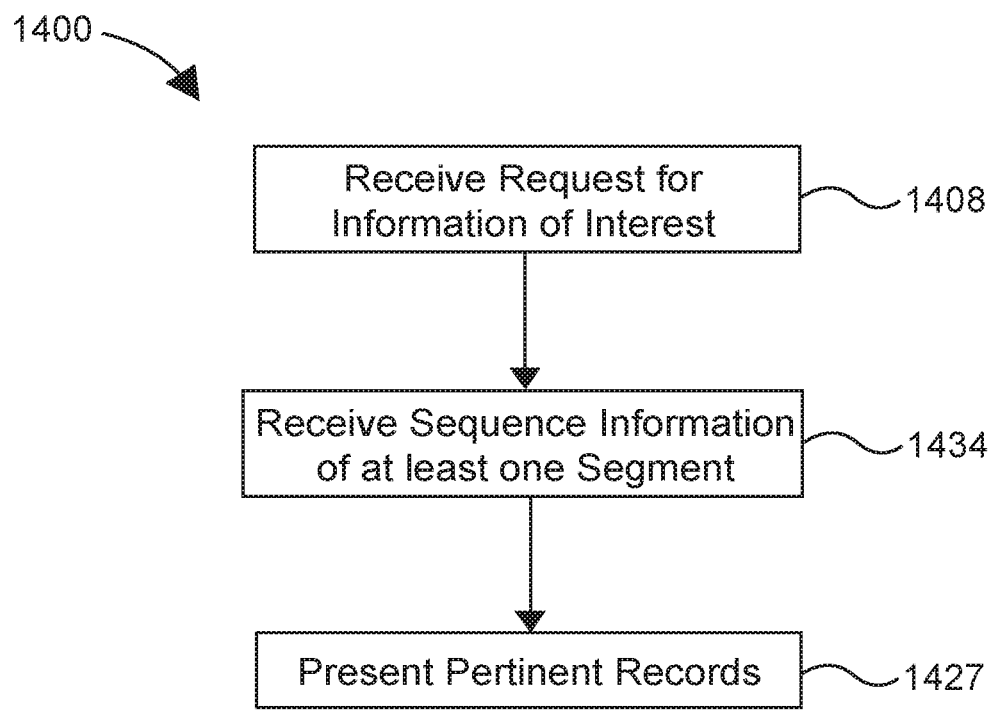
Figure 14B:
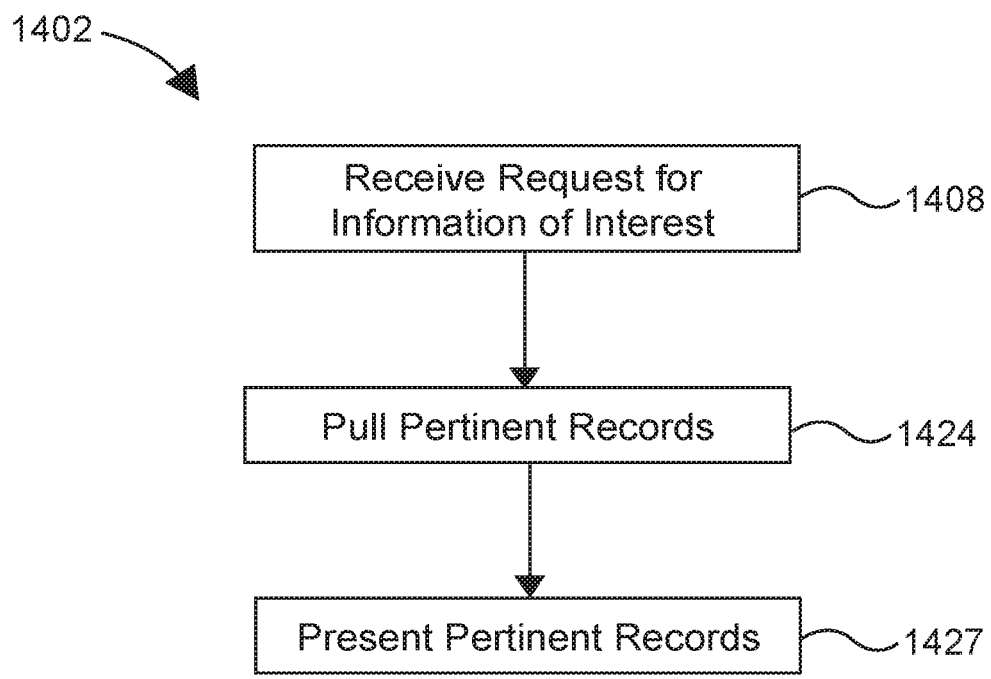
Figure 14C:
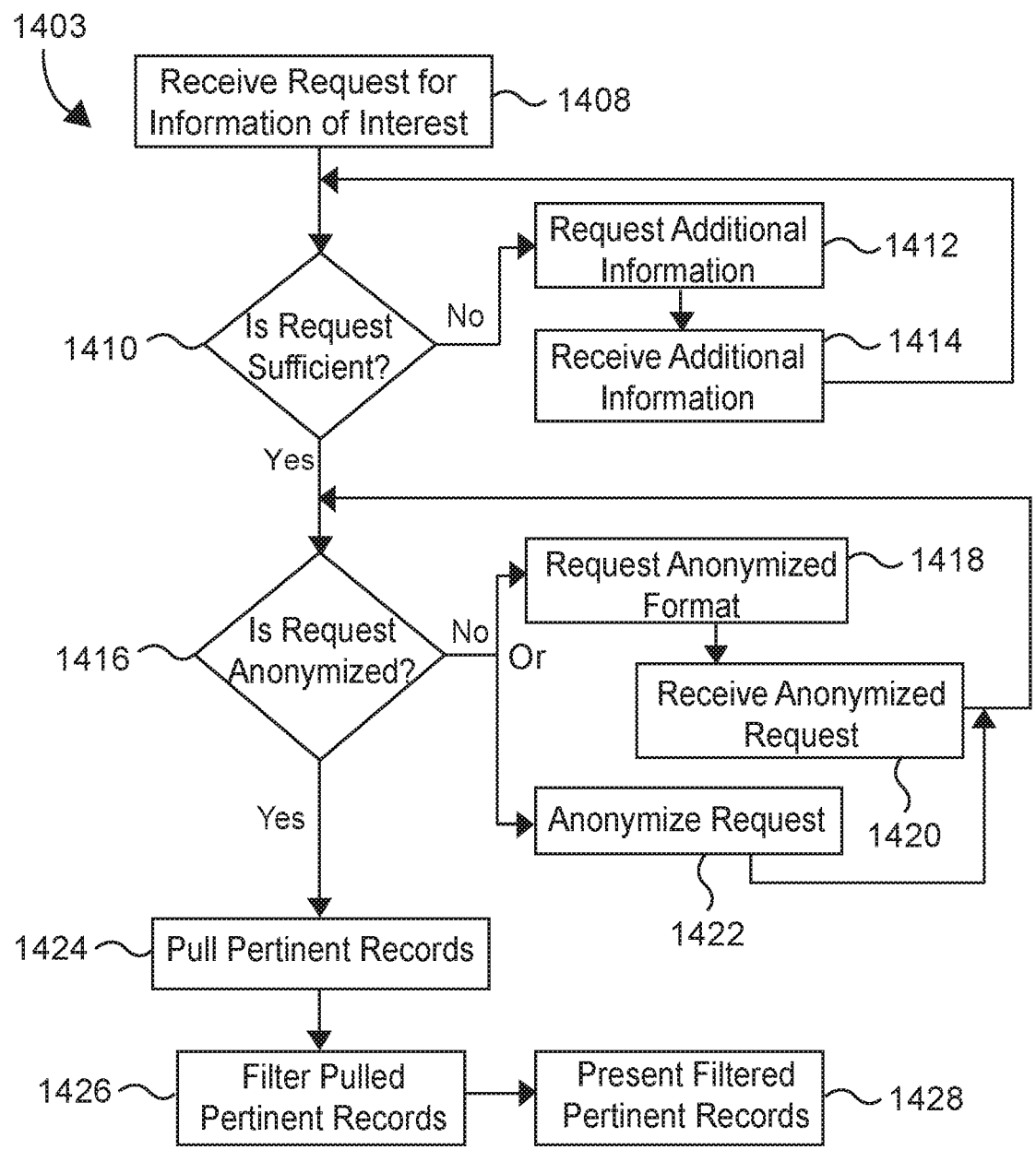
Figure 14D:
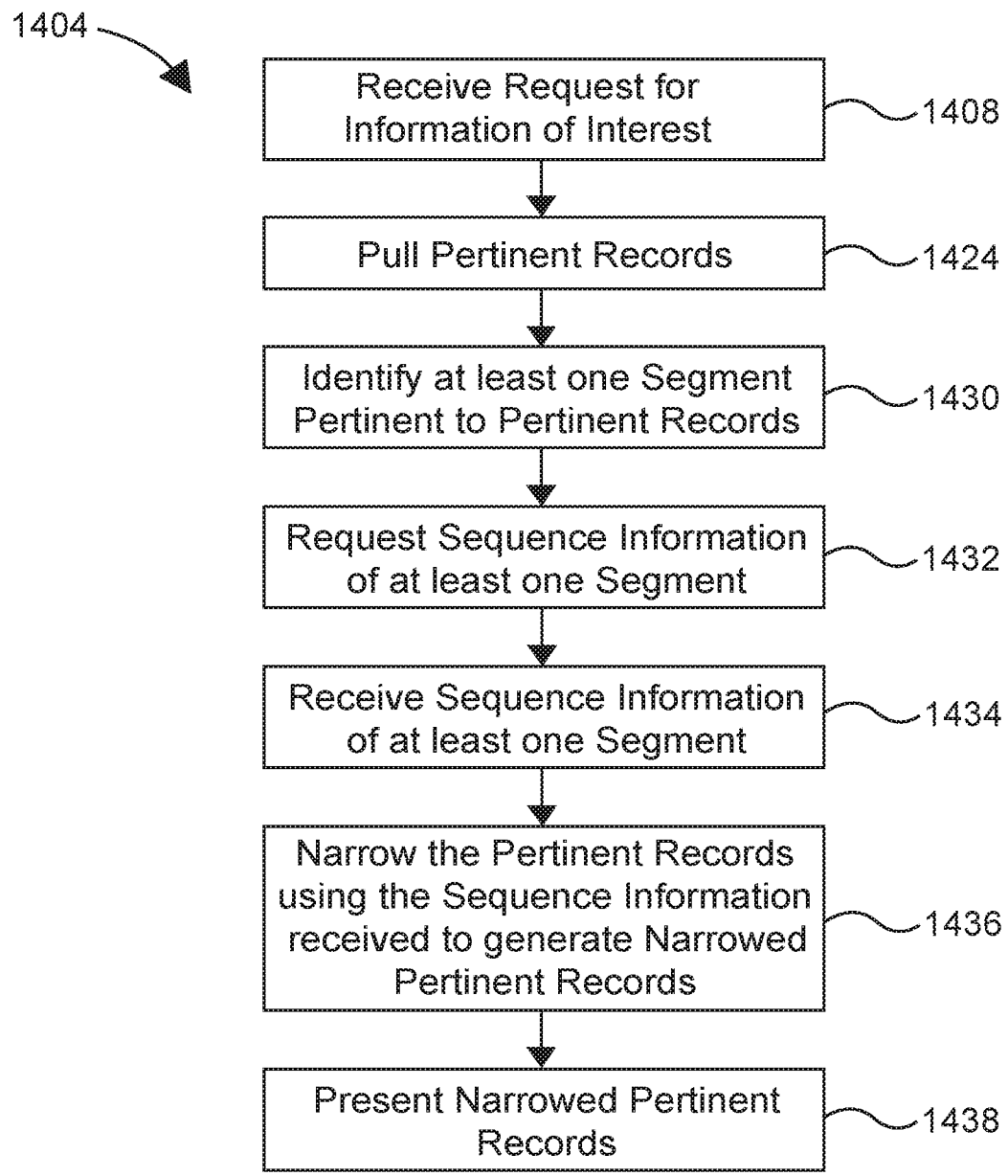
Figure 14E:
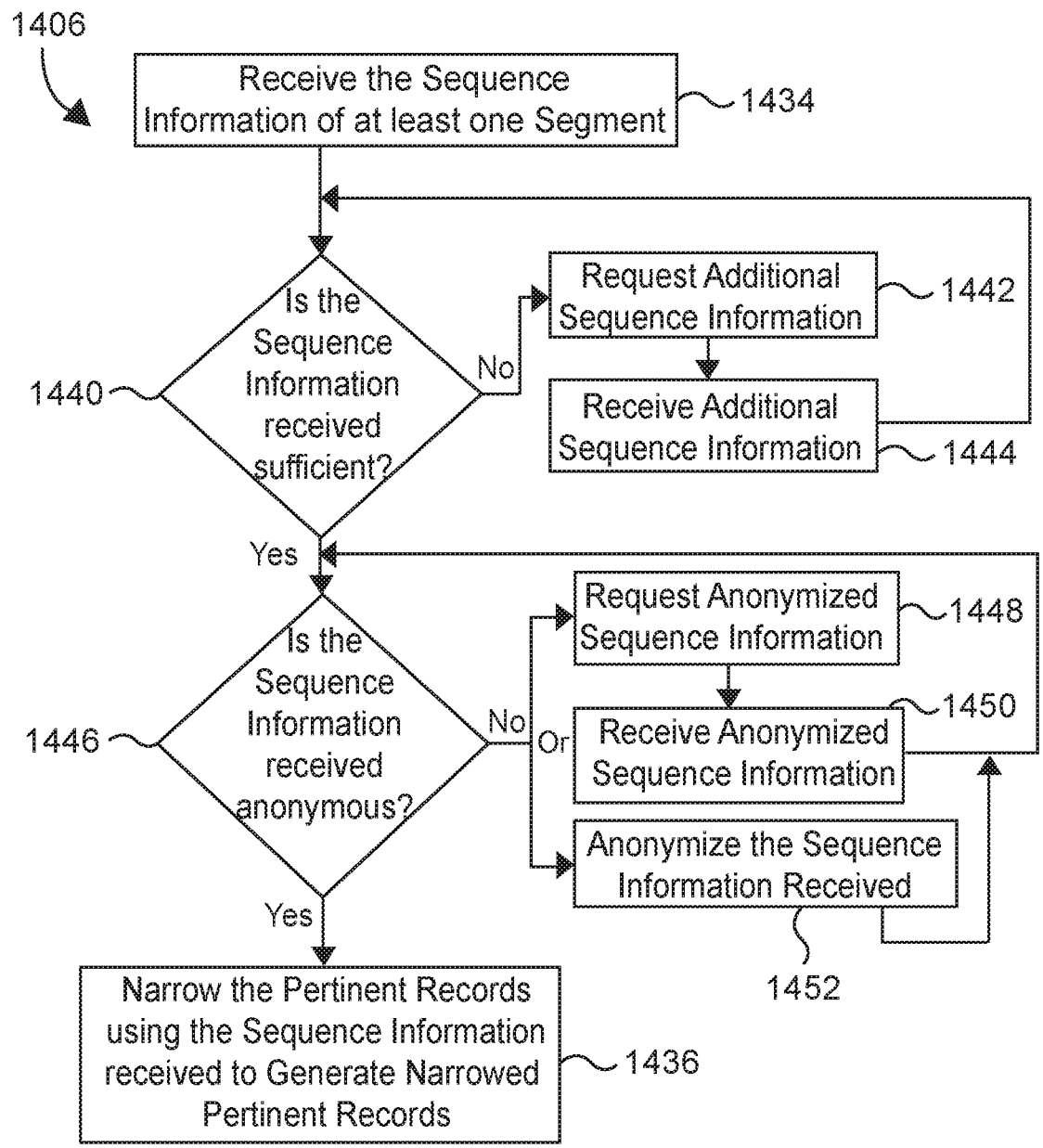
Figure 14F:
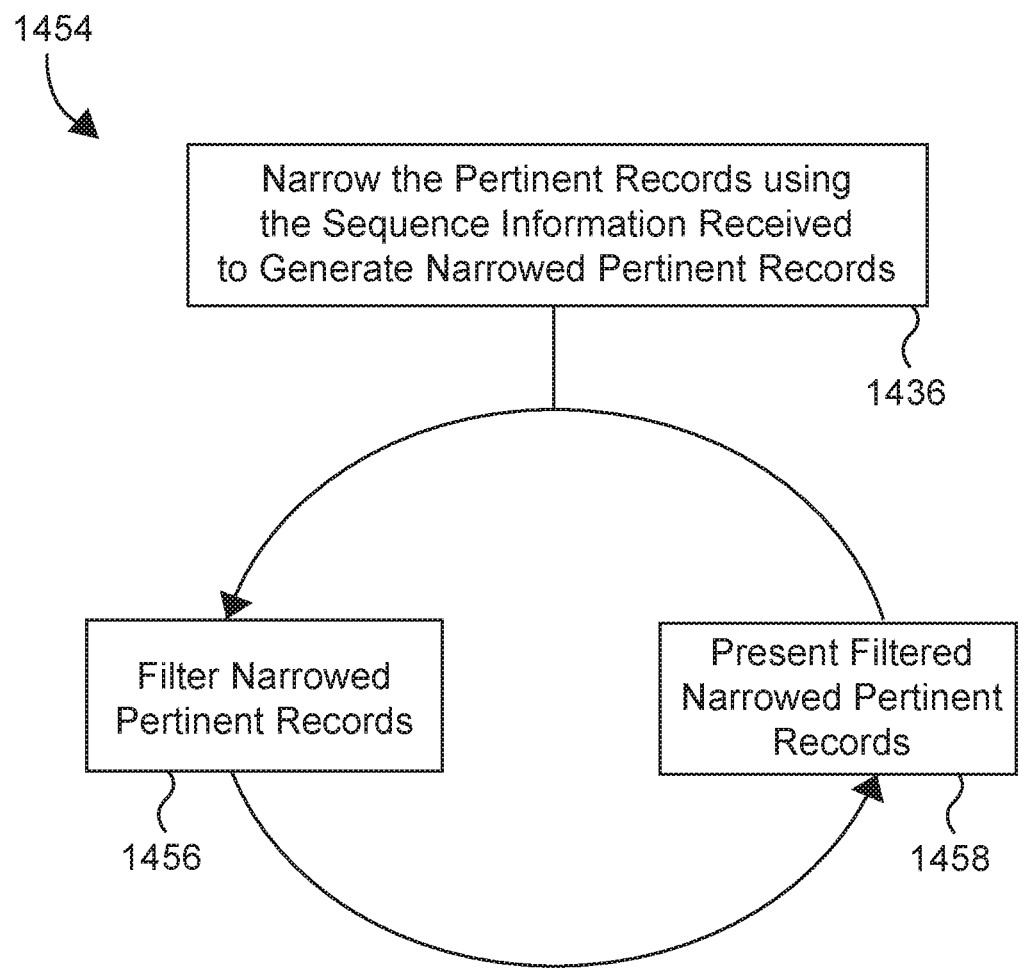
Figure 14G:
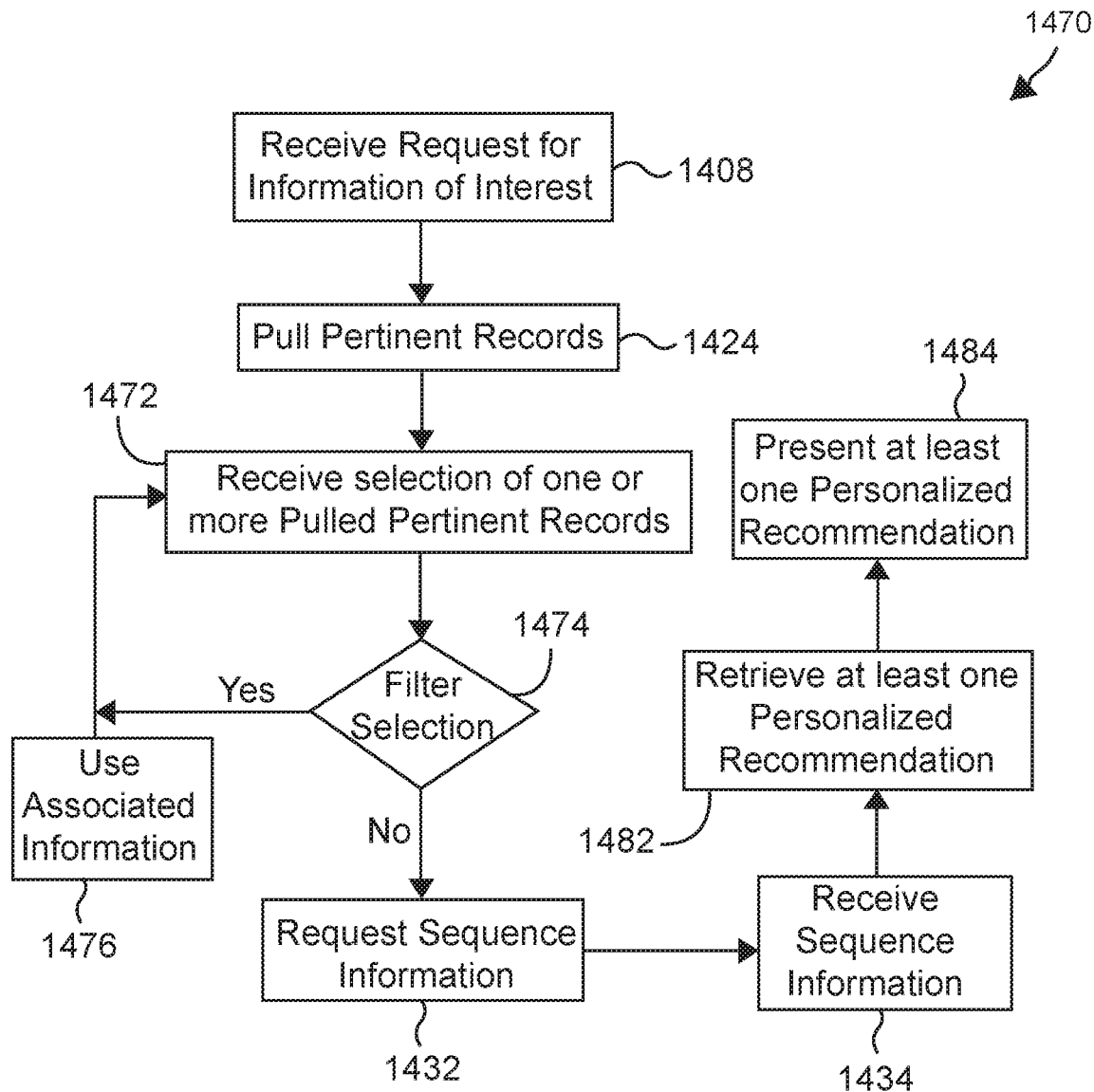

A FIG. 14 series of figures may comprise FIG. 14A through and including FIG. 14G. These FIG. 14 series of figures may address a process for generating personalized information of interest pertaining to at least one individual, such as, but not limited to, generating a personalized healthcare recommendation for that at least one individual.

FIG. 14A may depict a flow diagram of exemplary steps for generating the personalized information of interest pertaining to the at least one individual which may be triggered by receiving a request for the personalized information of interest.

FIG. 14B may depict a flow diagram of exemplary steps for generating the personalized information of interest pertaining to the at least one individual which may be triggered by receiving the request for the personalized information of interest.

FIG. 14C may depict a flow diagram of exemplary steps for generating the personalized information of interest pertaining to the at least one individual which may be triggered by receiving the request for the personalized information of interest.

FIG. 14D may depict a flow diagram of exemplary steps for generating the personalized information of interest pertaining to the at least one individual which may be triggered by receiving the request for the personalized information of interest.

FIG. 14E may depict a flow diagram of exemplary steps for receiving sequence information of at least one segment.

FIG. 14F may depict a flow diagram of exemplary steps for narrowing and/or filtering pertinent records.

FIG. 14G may depict a flow diagram of exemplary steps for generating a personalized recommendation pertaining to the at least one individual which may be triggered by receiving the request for the personalized information of interest.

Figure 15:
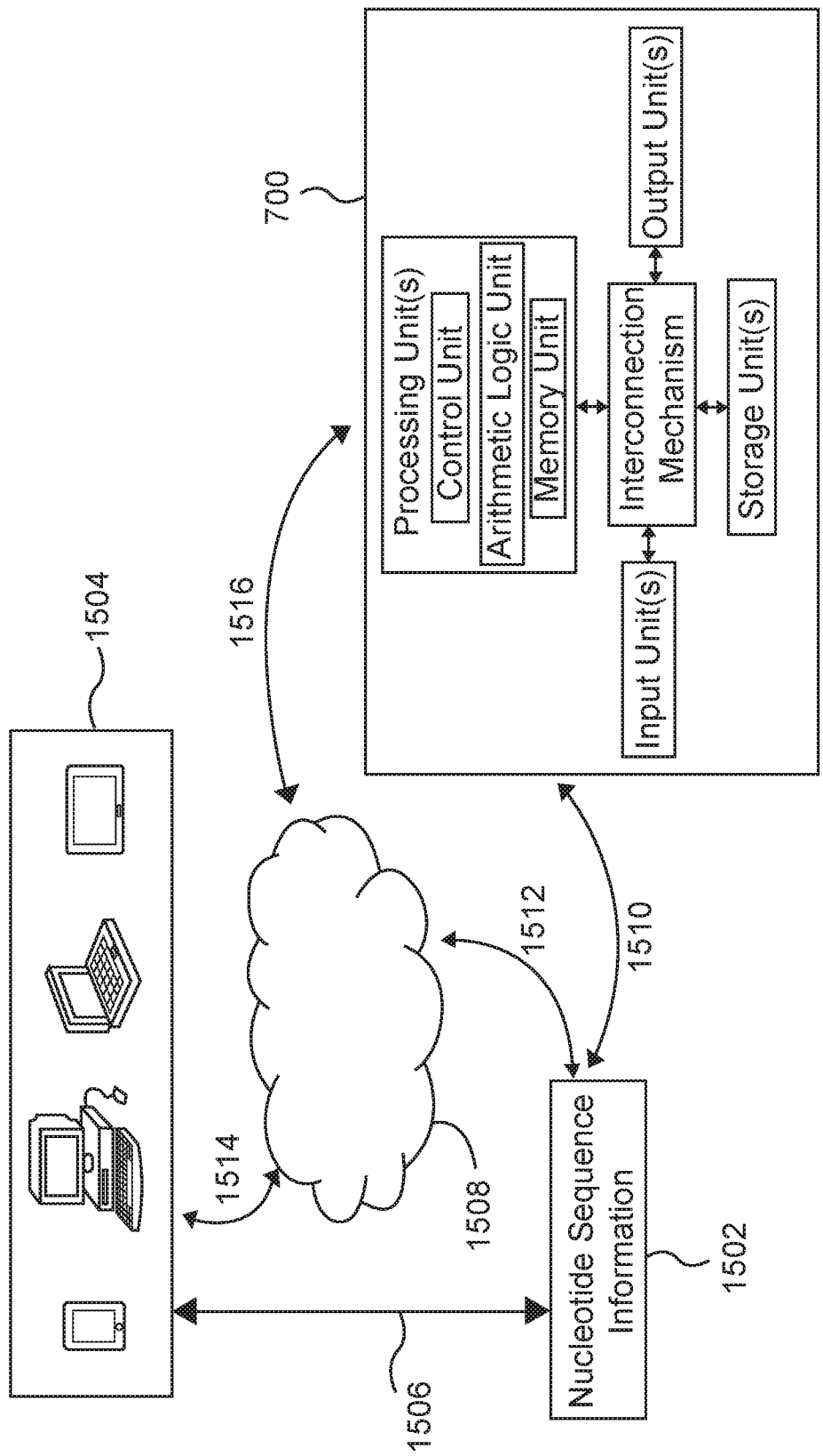

FIG. 15 may depict an example of communicating with a system that processes and non-transitorily stores one or more of the following: genome sequences, segments, associated information, anchor segments, referring segments, and align segments in accordance with one or more embodiments of the invention.

REFERENCE NUMERAL KEY 101 original data 101
110 one or more genome sequences 110
112 sequence-associated-information 112
114 one or more segments of nucleic acid sequences 114 (one or more segments 114)
116 example of DNA sequence 116 or example of DNA segment 116
118 CpG site 118
120 associated information
122 phenotype information 122
124 medical record information 124
126 personal information 126
201 human autosome chromatid 201
202 human autosome chromatid 202
203 human autosome chromatid 203
204 human autosome chromatid 204
205 human autosome chromatid 205
206 human autosome chromatid 206
207 human autosome chromatid 207
208 human autosome chromatid 208
209 human autosome chromatid 209
210 human autosome chromatid 210
211 human autosome chromatid 211
212 human autosome chromatid 212
213 human autosome chromatid 213
214 human autosome chromatid 214
215 human autosome chromatid 215
216 human autosome chromatid 216
217 human autosome chromatid 217
218 human autosome chromatid 218
219 human autosome chromatid 219
220 human autosome chromatid 220
221 human autosome chromatid 221
222 human autosome chromatid 222
231 human X chromatid 231
232 human Y chromatid 232
241 TPDX locus 241
242 D3S1358 locus 242
243 FGA locus 243
244 D5S818 locus 244
245 CSF1PO locus 245
246 D7S820 locus 246
247 D8S1179 locus 247
248 THO1 locus 248
249 VWA locus 249
250 D13S317 locus 250
251 D16S539 locus 251
252 D18S51 locus 252
253 D21S11 locus 253
261 AMEL locus 261
262 AMEL locus 262
271 centromere 271
272 short arm p 272
273 long arm q 273
302 DNA markers 302
304 allele frequency 304
306 genotype frequency 306
310 TPDX locus 310
320 VWA locus 320
330 total probability 330
400 method for segmenting one or more genome sequences 400
402 step of receiving one or more genome sequences 402
405 step of segmenting the one or more genome sequences into one or more segments 405
406 disjoint segments 406
407 overlapping segments 407
408 region of overlap 408
410 using one or more align sequences for segmenting 410
412 step of finding or creating one or more align sequences 412
414 step of processing using genetic map information 414
416 step of further processing using GWAS results 416
420 one or more align sequences 420
425 step of aligning similar regions 425
426 region 426
431 step of diving similar regions of one or more genome sequences into one or more segments 431
433 step of sorting and non-transitory storing of similar segments into similar repositories 433
435 similar segment 435
437 similar repository 437
440 anonymizing the one or more segments into one or more anonymized segments 440
450 non-transitory storing of one or more anonymized segments and/or one or more segments 450
500 method for saving storage space using anchor segments and reference segments 500
502 step of assigning one or more anchor segments 502
504 step of generating one or more referring segments 504
506 step of non-transitory storing of one or more anchor segments and one or more referring segments 506
508 step of anonymizing one or more referring segments into one or more anonymized referring segments 508
510 one or more anchor segments 510
512 calculated anchor segment 512
514 multiple anchor segment 514
518 one or more referring segments 518
521 first repository 521
522a second repository 522a
522b second repository 522b
522c second repository 522c
522d second repository 522d
530a genome sample 530a
530b genome sample 530b
532 one or more variations 532
533 single nucleotide polymorphism 533
534 insertion of two nucleotides 534
535 deletion of two nucleotides 535
536 replacement 536
540 method of using multiple anchor segments 540
542 step of subdividing two or more genome samples into two or more groups of segments 542
544 step of assigning anchor segment for each of the two or more groups of segments 544
546 step of generating a referring segment for each segment of the two or more groups of segments 546
548 step of non-transitory storing of each anchor segment in one or more of a same repository or a different repository 548

549 step of non-transitory storing of each referring segment in the repository that comprises the anchor segment used to generate that referring segment 549
560 method of using average anchor segments 560
561 step of designating at least two group leaders from a repository comprising two or more segments 561
562 step of forming at least two groups of segments, each group of segments is associated with each of the at least two group leaders 562
563 step of calculating for each group of segments an average anchor segment 563
564 step of ungrouping the at least two groups of segments into one larger group comprising the two more or segments and each of the average anchor segments 564
565 step of forming a new at least two groups of segments, each new group of segments is associated with each of the average anchor segments 565
566 step of calculating for each group of segments selected from the new at least two groups of segments a new average anchor segment 566
567 step of comparing the new average anchor segments against the average anchor segments 567
568 step of using the new average anchors segments and the new at least two groups of segments 568
600 linkage record 600
602 ID information ID 602
604 personal information ID 604
606 genome segment ID 606
608 phenotype ID 608
610 medical record ID 610
620 repeated information 620
622 ID information ID 622
624 personal information ID 624
626 genome segment ID 626
628 phenotype ID 628
630 medical record ID 630
640 statistical information 640
642 personal information 642
644 genome segments 644
646 phenotype 646
648 medical record 648
650 unique linkage record ID 650
700 computer system 700
702 processing unit(s) 702
704 input unit(s) 704
706 interconnection mechanism 706
708 storage unit(s) 708
710 output unit(s) 710
800 method for processing one or more genome sequences and associated information 800
802 step of receiving at least some original data as a record 802
804 step of organizing the at least some of the original data 804
805 step of dividing at least some of the original data 805
806 step of generalizing at least some of the original data 806
807 step of categorizing at least some of the original data 807
808 step of generating a linkage record 808
810 step of non-transitory storing of one or more of: at least some of the original data, organizational units, and/or linkage record 810
812 field 812
814 subfield 814
816 different-subfield 816
818 category 818
900 example of a genome wide association study (GWAS) record or other genetic study record 900
902 personal information 902
904 genome loci and/or variations information 904
906 phenotype information 906
908 medical records 908
1000 anonymized linkage record 1000
1002 anonymized ID information 1002
1004 anonymized personal information 1004
1006 modified genome segments 1006
1008 anonymized phenotypes 1008
1010 anonymized medical records 1010
1012 anonymized IDs 1012
1100 method for anonymizing a linkage record 1100
1104 step of modifying one or more genome sequences 1104
1106 step of finding or creating anonymized IDs 1106
1108 step of using linkage record to ID information that linkage record maps to 1108
1110 step of modifying the information to create anonymized information 1110
1112 step of assigning anonymized IDs to each created anonymized information 1112
1114 information 1114
1116 anonymized information 1116
1120 step of creating or updating anonymized linkage record 1120
1122 method for opting out of linkage record 1122
1124 step of receiving request to opt-out of linkage record 1124
1126 step of deleting linkage record 1126
1200 method for processing a request for genetic study results 1200
1200a method for processing a request for genetic study results 1200a
1200b method for processing a request for genetic study results 1200b
1202 receive the request for the genetic study results 1202
1204 find relevant records 1204
1206 group the relevant records into at least one group 1206
1206a group the relevant records into at least two separate groups 1206a
1206b group the relevant records into at least two groups of at least one control group and at least one experimental group 1206b
1208 anonymity check of the relevant records 1208
1210 anonymize the relevant records 1210
1212 provide anonymized information 1212
1214 method for processing a request for genetic study results 1214
1216 find and/or create linkage records for relevant segments 1216
1218 anonymize each relevant segment corresponding to the linkage record 1218
1220 provide the relevant segments that have anonymized in an aggregated group format of anonymized segments for one or more of the at least two separate groups 1220
1300 method for processing genetic study results 1300
1302 receiving genetic study results as received results 1302
1304 associating at least one marked allele with at least one relevant segment 1304
1306 cataloging received results 1306
1306a cataloging received results and/or cataloging association 1306a
1308 anonymity check 1308
1310 anonymizing received results 1310
1312 non-transitory storage of cataloged received results 1312

1312a non-transitory storage of cataloged received results and/or cataloged association 1312a
1314 method for processing genetic study results 1314
1400 method for generating personalized information of interest pertaining to at least one individual 1400
1402 method for generating personalized information of interest pertaining to at least one individual 1402
1403 method for generating personalized information of interest pertaining to at least one individual 1403
1404 method for generating personalized information of interest pertaining to at least one individual 1404
1406 additional steps 1406
1408 receive request for information of interest 1408
1410 is request sufficient 1410
1412 request additional information 1412
1414 receive additional information 1414
1416 is request anonymized 1416
1418 request anonymized format 1418
1420 receive anonymized request 1420
1422 anonymize request 1422
1424 pull pertinent records 1424
1426 filter pulled pertinent records 1426
1427 present pertinent records 1427
1428 present filtered pertinent records 1428
1430 identify at least one segment pertinent to pertinent segment 1430
1432 request sequence information (of at least one segment) 1432
1434 receive sequence information (of at least one segment) 1434
1436 narrow the pertinent records using the sequence information received to generate narrowed pertinent records 1436
1438 present narrowed pertinent records 1438
1440 is sequence information received sufficient 1440
1442 request additional sequence information 1442
1444 receive additional sequence information 1444
1446 is the sequence information received anonymous 1466
1448 request anonymized sequence information 1448
1450 receive anonymized sequence information 1450
1452 anonymize the sequence information received 1452
1454 optional steps 1454
1456 filter narrowed pertinent records 1456
1458 present filtered narrowed pertinent records 1458
1470 method for generating personalized information of interest pertaining to at least one individual 1470
1472 receive selection of one or more pulled pertinent records 1472
1474 filter selection 1474
1476 use associated information 1476
1482 retrieve at least one personalized recommendation 1482
1484 present at least one personalized recommendation 1484
1502 nucleotide sequence information 1502
1504 computing device 1504
1506 direct communication pathway 1506
1508 network 1508
1510 direct communication pathway 1510
1512 indirect communication pathway 1512
1514 indirect communication pathway 1514
1516 indirect communication pathway 1516

DETAILED DESCRIPTION OF THE INVENTION

Various methods and systems for processing at least some of one or more genome sequences and at least some of associated information, for at least one individual, may be described and disclosed herein. A purpose of such processing may be to prevent, minimize, and/or mitigate against identification of the at least one individual from the at least some of the one or more genome sequences and/or from associated information. For example, some such methods and/or systems may be compliant with HIPAA with respect to at least some biometric identifiers like genome sequence information. Another purpose of such processing may be to prevent, minimize, and/or mitigate against using the at least some of one or more genome sequences and/or associated information as a basis for discriminating against the individual. In some embodiments, such processing may comprise one or more of: (1) segmenting the at least some of one or more genome sequences for at least a purpose of anonymizing the at least some of one or more genome sequences; (2) using anchor segments for a purpose of minimizing storage space in storing of genetic sequence information; (3) generating at least one linkage record for accessing the at least some of one or more genome sequences and/or the at least some of associated information from storage, wherein the at least some of one or more genome sequences and/or the at least some of associated information may have been organized into various organizational units for storage in a manner that minimizes opportunity for identification and/or discrimination; (4) generating at least one anonymized linkage record, which may entail further processing (e.g., modifying and/or anonymizing) of at least some of the organizational units; (5) processing requests for genetic study results to be provided and providing those genetic study results in a manner that may not compromise anonymity; (6) processing genetic study results received; and/or (7) generating personalized information of interest pertaining to the individual pursuant to a request for such information.

In the following discussion that addresses a number of embodiments and applications of the present invention, reference is made to the accompanying drawings that form a part thereof, where depictions are made, by way of illustration, of specific embodiments in which the invention may be practiced. It is to be understood that other embodiments may be utilized and changes may be made without departing from the scope of the invention.

Specific embodiments of the invention will now be described in detail with reference to the accompanying figures. Like elements in the various figures are denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

Reference herein to "in some embodiments," "one embodiment," or "an embodiment" may mean that a particular element, feature, structure, or characteristic described in connection with the embodiment may be included in at least one embodiment of the invention. The appearances of the phrase "in one embodiment" in various places in the specification are not necessarily all referring to the same embodiment, nor are separate or alternative embodiments mutually exclusive of other embodiments. Further, the order of blocks in process flowcharts or diagrams representing one or more embodiments of the invention do not inherently indicate any particular order nor imply any limitations in the invention, unless otherwise explicitly noted.

Figure 1:
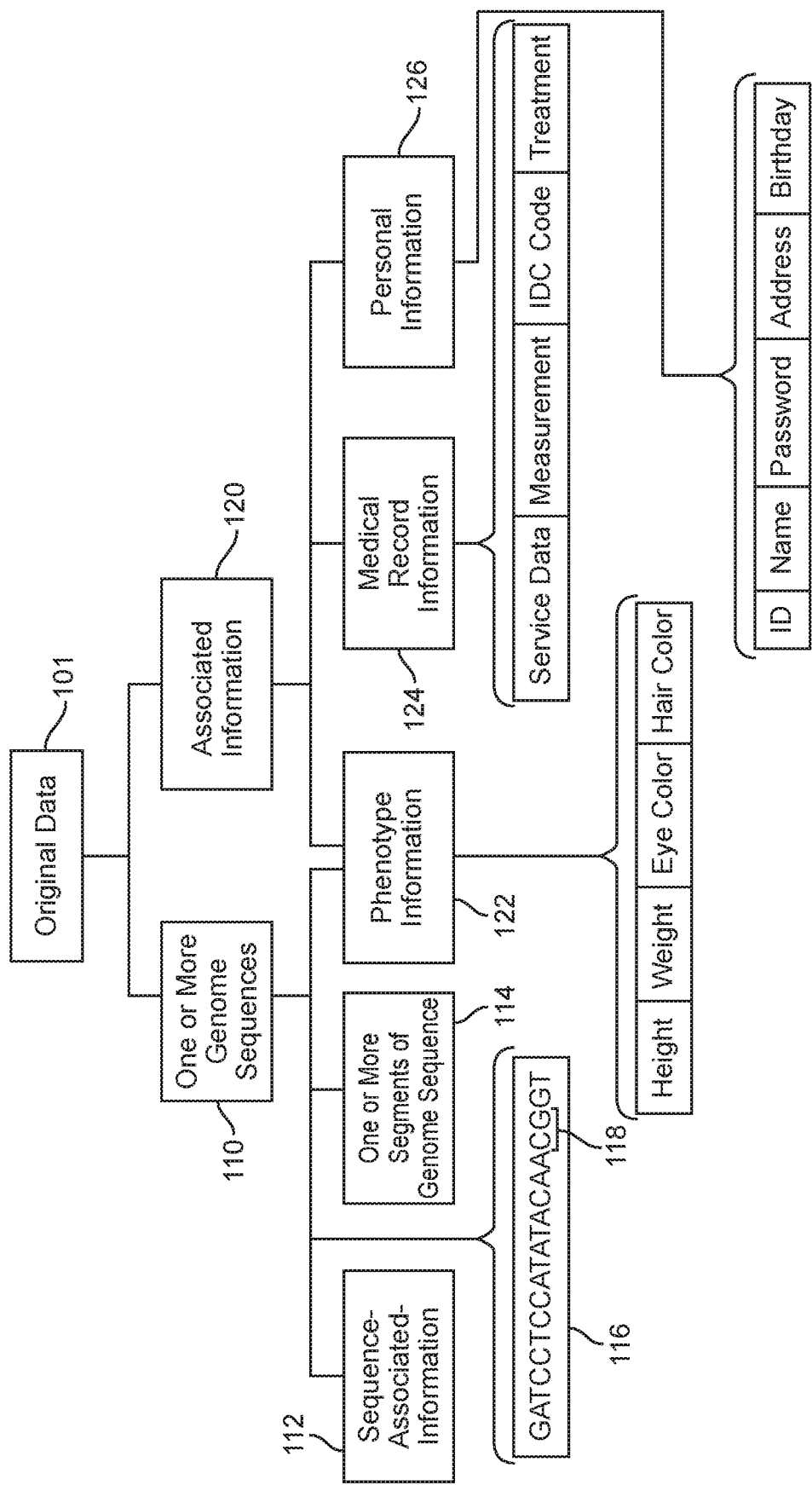
FIG. 1 may depict relationships between one or more genome sequences and associated information as depicted in a hierarchal organization chart.

Referring now to the drawings, in which like numerals may refer to like elements, features, structures, parts, and/or steps throughout the several views, FIG. 1 may depict relationships between one or more genome sequences 110 and associated information 120 as depicted in a hierarchal organization chart. FIG. 1 may depict an example of one or more genome sequences 110 and associated information 120 in accordance with one or more embodiments of the invention. In one embodiment, this example may be non-transitorily stored as an electrical record in a computer system (see e.g., FIG. 7) and/or in a data repository system (see e.g., FIG. 15). In some embodiments, both one or more genome sequences 110 and associated information 120 may be subsets of original data 101. In some embodiments, associated information 120 may be associated with one or more genome sequences 110. For example, and without limiting the scope of the present invention, where one or more genome sequences 110 may be sequence of nucleotides, associated information 120 may comprise phenotype information 122 deriving from that sequence of nucleotides. In some embodiments, one or more genome sequences 110 may comprise associated information 120. In some embodiments, one or more genome sequences 110 and associated information 120 may be different subsets of original data 101. See e.g., FIG. 1. In some embodiments, original data 101 may be indicative of the type of information and/or data that may comprise any given genetic study results record for a given individual, such as, but not limited to a genome-wide association studies (GWAS) study result record.

In some embodiments, one or more genome sequences 110 may comprise one or more segments 114 of genome sequence. See e.g., FIG. 1. Note, the language of "segment 114" may refer to nucleic acid sequence information for that given segment 114. That is, the language of "one or more segments 114 of nucleic acid sequences" may be substantially the equivalent to the language of "one or more segments 114." In some embodiments, one or more segments 114 may be derived and/or generated from one or more genome sequences 110. In some embodiments, a genome sequence 110 may comprise more nucleotides than a segment 114 may comprise. That is, a given genome sequence 110 may be larger (longer) than a given segment 114; although both may be comprised of nucleic acids. Also, note, many different types of segments 114 may be discussed herein, such as: anchor segments, referring segments, align segments, relevant segments, and/or the like and the reference numeral of "114" may be used with any such segment wherein the reference numeral of "114" may simply note that a segment may be what is being referred to, while leading adjectives (such as, but not limited to, anchor, average anchor, multiple anchor, calculated anchor, referring, align, relevant, and/or the like) may indicate the particular type of segment being discussed.

In some embodiments, one or more genome sequences 110 may comprise one or more sequences of nucleic acid. In some embodiments, the one or more genome sequences 110 may be specific unadulterated nucleic acid sequences for a given individual. In some embodiments, one or more genome sequences 110 may comprise sequences of one or more of: whole genomic DNA, partial genomic DNA, mtDNA (mitochondrial DNA), cDNA (complementary DNA), mRNA (messenger ribonucleic acid), RNA, protein amino acids, germ-line DNA, cancer cell DNA, cell-free DNA fragments, and/or the like. When one or more genome sequences 110 (or segments 114) may be referring to a sequence of DNA nucleotides, these DNA nucleotides may be expressed by letters of A (adenine), C (cytosine), G (guanine), and T (thymine). In some embodiments, one or more genome sequences 110 may comprise a DNA sequence 116 from the individual. See e.g., FIG. 1. In FIG. 1, DNA sequence 116 may be an example of a DNA sequence of nucleotides. In some embodiments, DNA sequence 116 may be illustrative of a DNA segment 114.

In certain embodiments of the invention, one or more genome sequences 110 to be processed and/or analyzed may be genomic DNA sequence information and its sequence-associated-information 112; however, persons of skill in the art will recognize that the invention may be practiced with respect to the sequencing results and/or their sequence-associated-information 112 from other forms of genetic material including, but not limited to, mtDNA, cDNA, mRNA, RNA, protein, germ-line DNA, cancer cell DNA, cell-free DNA fragments, and/or the like.

Note, some nucleotide sequence information contemplated by various embodiments of the present invention, including unadulterated, segmented, modified, and/or anonymized nucleotide sequence information of any sequence (e.g., one or more genome sequences 110) and/or of any segment 114 (e.g., one or more segments 114) may be non-transitorily stored, displayed, presented, and/or manipulated wherein the nucleotide sequence information may be in IUB/IUPAC nomenclature (abbreviations).

In some embodiments, one or more genome sequences 110 may comprise sequence-associated-information 112. See e.g., FIG. 1. In some embodiments, sequence-associated-information 112 may be information derived directly from a sequence of nucleotides of one or more genome sequences 110.

For example, and without limiting the scope of the present invention, in some embodiments, sequence-associated-information 112 may comprise information indicating at least one site in one or more genome sequences 110 for DNA methylation, such as a CpG site 118 for DNA methylation. See e.g., FIG. 1. In some embodiments, sequence-associated-information 112 may comprise information sufficient to determine at least some phenotype information 122. For example, and without limiting the scope of the present invention, sequence-associated-information 112 may comprise allele sequences coding for a plurality of amino acids that may form a particular protein, wherein presence of the particular protein may be indicative of some phenotype.

In some embodiments, associated information 120 may comprise one or more of: personal information 126, phenotype information 122, medical record information 124, and/or the like. See e.g., FIG. 1. In some embodiments, personal information 126 may comprise information about the given individual. In some embodiments, personal information 126 may comprise one or more of the following with respect to the individual: an ID and/or an identifier, a name (of the individual), a username, a password, an account, an address (e.g., a physical address), a date of birth, an age, at least one phone number, a fax number, at least one email address, a social security number, a driver license number, a medical record number, a profession, a hobby, a specialty, an interest, others who may access the account of the individual, family and/or friends of the individual, coworkers of the individual, and/or the like. In one embodiment, this ID may be used for the external submission of a record (which comprise original data 101 or some subset thereof) to an internal storage system. In another embodiment, this ID may be used to trace website activity after login.

In some embodiments, phenotype information 122 may be observable characteristics of the individual; that may result from an interaction of the individual's genotype with the environment. In some embodiments, phenotype information 122 may comprise one or more of the following of the individual: a height, a weight, eye color, hair color, a gender, a blood type, a disease, a genetic condition, a probability to develop some disease or some condition, and/or the like. See e.g., FIG. 1.

In some embodiments, medical record information 124 may comprise one or more of the following for the individual: a service date (e.g., a date of a medical examination and/or a date of some diagnostic test), a measurement (e.g., a vital sign measurement and/or some diagnostic test result), an IDC code (i.e., International Classification of Diseases code), or a treatment. See e.g., FIG. 1. In yet another embodiment, phenotype information 126 and medical record 124 may be combined as one set of information.

Figure 2:
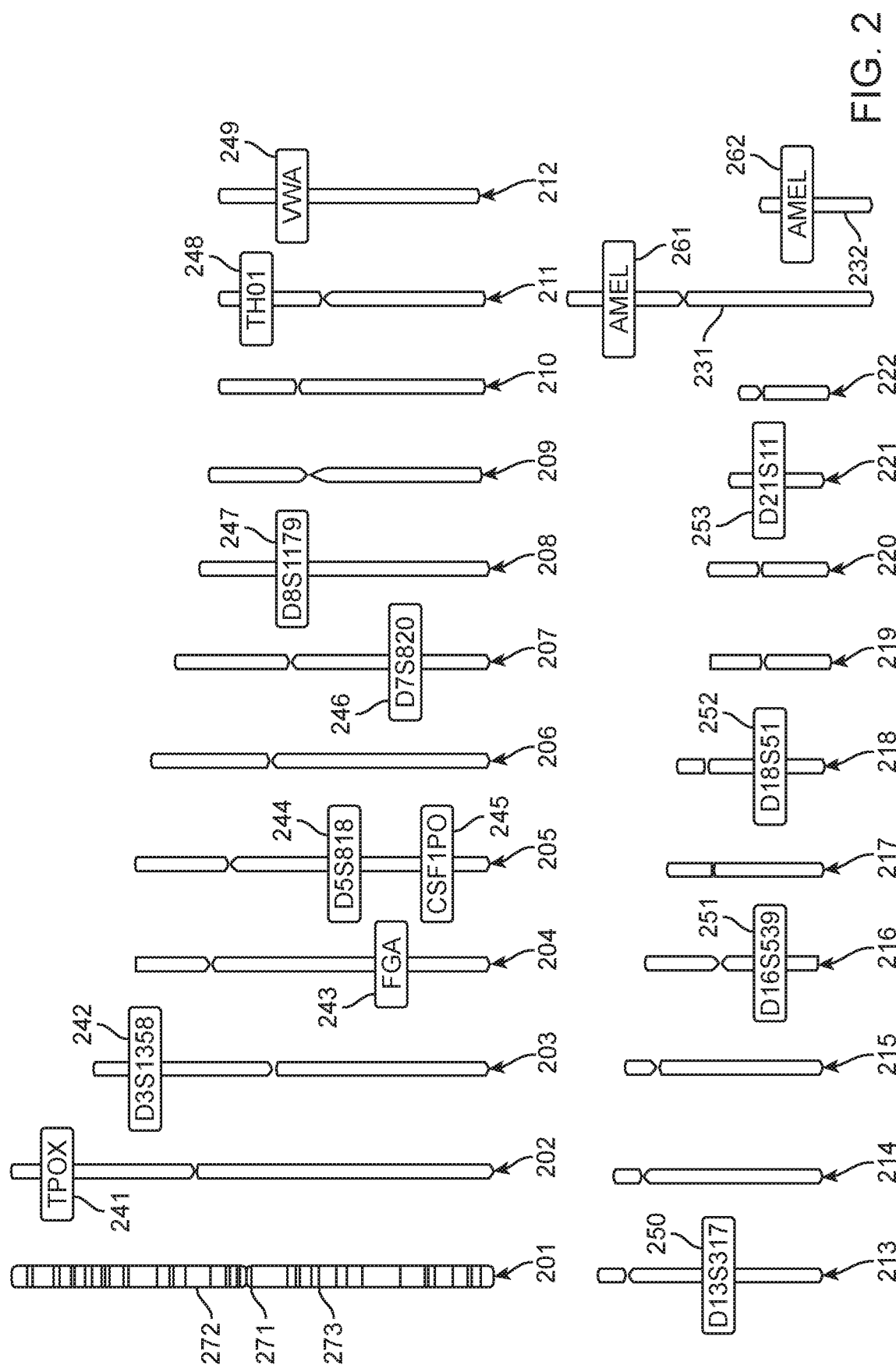
FIG. 2 may depict an example set of loci (e.g., CODIS loci) that may be used with DNA profiling to ascertain an identity of an individual comprising the example set of loci.

An individual's DNA sequences (and/or DNA segments; and/or other nucleic acid sequence information) may be used to identify (or re-identify) the individual. FIG. 2 and FIG. 3 may be depict an example of using the individual's DNA sequences to identify (or re-identify) the individual. FIG. 2 may depict an example set of loci (e.g., CODIS loci) that may be used with DNA profiling to ascertain an identity of the individual that may have this example set of loci. FIG. 3 may depict a follow-on example from FIG. 2, wherein allele frequency 304 for a subset of the set of loci may be used to calculate a final genotype frequency.

In FIG. 2 and FIG. 3, an example of Short Tandem Repeat (STR) polymorphisms may be employed to "DNA fingerprint" for a purpose of determining the identity of the individual. FIG. 2 may depict twenty-two human autosome chromatids 201 through and including 222, as well as two human allosome chromatids of 231 and 232. An ideogram of human autosome chromatid 201 may show a banding pattern of DNA loci in the genetic map wherein the loci may be divided into a short arm p 272 and a long arm q 273 by a centromere 271.

In FIG. 2 these STR loci may be TPDX 241, D3S1358 242, FGA 243, D5S818 244, CSF1PO 245, D7S820 246, D8S1179 247, THO1 248, VWA 249, D13S317 250, D16S539 251, D18S51 252, and D21S11 253 may be respectively located at: 2p25.3, 3p21.31, 4q28, 5q23.2, 5q33.1, 7q21.11, 8q24.13, 11p15.5, 12p13.31, 13q31.1, 16q24.1, 18q21.33, and 21q21.1. This set of 13 STR loci plus an Amelogenin (AMEL) locus 261 at the X chromatid 231 and the AMEL locus 262 at the Y chromatid 232 to determine sex; may together be utilized in Combined DNA Index Systems (CODIS) to identify individuals based on their STRs polymorphisms. Law enforcement, e.g., the US Federal Bureau of Investigation (FBI), may maintain DNA sequence databases for a purpose of identifying an individual from a set of submitted STR polymorphisms. FIG. 3 may demonstrate how a subset of such STR polymorphisms may be used to identify the individual.

As a lead in to FIG. 3, consider the human genome may contain approximately 3 billion base pairs (BP) wherein 99.9% of any individual human DNA is identical to DNA of others. Variations in DNA sequence between individuals are termed "polymorphisms." In particular, there are inherited regions of DNA with STR polymorphisms wherein STRs are normally of length 2-5 base pairs of repeated DNA sequence in a head-tail manner. For example, the STR for the D5S818 locus 244 may be "AGAT" and a 20 BP sequence of "AGATAGATAGATAGATAGAT" may represent 5 head-tail copies of the tetramer "AGAT." Different alleles of this D5S818 locus 244 may have from 7 to 15 tandem repeats of the "AGAT" sequence in a given set of samples with observed tandem repeats to form allele frequencies. If an individual is homozygous for a particular allele with a frequency of p, the probability of the genotype is p multiplied by p (or p squared); and if the individual is heterozygous for one particular allele with a frequency of p and another allele with a frequency of q, the probability of the genotype is 2 multiplied by p multiplied by q.

FIG. 3 may depict an example of an individual with a certain set of DNA markers 302 corresponding to allele frequencies 304 and with resulting genotype frequencies 306. In this example, the homozygous TPDX locus 310 of 8 tandem repeats of the "AATG" sequence has 189 observed instances in 1000 samples with 0.189 as its allele frequency 304 and 0.036 as its genotype frequency 306. In this same example, the heterozygous VWA locus 320 of 15 and 16 tandem repeats of the "TCTA" with "TCTG" and "TCCA" inserts has 127 and 131 observed instances in 1000 samples with 0.127 and 0.131 as the allele frequencies 304, respectively; and 0.033 as the genotype frequency 306. A total probability 330, $5.8 \times 10^{-8}$, for this set of DNA markers 302 is the product of the genotype frequencies 306. This FIG. 3 example illustrates that a random match probability or the chance of a random match has been reduced tremendously through use of statistical product rule to calculate the total probability 330. A greater a rarity of a given total probability 330 as compared against a particular population size, the more likely of being able to identify the individual associated with the given polymorphism data. This is one way an individual's DNA sequence information may be a biometric identifier. Additionally, an individual's DNA sequence information may also convey sequence-associated-information 112, phenotype information 122, and/or may be associated with associated information 120, anyone of which may be used to identify the individual or convey information of a private nature that could be abused and/or used to discriminate against the individual. Various embodiments of the present invention may manipulate, process, modify, and/or anonymize such original data 101 (or subsets thereof) to mitigate against: identifying the individual, having data which may be abused, and/or having data which may permit the individual to be discriminated against. Some embodiments of the present invention may take received one or more genome sequences 110 and/or associated information 120 and segment one or more genome sequences 110 into segments with adjustable linkage records 600 so as to statistically manage these risks, such as the risk of re-identifying the individual.

The FIG. 4 series of figures may comprise FIG. 4A through and including FIG. 4E. These FIG. 4 series of figures may address a process of segmenting one or more genome sequences 110 into one or more segments 114, such as, disjoint segments 406 and/or overlapping segments 407.

In some embodiments, at least one of method 400 (see FIG. 4A) goals may be to return to a requestor a minimal amount of nucleic acid sequence information (i.e., the one or more segments 114), that may only be relevant to particular genome information being inquired about. Conversely, the more nucleic acid sequence information returned to the requestor, the more likely the identity of the person associated with that nucleic acid sequence can be determined; or that the requestor (or some other party) could abuse the returned nucleic acid sequence information (e.g., by breaching an individual's privacy rights); or that the requestor (or some other party) could use the returned nucleic acid sequence information in a discriminatory manner. For example, and without limiting the scope of the present invention, if a request comprises a whole genome sequence, but the request also comprises requesting information relating to a limited number of alleles and/or loci, then the method and/or system may only return one or more segments 114 (as well as relevant associated information 120 or subsets thereof) that may "match" the request by being relevant to the alleles and/or loci identified in the request; and not return the whole genome sequence.

FIG. 4A may depict a flow diagram of exemplary steps for the process of segmenting the one or more genome sequences 110 into the one or more segments 114, such as, disjoint segments 406 and/or overlapping segments 407. In some embodiments, FIG. 4A may depict steps in various embodiments of method 400. In some embodiments, method 400 may be a method for segmenting one or more genome sequences for at least a purpose of anonymizing at least some genome information of the one or more genome sequences 110; which once anonymized may be used in a safer manner with respect to the individual and complying with privacy laws, such as HIPAA. In some embodiments, method 400 may comprise steps: step 402, step 405, and step 440. In some embodiments, method 400 may comprise steps: step 402, step 405, step 410, and step 440. In some embodiments, method 400 may comprise steps: step 402, step 405, step 440, and step 450. In some embodiments, method 400 may comprise steps: step 402, step 405, step 410, step 440, and step 450. In some embodiments, step 410 may feed into step 405. In some embodiments, step 440 may progress into step 450. That is, in some embodiments of method 400, step 410 may be optional. That is, in some embodiments of method 400, step 450 may be optional.

In some embodiments, step 402 may comprise receiving one or more genome sequences 110. In some embodiments, one or more genome sequences 110 may be received as electrical records and/or digital records. In some embodiments, one or more genome sequences 110 may be received as physical DNA samples which may then be sequenced into electrical records and/or digital records. See FIG. 4A.

In some embodiments, step 402 of receiving one or more genome sequences 110, may further comprise receiving one or more of associated information 120 and/or sequence-associated-information 112. See FIG. 4A. In some embodiments, associated information 120 may be associated with the one or more genome sequences 110. In some embodiments, sequence-associated-information 112 may be information derived directly from a sequence of the one or more genome sequences 110. For example, and without limiting the scope of the present invention, sequence-associated-information 112 may include such information that a certain disease, a genetic condition, or a probability to develop some disease or some condition may statistically associate with that sequence at some probability (i.e., some percentage of association). That probability may be low or high or in between. For any given segment 114, there could be sequence-associated-information 112 that may comprise a patient's risk of disease, average risk of disease, and confidence in disease study associated with that segment 114. For example, and without limiting the scope of the present invention, in some embodiments, sequence-associated-information 112 may comprise information indicating at least one site in one or more genome sequences 110 for DNA methylation, such as CpG site 118 (see e.g., FIG. 1). For example, and without limiting the scope of the present invention, in some embodiments, sequence-associated-information 112 may comprise information indicating CpG sites (CpG Islands), such as CpG site 118. For example, and without limiting the scope of the present invention, in some embodiments, sequence-associated-information 112 may comprise information sufficient to determine at least some phenotype information 122. For example, and without limiting the scope of the present invention, sequence-associated-information 112 may comprise allele sequences coding for a plurality of amino acid that may form a particular protein.

In some embodiments, the method(s) and/or the system(s) upon receiving a request of a specific nucleic acid sequence or upon receiving a request for at least some genome information that is associated with the specific nucleic acid sequence, may comprise the method(s) and/or the system(s) searching one or more storage units 708 for one or more segments 114 (which may be one or more anonymized segments) that may substantially match the specific nucleic acid sequence according to a predetermined threshold. For example, and without limiting the scope of the present invention, this predetermined threshold may be some predetermined percentage of likeness between the specific nucleic acid sequence in the request and one or more segments 114 (which may be one or more anonymized segments). In some embodiments, the method(s) and/or the system(s) may further comprise providing access to one or more segments 114 one or more segments 114 (which may be one or more anonymized segments) that may substantially match the specific nucleic acid sequence according to the predetermined threshold.

In some embodiments, step 405 may comprise segmenting the received one or more genome sequences 110 into one or more segments of nucleic acid sequences 114. See FIG. 4A. Note segments of nucleic acid sequences 114 may be referred to as "segments 114." So the one or more segments of nucleic acid sequences 114 may be referred to as one or more segments 114. Such segments 114 may refer to physical segments of nucleic acids and/or to sequence information of the nucleic acids. Likewise, this sequence information for any given segment 114 may stored as a physical segment of nucleic acid and/or preferably non-transitorily stored as electrical records and/or digital records. Also as shown in FIG. 4B and as is discussed below in the FIG. 4B discussion, segments 114 that the segmenting step 405 may produce may be disjoint segments 406 and/or overlapping segments 407.

In some embodiments, the step 405 of segmenting the one or more genome sequences 110, may further comprise a step of organizing one or more of the associated information 110 and/or of organizing sequence-associated-information 112. An output of such organizing may be organizational units. In some embodiments, such organizational units may be produced by one or more of: dividing and/or generalizing associated information 110. In some embodiments, such organizational units may be produced by one or more of: dividing and/or generalizing sequence-associated-information 112. In some embodiments, at least one such organizational unit may be associated with at least one of one or more segments 114. In some embodiments, such organizational units may be electronic records and/or digital records. In some embodiments, such organizational units may non-transitory stored in one or more storage units 708 (see FIG. 7 for one or more storage units 708).

Continuing discussing FIG. 4A, in some embodiments, step 410 may aid in the segmenting step 405. In some embodiments, step 410 may comprise using one or more align sequences 420 (or one or more align segments) to aid in the segmenting step 405. FIG. 4C, FIG. 4D, and FIG. 4E and their corresponding figure discussions (see below) go into more details regarding using one or more align sequences 420 (or one or more align segments) to aid in the segmenting step 405.

Continuing discussing FIG. 4A, in some embodiments, step 440 may comprise anonymizing the one or more segments 114 produced from step 405 into one or more anonymized segments. In some embodiments, the step 440 of anonymizing of the one or more segments 114 to produce the one or more anonymized segments may comprise one or more of the following: deleting, inserting, appending, and/or replacing some sequence information of the one or more segments 114.

In some embodiments, step 440 may progress into step 450. See e.g., FIG. 4A. In some embodiments, the one or more anonymized segments may be electronic records and/or digital records. In some embodiments, one or more segments 114 may be electronic records and/or digital records. In some embodiments, step 450 may comprise non-transitory storing of the one or more anonymized segments; and/or non-transitory storing of the one or more segments 114. Such storage may be in one or more storage units 708 (see FIG. 7 for one or more storage units 708).

FIG. 4B may depict a representation of an output of step 405, of segmenting one or more genome sequences 110 into one or more segments 114, such as, disjoint segments 406 and/or overlapping segments 407.

In some embodiments, the one or more segments 114 (e.g., produced by step 405) may comprise two or more segments of nucleic acid sequences (i.e., two or more segments). That is, the process of segmenting one genome sequence 110 must produce at least two segments 114. Although, in some application of various method and/or system embodiments, not all produced segments 114 may be utilized, stored, indexed, and/or kept. In some embodiments, the step 405 of segmenting the one or more genome sequences 110 may be done by producing the one or more segments 114 as one or more of disjoint segments 406 and/or overlapping segments 407. See e.g., FIG. 4B. In some embodiments, disjoint segments 406 may be produced from a disjoint fashion segmenting. In some embodiments, overlapping segments 407 may be produced from overlapping segmenting, i.e., wherein segmenting may be carried out in an overlapping fashion. In the overlapping fashion the two or more segments 407 may overlap each other such that the two or more segments share sequences of overlap 408. See FIG. 4B. In some embodiments, disjoint segments 406 may be produced from disjoint segmenting, i.e., wherein segmenting may be carried out in a disjoint fashion, such that where one segment 406 ends, another segment 406 begins. In the disjoint fashion there are no sequences of overlap 408 between segments 406.

In FIG. 4B one or more genome sequences 110 may be segmented into segments (e.g., disjoint segments 406 and overlapping segments 407). In one embodiment, such segments may be disjoint segments 406 and in another embodiment, two or more overlapping segments 407 may be by region of overlap 408. With overlapping segments 407, one such segment may partially or completely overlap (cover) another segment or many other segments.

In some embodiments, one or more segments 114 may be of lengths of one or more of: fixed-length (i.e., a fixed number of nucleotides) and/or variable-length (i.e., a variable number of nucleotides).

The process of segmenting one or more genome sequences 110 into one or more segments 114 may involve at least two problems, that of where to segment and that of how to segment. FIG. 4C and FIG. 4D which may address utilization of one or more align sequences 420 (or one or more align segments) may focus more on the how to segment; and FIG. 4E may focus more on the where to segment issue.

FIG. 4C may depict a flow diagram of exemplary steps for a process of using one or more align sequences 420 (or one or more align segments) to aid in the segmenting process. FIG. 4C may depict steps for step 410, where step 410 may have been used in method 400 of FIG. 4A. That is, step 410 may be method 410, a method of using one or more align sequences 420 (or one or more align segments) to aid in the segmenting. In some embodiments, method 410 may comprise step 412, step 425, and step 431. In some embodiments, method 410 may comprise step 412, step 425, step 431, and step 433. In some embodiments, step 433 may be optional.

In some embodiments, step 412 may comprise finding and/or creating one or more align sequences 420 from at least one whole genome sequence 110. See FIG. 4C. In some embodiments, a given align sequence 420 may be created based off less than the at least one whole genome sequence 110, such as, but not limited to, a given chromosome or a given chromatid. FIG. 4E may expand upon step 412 in how one or more align sequences 420 may be found and/or created.

Continuing discussing FIG. 4C, in some embodiments, step 425 may comprise aligning regions 426 of similar nucleotide sequences in the one or more align sequences 420 with regions of similar nucleotide sequences in the one more genome sequences 110. (Note, see FIG. 4D for align sequence 420 and regions 426.) Continuing discussing FIG. 4C, in some embodiments, aligning regions of similar nucleotides may further comprise aligning regions of complimentary nucleotide sequences. For example, and without limiting the scope of the present invention, this may be desirable or necessary when the complimentary nucleotide sequence may comprise a variation or polymorphism. In some embodiments, segmenting to produce segments 114 may be proceeded by use of align sequences 420. That is, at least some sequence information in an align sequence 420 may be aligned with similar sequences in the one or more genome sequences 110 that the method or system contemplates segmenting. That is, step 410 may aid in step 405.

In some embodiments, step 431 may comprise dividing the one or more genome sequences 110 into the one or more segments 114 by cutting at boundaries of each of the regions of similar nucleotide sequences in the one more genome sequences 110 that may be aligned with regions 426 of the one or more align sequences 420. See e.g., FIG. 4C.

In some embodiments, step 433 may comprise sorting similar segments 435 and/or non-transitory storing of similar segments 435 into similar repositories 437. In some embodiments, one or more segments 114 may be non-transitorily stored in repositories 437. In some embodiments, each such repository 437 selected from the repositories 437 may non-transitorily store similar segments 435 produced from similar regions. See e.g., FIG. 4C. (Note, see FIG. 4D for similar segments 435 and similar repositories 437.)

FIG. 4D may depict a representation of segmenting at least three genome sequences (110a, 110b, and 110c), using align sequence 420, and how resulting similar segments 435 may be grouped together and non-transitorily stored in like grouped similar repositories 437.

FIG. 4D may depict mechanics and outputs of step 425, flowing into step 431, and culminating with step 433. In step 425 regions of three genome sequences (110a, 110b, and 110c) may be aligned with similar (matching) regions of align sequence 420. In this example, align sequence 420 may comprise three distinct regions ($426_1$, $426_2$, and $426_3$). Note, in FIG. 4D, these three distinct regions (e.g., $426_1$, $426_2$, and $426_3$) may be disjoint with some gap of nucleotides between regions; however, it may be that such distinct regions may be one or more of: disjoint with gap(s), without gap(s), overlapping, and/or combinations thereof. Recall e.g., FIG. 4B and its discussion. Note, genome sequence 110a may comprise similar matching regions that may correspond to region $426_1$ and region $426_2$; but not region $426_3$. Similarly, genome sequence 110b may comprise similar matching regions that may correspond to region $426_1$ and region $426_2$; but not region $426_3$. However, genome sequence 110c may comprise similar matching regions that may correspond to region $426_2$ and region $426_3$; but not region $426_1$. That is, as shown in FIG. 4D, each such genome sequence 110 (110a, 110b, and 110c) may be missing sequences that may match one of the regions of align sequence 420; however, in other examples, any given such genome sequence 110 may comprise all such regions of a given align sequence 420; or any given genome sequence 110 may only comprise just one such sequence that may match a given region of the given align sequence 420. Thus in the FIG. 4D example there may be two separate regions of genome sequences 110 that correspond to region $426_1$ (one from genome sequence 110a and one from genome sequence 110b); there may be three separate regions of genome sequences 110 that correspond to region $426_2$ (one from genome sequence 110a, one from genome sequence 110b, and one from genome sequence 110c); and there may be one separate region of genome sequence 110 that corresponds to region $426_3$ (one from genome sequence 110c). Thus, an output of step 425 may be genome sequences 110 with regions that have been aligned with regions 426 in one or more align sequences 420; based upon similarity in the corresponding regions. See e.g., FIG. 4D. Note, in FIG. 4D these genome sequences (110a, 110b, and 110c) may be from the same individual or different individuals.

In some embodiments, once step 425 has aligned the regions of genome sequences 110 with regions 426 in one or more align sequences 420, then step 431 may proceed with dividing (e.g., cutting) at the boundaries of these regions in genome sequences 110 to produce one or more segments 114. In FIG. 4D, these segments 114 may be denoted as similar segments 435, such as similar segment $435_1$, similar segment $435_2$, and similar segment $435_3$; wherein the subscript corresponds to the similar of regions 426. Thus in the FIG. 4D example there may be two separate similar segments $435_1$ of genome sequences 110 that correspond to region $426_1$ (one from genome sequence 110a and one from genome sequence 110b); there may be three separate similar segments $435_2$ of genome sequences 110 that correspond to region $426_2$ (one from genome sequence 110a, one from genome sequence 110b, and one from genome sequence 110c); and there may be one separate similar segment $435_3$ from genome sequence 110c that corresponds to region $426_3$.

Then in step 433, each of these similar segments 435 may be stored in separate, but similar repositories 437. In some embodiments, the storage step of step 433 may also be a sorting step, i.e., similar segments 435 may be sorted into similar repositories 437. In some embodiments, similar segments 435 may be electronic records and/or digital records. In some embodiments, storage of similar segments 435 into similar repositories 437 may be non-transitory storage. In some embodiments, one or more storage units 708 may comprise similar repositories 437. In some embodiments, a single storage unit 708 may comprise a plurality of similar repositories 437. In some embodiments, the plurality of similar repositories 437 may or may not involve use of partitioning the single storage unit 708.

In some embodiments, one or more align sequences 420 may be electronic records and/or digital records. In some embodiments, one or more align sequences 420 may be non-transitorily stored within one or more storage units 708.

FIG. 4E may depict a schematic for finding and/or creating the one or more align sequences 420 from a genome sequence 110. Note, a given one or more genome sequences 110 that may be used to produce (generate) one or more align sequences 420 pursuant to step 412, may not be the same one or more genome sequences 110 that the produced (generated) one or more align sequences 420 then operates upon in steps 425 and/or in step 431. Also note, once a given one or more align sequence 420 may have been produced (generated), its sequence and/or length may define the boundaries of where the similar (matching) regions of one or more genome sequences 110 may be divided to produce one or more segments 114 (or similar segments 435). Thus the given align sequence 420 may determine the how and/or the where of dividing one or more genome sequences 110. And thus, it may be critical to determine how a given align sequence's 420 sequence and/or length may be determined.

In some embodiments, creating one or more align sequences 420 may comprise processing at least one whole genome sequence 110 into one or more align sequences 420. See FIG. 4E. In some embodiments, such processing may involve marking and/or cutting a specific locus. In some embodiments, such loci may be determined from one or more of: genetic map information 414, GWAS information 416, polymerase chain reaction (PCR) information, sequence-associated-information 112, non-GWAS research involving segments 114, medical expertise, genetic expertise, and/or the like. In some embodiments, such processing may comprise marking and/or cutting using genetic map information 414 to mark and/or cut at least one whole genome sequence 110 into one or more of sequences of genes, sequences for controlling gene expression, and/or regions of overlap 408. See e.g., FIG. 4E. In some embodiments, such processing may comprise marking and/or cutting using genetic map information 414 to mark and/or cut at least one whole genome sequence 110 into one or more align sequences 420. In some embodiments, such processing may comprise marking and/or cutting using the genetic map to mark and/or cutout one or more of non-gene sequences and/or sequences that do not control for gene expression. In some embodiments, a product of processing at least one whole genome sequence 110 by using genetic map information 414 may be one or more align sequences 420; which in some embodiments, may comprise the one or more of sequences of genes and/or the sequences for controlling gene expression; and in other embodiments may not comprise the one or more of sequences of genes nor the sequences for controlling gene expression.

In some embodiments, cutting may be a subset of marking. In some embodiments, marking may comprise cutting. Marking of physical nucleic acid sequences may involve attaching various tags to specific sequences or to attaching tags to specific nucleotides at specific loci; wherein such tag locations may be determined from some spectroscopic means, e.g., because the tag may comprise a radioisotope or some other indicator (e.g., a dye). Marking of electronic record and/or digital record nucleic acid sequences may involve attaching a digital tag and/or annotation to the record indicating the marking of a specific locus. In some embodiments, cutting may be applied to either physical nucleic acid sequences and/or to electronic record and/or digital record nucleic acid sequences. In some embodiments, a given align sequence 420 may be marked, but not cut, as leaving the given align sequence 420 intact may facilitate using that given align sequence 420 in segmenting other one or more genome sequences 110.

In some embodiments, one or more align sequences 420 may comprise one or more of sequences of genes and/or sequences for controlling gene expression. In some embodiments, one or more align sequences 420 may comprise further processing of one or more of the sequences of genes and/or the sequences for controlling gene expression. In some embodiments, one or more of the sequences of genes and/or the sequences for controlling gene expression may be further processed by further marking and/or cutting utilizing GWAS results 416 and/or other research information. See e.g., FIG. 4E.

In some embodiments, creating one or more align sequences 420 may comprise processing at least one whole genome sequence 110 into one or more align sequences 420. See FIG. 4E. In some embodiments, such processing may comprise marking and/or cutting utilizing GWAS results 416 to mark and/or cut at least one whole genome sequence 110 into one or more align sequences 420. For example, and without limiting the scope of the present invention, a given align sequence 420 may be created without initially marking and/or cutting by using genetic map processing 414, as noted in FIG. 4E, but instead may be processed (marked and/or cut) using GWAS results 416. See e.g., FIG. 4E.

In some embodiments, determining where to segment (divide) one or more genome sequences 110 to produce one or more segments 114, may not involve use of one or more align sequences 420. For example, and without limiting the scope of the present invention, the step of segmenting the one or more genome sequences 110 into the one or more segments 114 (such as in step 405) may comprise a step of determining loci in one or more genome sequences 110 of where to divide (segment). In some embodiments, these loci may be determined from one or more of: genetic map information, GWAS information, PCR information, sequence-associated-information 112, non-GWAS research involving segments 114, medical expertise, genetic expertise, and/or the like. For example, and without limiting the scope of the present invention, medical expertise may comprise applications of personalized medicine. For example, and without limiting the scope of the present invention, sequence-associated-information 112 may comprise information that a certain disease associates with given sequence information at some percentage and that given sequence information may determine where to divide or where not to divide, e.g., it may be desirable to not divide that given sequence information 112.

In one embodiment, dividing (segmenting) may utilize information from the genetic map. In another embodiment, dividing may utilize information from the GWAS. In another embodiment, dividing may utilize information from the study of the genetic markers. In another embodiment, dividing may utilize information from PCR. In yet another embodiment, the segments 114 may be fixed-length and/or variable-length; as may be specified by the storage system. However, persons of skill in the art will recognize that the invention may be practiced with respect to other artificial or genetic types of dividing methods to divide portion(s) of genome sequence 110 or whole genome sequence 110 into resulting segments 114. In one embodiment, a set of segments 114 may be further divided or merged in order to manage the risk of re-identifying an individual.

The FIG. 5 series of figures may comprise FIG. 5A through and including FIG. 5E. These FIG. 5 series of figures may address a process of using anchor segments 510 and referring segments 518 for at least a purpose of minimizing storage space as related to non-transitory storing of sequence information of segments 114 and/or of sequence information of one or more genome sequences 110.

FIG. 5A may depict a flow diagram of exemplary steps for the process of using anchor segments 510 and referring segments 518 to minimize storage space. (See FIG. 5B for anchor segments 510 and referring segments 518.) FIG. 5B may depict storage savings results from three different examples of utilizing anchor segments 510 and referring segments 518 to minimize storage space. In FIG. 5B, a transition from first repository 521 to second repository 522b may be representative of method 500 and/or of at least some of the steps of FIG. 5A. In FIG. 5B, a transition from first repository 521 to second repository 522c (and to second repository 522d, in some embodiments) may be representative of method 540 and/or of at least some of the steps of FIG. 5D. In FIG. 5B, a transition from first repository 521 to second repository 522a may be representative of method 560 and/or of at least some of the steps of FIG. 5E. In some embodiments, the at least some of the steps of FIG. 5E may result in more than one anchor segments 510.

Although steps, methods, and/or examples depicted FIG. 5A through FIG. 5E may be used to save storage space; such steps and/or method may also be used to measure diversity of received sequence samples; wherein each anchor segment 510 may represent a cluster of segments 114 and a number of anchor segments 510 may serve as an indicator of the diversity of a given set of sequences. Furthermore, the variations of the closest anchor segment 510 for a new sequence and/or segment 114 may be an indicator of novelty of the new sequence and/or segment 114 for an existing set of sequence samples.

FIG. 5A may depict exemplary steps for method 500. In some embodiments, method 500 may be a method for using one or more anchor segments 510 for a purpose of minimizing storage space. In some embodiments, method 500 may comprise step 502, step 504, and step 506. In some embodiments, method 500 may comprise step 502, step 504, step 506, and step 508.

In some embodiments, step 502 of FIG. 5A may comprise assigning one or more anchor segments 510 by using one or more genome samples as a basis for one or more of generating, deriving, computing, calculating, or determining one or more anchor segments 510. In some embodiments, method 500 for using one or more anchor segments 510 for at least a purpose of saving storage space may be with respect to non-transitory storing of sequence information of segments 114 and/or of segments 435 as may have been produced from the segmenting process, such as segmenting method 400 (or step 405 and/or step 410) as noted in the FIG. 4 series of figures and as discussed above in the FIG. 4 series of figures discussion. That is, segments 114 and/or similar segments 435 may be converted into (and/or non-transitorily saved as) referring segments 518 and/or into anchor segments 510.

In some embodiments, step 502 of FIG. 5A of assigning may comprise selecting the one or more anchor segments 510 by using one or more genome samples as a basis (e.g., foundation) for one or more of: generating, deriving, computing, calculating, and/or determining one or more anchor segments 510. That is, a given anchor segment 510 may be derivative of the one or more genome samples. See e.g., FIG. 5B, first repository 521 which may comprise six genome samples as segments 114 each of five nucleotides in length; wherein these six segments 114 may be the one more genome samples examples in FIG. 5B. In FIG. 5B, these six genome samples in first repository 521 may be labeled (1) through (6), and each capital letter of A, T, C, and G may be representative of the four standard DNA nucleotide base pairs. In this FIG. 5B example, because each of these six genome samples may be five nucleotides in length, a total data storage load (or data storage burden) may be that of 30 (i.e., five times six). Such a resulting anchor segment 510 from generating, deriving, computing, and/or calculating may or may not reflect full sequence information of any actual segment 114 in storage in one or more storage units 708, a database, and/or in repositories (e.g., similar repositories 437). For example, and without limiting the scope of the present invention, calculated anchor segment 512 residing in second repository 522a in FIG. 5B may be a calculated anchor segment that does not reflect actual sequence information for any of segments 114 of the one or more genome samples stored in first repository 521 in FIG. 5B. That is, calculated anchor segment 512 example in FIG. 5B of "TTGCG" is not a sequence represented in first repository 521; because calculated anchor segment 512 may have been generated, derived, computed, and/or calculated from one or more of the genome samples of first repository 521. Note, when in the FIG. 5B example, with calculated anchor segment 512 may be "TTGCG" then the total data storage load of second repository 522a may be 16, which represents a data storage savings of 14 as compared to first repository 521 with its total data storage load of 30.

In some embodiments, calculated anchor segment 512 and/or multiple anchor segments 514 may be subsets of anchor segment 510. In some embodiments, anchor segment 510 may comprise calculated anchor segment 512 and/or multiple anchor segments 514. In some embodiments, an average anchor segment may be an example of calculated anchor segment 512. In some embodiments, calculated anchor segment 512 may comprise the average anchor segment.

In some embodiments, determining the given anchor segment 510 may involve using a predetermined sequence as the given anchor segment 510. In some embodiments, the predetermined sequence may be any known sequence of nucleotides, that may be known in advance to assigning the given anchor segment 510. In some embodiments, the predetermined sequence may be a given align sequence 420 (or a given align segment). In some embodiments, determining the given anchor segment 510 may involve using a segment 114 already in storage, in which case the given anchor segment 510 may reflect full sequence information of that given actual segment 114 in storage in one or more storage units 708, a database, and/or in repositories (e.g., similar repositories 437). For example, and without limiting the scope of the present invention, anchor segment 510 within second repository 522b in FIG. 5B may reflect the actual sequence information of the first segment 114 of "AAGTG" within first repository 521 in FIG. 5B. Note, when in the FIG. 5B example, with anchor segment 510 may be "AAGTG" then the total data storage load of second repository 522b may be 20, which represents a data storage savings of 10 as compared to first repository 521 with its total data storage load of 30.

In some embodiments, one or more anchor segments 510 may be an anchor sequence. In some embodiments, the anchor sequence may be segmented (divided) to produce one or more anchor segments 510, according to at least one segmenting embodiment as discussed above in the FIG. 4 series discussion.

In some embodiments, step 504 of FIG. 5A may comprise generating one or more referring segments 518. In some embodiments, a given referring segment 518 selected from one or more referring segments 518 may be one or more variations between a given anchor segment 510 selected from the one or more anchor segments 510 and a genome sample selected from the one or more genome samples; such that by using the referring segment 518 together with the given anchor segment 510, full sequence information of the genome sample may be known; but, without having to store that full sequence information of the genome sample, which then may save storage space. That is, the full sequence information of the genome sample used to generate the referring segment 518, may be reconstructed from the referring segment 518 and the relevant anchor segment 510. For example, in FIG. 5B, consider first repository 521 and second repository 522b; where anchor segment 510 in second repository 522b may be "AAGTG" which is also the first (1) genome sample segment 114 in first repository 521; wherein a first referring segment 518 in second repository 522b, which may be denoted with (2), and has variation sequence of "_ _ _ C _"; wherein each blank denotes no variation as between the given referring segment 518 with respect to a given anchor segment 510; such that when "_ _ _ C _" is combined with "AAGTG", then the entire sequence information of "AAGCG" of the second genome sample (2) in first repository 521 may be determined.

For example, and without limiting the scope of the present invention, in situations where there may be no variations between the given anchor segment 510 and one of the one or more genome samples, then the referring segment 518 may just be that given anchor segment 510.

For example, and without limiting the scope of the present invention, in FIG. 5B, from each group of referring segments 518 and its corresponding anchor segment (e.g., 510, 512, and 514) in a given second repository (e.g., 522a, 522b, and 522c together with 522d) the full sequence information of the six segments 114 of the one or genome samples in the first repository 521 may be determined by combining the relevant referring segment 518 with its appropriate anchor segment (e.g., 510, 512, and 514).

In some embodiments, step 506 of FIG. 5A may comprise non-transitorily storing the one or more anchor segments 510 and/or one or more referring segments 518 in one or more of: one or more storage units 708, a database, and/or in repositories (e.g., similar repositories 437); which may save storage space as compared to storing full sequence information for any given genome sample. That is, in some embodiments, a given referring segment 518 may be stored (non-transitorily) as the one or more variations with respect to the given anchor segment 510. See e.g., the various referring segments 518 and their corresponding anchor segments (e.g., 510, 512, and 514) in FIG. 5B; and note differences in totals as between a given second repository (522a, 522b, and 522c together with 522d) and first repository 521.

In some embodiments, the one or more genome samples may be one or more segments 114 (or similar segments 435). In some embodiments, the one or more genome samples may be two or more genome samples, because when there may be only one genome sample, then storage efficiencies may not be gained by using anchors segments 510 and referring segments 518. Although when presented with only one genome sample, that one genome sample may be segmented (e.g., per segmenting method 400 [or step 405 and/or step 410] as noted in the FIG. 4 series of figures and as discussed above in the FIG. 4 series of figures discussion) and the resulting segments 114 may then be stored by using anchor segments 510 and referring segments 518 to save in storage.

In some embodiments, prior to step 502 of assigning the one or more anchor segments 510, method 500 may comprise a step of receiving the two or more genome samples (or the one or more genome samples); wherein each such genome sample may be from (e.g., associated with) a different individual.

In some embodiments, a source from where the two or more genome samples may have originated from may be different sources. For example, and without limiting the scope of the present invention, each of the two or more genome samples may have originated from different sources. In some embodiments, those sources may be one or more storage units 708, databases and/or repositories (e.g., similar repositories 437). In some embodiments, those one or more storage units 708, databases and/or repositories (e.g., similar repositories 437) may be ones that are part of one or more systems of various embodiments of the present invention. Whereas, in other embodiments, at least some of those one or more storage units 708, databases and/or repositories (e.g., similar repositories 437) may be outside of the one or more systems of various embodiments of the invention.

In some embodiments, the two or more genome samples (or the one or more genome samples) may be non-transitorily stored in one or more of: one or more storage units 708, at least one database, and/or at least one repository. In some embodiments, those one or more storage units 708, the at least one database and/or the at least one repository may be part of one or more systems of various embodiments of the invention.

In some embodiments, the two or more genome samples (or the one or more genome samples) may be selected from: whole genome sequences 110, partial genome sequences, and/or segments 114 (or similar segments 435). In some embodiments, either or both of the two or more genome samples may be segments 114 (or similar segments 435); wherein such segments 114 (or similar segments 435) may have been generated according to at least one of the embodiments discussed in the FIG. 4 series of figures discussion above. For example, and without limiting the scope of the present invention, such segments 114 (or similar segments 435) may have been generated by using one or more align sequences 420 (or one or more align segments) according to step 410.

In some embodiments, the two or more genome samples may each be from different individuals. In some embodiments, each of the two or more genome samples may share at least one locus, such that the two more genome samples may be alignable for a purpose of identifying the one or more variations. In some embodiments, each of the two or more genome samples may share at least one locus with the given anchor segment 510, such that the two more genome samples may be alignable with the given anchor segment 510 for a purpose of identifying the one or more variations (see e.g., FIG. 5C). In some embodiments, the one or more variations may be selected from one or more of: insertions, deletions, and/or replacements of one or more nucleotides as between the given anchor segment 510 and the genome sample used to generate the given referring segment 518. In some embodiments, the one or more variations may comprise one or more polymorphisms as between the given anchor segment 510 and the genome sample used to generate the given referring segment 518. In some embodiments, the one or more anchor segments 510 may be used as a basis for aligning the two or more genome samples for purposes of identifying the one or more variations (see e.g., FIG. 5C).

In some embodiments, step 508 of FIG. 5A may comprise anonymizing one or more referring segments 518 into one or more anonymized referring segments. In some embodiments, the one or more variations used to generate the given referring segment 510 may be anonymized to minimize identification of an individual associated with the given referring segment 518. In some embodiments, a given referring segment 518 is selected from the one or more referring segments 518. And a given referring segment 518 along with its corresponding anchor segment 510 may be used to determine to full sequence information of a given genome sample (e.g., segment 114) that the given referring segment 518 refers to. Thus, in some scenarios a non-anonymized referring segment 518 could reveal an individual's identity; and so under some scenarios it may be desirable to anonymize at least some referring segments 518 to minimize such identification possibility. In some embodiments, such anonymization may be accomplished by modifying the one or more variations; or modifying the referring segment 518. In some embodiments, such modifying may be selected from one or more of: inserting, deleting, or replacing of one or more nucleotides associated with the one or more variations. In some embodiments, such modifying may be selected from one or more of: inserting, deleting, or replacing of one or more nucleotides associated with the referring segment 518 that may be being modified (anonymized). Alternatively, or in addition, in some embodiments, a given anchor segment 510 may be modified (anonymized), which may then result in anonymization of that anchor segment's 510 given (e.g., associated) referring segments 518. Alternatively, or in addition, in some embodiments, the given referring segment 518 that it may be desired to anonymize, may be associated with a different anchor segment 510, which may result in anonymizing that given referring segment 518.

In some embodiments, a record of such anonymization may be non-transitorily stored in the one or more storage units 708, the databases, and/or in the repositories. This anonymization record may be necessary in order to reconstruct the full sequence information of the genome sample that the anonymized referring segment may refer to. Thus, with anonymized referring segments 518, one may need: the record of anonymization, the anonymized referring segment 518, and the relevant anchor segment 510 in order to reconstruct the sequence information of the genome sample (e.g., segment 114) that was being referred to. Note, such a record of anonymization may be deleted or access controlled, such as in "opt-out" as discussed in FIG. 11D and its corresponding discussion below.

FIG. 5C may depict two example genome samples (530a and 530b) and the one or more variations 532 as between those two genome samples. FIG. 5C may also depict various examples of different types (e.g., 533, 534, 535, and 536) of the one or more variations 532. Alternatively, FIG. 5C may depict an example of aligning a genome sample (530a or 530b) with an anchor segment (530b or 530a, respectively) in accordance with one or more embodiments of the invention. For example, in such an interpretation of FIG. 5C, 530a may be a given anchor segment 510, and 530b may be a genome sample.

In some embodiments, each of the two or more genome samples (530a and 530b) may share at least one locus with the given anchor segment 510, such that the two more genome samples (530a and 530b) may be alignable with the given anchor segment 510 for a purpose of identifying the one or more variations 532. In some embodiments, one or more variations 532 may be selected from one or more of: single nucleotide polymorphism 533, insertions 534, deletions 535, and/or replacements 536 of one or more nucleotides as between the given anchor segment 510 and the genome sample used to generate the given referring segment 518. See e.g., FIG. 5C.

For example, FIG. 5C may show one or more variations 532 between two or more genome samples (530a and 530b) wherein one or more variations 532 may be indicated by position and variations between the two or more genome samples (530a and 530b). In one embodiment, the two or more genome samples (530a and 530b) may be whole genome sequences 110. In another embodiment, the two or more genome samples (530a and 530b) may be segments 114 of the two or more genome samples (530a and 530b). In particular, FIG. 5C may depict: a single nucleotide polymorphism 533 in sample 530b of "C" from "T" at an $8^{th}$ position of sample 530a; an insertion of two nucleotides 534 in sample 530b of "CG" from after position 15 of sample 530a; a deletion of two nucleotides 535 in sample 530b with respect to sample 530a of "CT" at a position 23 of sample 530a; and a replacement 536 of "GACT" in sample 530b with respect to "TCAG" at the position 30 of sample 530a. In one embodiment, sample 530a may be anchor segment 510 for one or more variations 532 of referring sample 530b to reduce storage space in systems. In another embodiment, sample 530a may be anchor segment 510 with pre-defined segments that may be used to align and/or divide (segment) other referring genome sequences. In another embodiment, one or more variations 532 may be modified to anonymize the referring genome sequence. In yet another embodiment, multiple anchor segment 514 (see e.g., FIG. 5B and FIG. 5D) may be used to associate with different types of referring sequences. However, persons of skill in the art will recognize that the invention may be practiced with respect to other sequence variation formats and different types of sequence alignment methodologies without deviating from the scope of the present invention.

FIG. 5D may depict a flow diagram of exemplary steps for a process of using multiple anchor segments 514 and multiple referring segments 518 to minimize storage space. For example, in FIG. 5B, second repositories (522a and 522b) may each only utilize one anchor segment 510 (including calculated anchor segment 512); but second repository 522c together with second repository 522d may utilize two different anchor segments 514, i.e., two different multiple anchor segments 514, one in second repository 522c and the other in second repository 522d. Note, of the three examples depicted in FIG. 5B, second repository 522c together with second repository 522d has the most storage savings, i.e., the lowest total of 14. In general, the greater the number of genome samples and/or the greater the diversity (variations) between genomes samples, there may be storage benefits to be obtained by using two or more multiple anchor segments 514. FIG. 5D may depict steps involved for utilizing two or more multiple anchor segments 514. In some embodiments, FIG. 5D may depict steps of method 540. In some embodiments, method 540 may comprise steps: step 542, step 544, step 546, step 548, and step 549.

In some embodiments, step 542 may comprise subdividing the two or more genome samples (e.g., genome sample 530a and genome sample 530b of FIG. 5C; or e.g., the six genome samples of first repository 521 of FIG. 5B) into two or more groups of segments 114. In some embodiments, temporary files and/or temporary repositories (e.g., in RAM) may be used to for this purpose. In some embodiments, step 542 of subdividing the two or more genome samples into the two or more groups of segments may be done by grouping the two or more genome samples on a basis of commonality. In some embodiments, this commonality, for example, and without limiting the scope of the present invention, might be by similar or same race or ethnicity that the given genome sample may be from. This basis of commonality could be other similarities as between the two or more genome samples, such as similarities in sequence information and/or locus from where the two or more genome samples originates. In some embodiments, other methods or techniques, besides or in addition to grouping on the basis of commonality may utilize other methods or techniques for grouping, such as, but not limited to, utilizing average anchor segments. See e.g., FIG. 5E. In either embodiment, grouping may be determined by an algorithm that determines which segments may belong in which groups. And such that storage space may be used efficiently. For example, the grouping done in FIG. 5B from first repository 521 to second repository 522c and second repository 522d may be based on increasing storage savings as compared against the total storage load of first repository 521 in FIG. 5B.

Continuing discussing FIG. 5D, in some embodiments, step 544 may comprise assigning multiple anchor segments 514, with at least one such multiple anchor segment 514 for each resulting group of step 542. For example, if there may be two or more groups per step 542, then there may be two or more multiple anchor segments 514 per step 544. Note, in terms of operational mechanics, step 544 may proceed substantially equivalently to step 502 of method 500 depicted in FIG. 5A. Thus, with these multiple anchor segments 514, the at least one multiple anchor segment 514 per each group from step 542, may have different sequence information for each such multiple anchor segment 514 (see e.g., multiple anchor segment 514 in second repository 522c and multiple anchor segment 514 in second repository 522d in FIG. 5B); but could coincidently have identical sequence information.

Continuing discussing FIG. 5D, in some embodiments, step 546 may comprise generating a given referring segment 518 for each such genome sample in each such grouping (from the grouping of step 542), using that group's individual multiple anchor segment 514 (from step 544). In some embodiments, each such generated referring segment 518 may not also be one of the multiple anchor segments 514.

In some embodiments, step 548 may comprise storing (non-transitorily when dealing with electronic records and/or digital files) of each such multiple anchor segment 514 of step 544. Such multiple anchor segment 514 storage may be in one or more storage units 708, the database, and/or in repositories. The repositories may be a same repository or different repositories. For example, in FIG. 5B, second repository 522c together with second repository 522d may be one single repository storing both multiple anchor segments 514. But in some embodiments, second repository 522c and second repository 522d may be two different repositories (e.g., in a manner that matches the grouping).

In some embodiments, step 549 may comprise storing (non-transitorily when dealing with electronic records and/or digital files) of each referring segment 518 into a specific repository representing its grouping from step 542; wherein that specific repository may also comprise storing of the relevant multiple anchor segment 514. In some embodiments, each referring segment 518 may be non-transitorily stored in the different repository that also includes the multiple anchor segment 514 used to generate each referring segment 518 for that grouping.

Second repository 522c together with second repository 522d in FIG. 5B may depict an end result of method 540 operating upon first repository 521. That is, in step 542, the six genome samples of first repository 521 may be split into two groups in second repository 522c together with second repository 522d; that of (1) "AAGTG", (2) "AAGCG" in a first (or top) group in second repository 522c; and (3) "TAGTG"; and that of (4) "TTGCC", (5) "TTACC", and (6) "TTGCA" in a second (or bottom) group in second repository 522d. See FIG. 5B. In step 544, an anchor segment 514 may be assigned for each of these two groups, which in the FIG. 5B example of second repository 522c, results in an anchor segment 514 of (1) "AAGTG" for the first (top) group; and an anchor segment 514 of (4) "TTGCC" for the second (bottom) group in second repository 522d. See e.g., FIG. 5B. (Note, in second repository 522c and second repository 522d, each multiple anchor segment 514 used in this example represents an identical genome sample of first repository 521 (e.g., that of sample (1) and that of sample (4), respectively) and this illustration was done for simplicity in demonstrating operational mechanics of method 540; however, each of the multiple anchor segments 514 in second repository 522c and second repository 522d could have been calculated anchor segments 512; which may or may not represent identical sequence information of the genome samples used to assign the given anchor segment.) Then per step 546, referring segments 518 for each group (first [top] and second[bottom]) may be generated. For example, the first (top) group in second repository 522c may comprise two referring segments 518 of (2) "_ _ _ C _" and of (3) "T _ _ _ _"; and the second (bottom) group of second repository 522d may comprise two referring segments 518 of (5) "_ _ A _ _" and of (6) "_ _ _ _ A". Then in steps 548 and 549, anchor segment 514 of (1) "AAGTG" along with referring segments 518 of its first group (top group) of (2) "_ _ _ _ C _" and of (3) "T _ _ _ _" may be stored in one repository, i.e., second repository 522c; while anchor segment 514 of (4) "TTGCC" along with its referring segments 518 from its second group (bottom group) of (5) "_ _ A _ _" and of (6) "_ _ _ _ A" may be stored within a different repository, i.e., second repository 522d.

The cost of adding an anchor segment 514 for each grouping of segments 114 per steps 542 and 544 may be the amount of storage needed to store a full segment 114 (i.e., full sequence information for that segment 114) representing the given multiple anchor segment 514. But the benefit of adding such additional anchor segments 514, e.g., one anchor segment 514 per each group of segments 114, may be an amount of storage saved due to the lowered amount of variations in referring segments 518 that need to be stored. For example, in FIG. 5B, second repository 522c together with second repository 522d, both five nucleotide long anchor segments 514 may total 10, but overall second repository 522c together with second repository 522d may have total storage load of 14, which may be storage savings of 16 as compared to first repository 521.

In some embodiments, method 540 (FIG. 5D) may be combined with method 500 (FIG. 5A). For example, step 542 may proceed step 502. Step 544 may replace step 502. Step 546 may replace step 504. And steps 548 and 549 may replace step 506.

FIG. 5E may depict a flow diagram of exemplary steps for a process, e.g., method 560, of using calculated average anchor segments to maximize storage savings. As noted above, in some embodiments, the average anchor segment may be a subset of calculated anchor segment 512. In some embodiments, method 560 may be a method for using one or more average anchor segments for a purpose of saving storage space. In some embodiments, FIG. 5E may depict steps of method 560. In some embodiments, method 560 may comprise the following steps: step 561, step 562, step 563, step 564, step 565, step 566, step 567, and step 568.

In some embodiments, step 561 may comprise designating at least two group leaders from a repository comprising two or more segments 114. Note, in some embodiments, step 561 of designating two segments 114 from the two or more segments 114 as either one group leader or the other group leader, may be done randomly or arbitrarily, as the method's overall iterative nature may still quickly calculate optimal average anchor segments.

In some embodiments, step 562 may comprise forming at least two groups of segments 114, wherein each group of segments selected from the at least two groups of segments 114 may be associated with each of the at least two group leaders, such that each group of segments 114 may have its own designated group leader. Note in some embodiments, step 562, i.e., the step forming two or more groups of segments may proceed step 561, in which case at least one segment 114 from each formed group of segments 114 may be designated a group leader for that group.

In some embodiments, step 562 of forming the at least two groups of segments 114 may comprise matching any segments 114 selected from the two or more segments 114 with either one or another of the at least two group leaders. In some embodiments, such matching may be done a basis of similarity between segments 114 and either the one or the other of the at least two group leaders. In some embodiments, the matching may be done a basis of any given segment 114 selected from the two or more segments 114 being closer in Levenshtein distance either the one or the other of the at least two group leaders.

In some embodiments, step 563 may comprise calculating for each group of segments 114 selected from the at least two groups of segments 114 an average anchor segment. In some embodiments, a given average anchor segment may be calculated by determining an artificial segment (artificial in the sense that this segment may be calculated) that may be a least distance from all segments 114 in that given group of segments 114. In some embodiments, a given average anchor segment may be calculated by determining the artificial segment that may be an equal distance from all segments 114 in that given group of segments 114. In some embodiments, the artificial segment being "least distant" from a set of the segments 114 of a given group (which may be in a same repository) may refer to the artificial segment that may be closest in distance to the segments 114 in this set according to an algorithm solving a least squares problem. In some embodiments, the artificial segment being "least distant" from a set of the segments 114 of the given group may refer to the artificial segment that may be closest in Levenshtein distance to the segments 114 in this set.

In some embodiments, step 564 may comprise ungrouping the at least two groups of segments 114 into one larger group comprising the two more or segments 114 and each of the average anchor segments that was calculated for group of segments 114 (that may now be ungrouped.

In some embodiments, step 565 may comprise forming a new at least two groups of segments 114, wherein each new group of segments 114 selected from the new at least two groups of segments 114 may be associated with each of the average anchor segments. In some embodiments, the forming of step 565 may be done on a same or similar basis as the forming under step 562.

In some embodiments, step 566 may comprise calculating for each new group of segments 114 selected from the new at least two groups of segments 114 a new average anchor segment for each newly formed group. The mechanics of this calculation may proceed in substantially equivalent manner as in step 563.

In some embodiments, step 567 may comprise comparing the new average anchor segments calculated in step 566 against the average anchor segments calculated in step 563. Step 567 may route to step 568 if the compared average anchor segments may be the same; or may route back to step 564 in an iterative fashion if the compared average anchor segments are different.

In some embodiments, step 568 may comprise using the new anchor segments of step 566 and the new groupings of segments 114 of step 565. That is, if the new average anchor segments of step 566 may be substantially the same as the average anchor segments of step 563, then method 560 may proceed to use the new average anchors segments and the new at least two groups of segments 114. In some embodiments, such use may then proceed with generating one or more referring segments 518 from the segments 114 in each of the new group(s), as well as using the given new average anchor segment for each such new group; i.e., this may be a step substantially equivalent as step 504 (FIG. 5A) or step 546 (FIG. 5D). The method may then proceed to non-transitorily store the new average anchor segment(s) as well as the generated referring segments 518; i.e., this may be a step substantially equivalent as step 506 (FIG. 5A) or step 548 and step 549 (FIG. 5D). Also, in some embodiments, such referring segments 518 may be anonymized by modifications, as noted above; wherein such anonymized (modified) referring segments may also be non-transitorily stored. Such non-transitory storage may be in one or more storage units 708, the database, and/or repositories. Each new grouping of referring segments 518 (or anonymized referring segments plus the anonymization record) as well as its given average anchor segment may be non-transitorily stored together in a particular repository for that new group.

However, if the new average anchor segments of step 566 may be substantially different from the average anchor segments of step 563, then step 567 may route back to step 564 and with designating the new average anchor segments as the average anchor segments of step 564; i.e., the new groups of step 565 may be ungrouped in step 564; and step 564 may then proceed to step 565, then to step 566, and then to step 567. See e.g., FIG. 5E.

Turning now to a discussion of FIG. 6. FIG. 6 may depict an example of a linkage record 600 with a set of IDs 650 in accordance with one or more embodiments of the invention. In some embodiments, a given linkage record 600 may be a set of instructions for mapping to one or more of: original data 101, one or more genome sequences 110, associated information 120, one or more segments 114, organizational units, fields 812, subfields 814, categories 818, and/or different subfields 816. That is, each ID 650 selected from the set of IDs 650 may point and/or map to a specific organizational unit, field 812, subfield 814, category 818, and/or different subfield 816. In some embodiments, linkage record 600 may comprise an existing linkage record. In some embodiments, once linkage record 600 may be generated, then linkage record 600 may be the existing linkage record.

To understand linkage 600 usefulness and/or importance, it may help to understand how at least some original data 101 may be processed and/or non-transitorily stored. In some embodiments, methods and/or systems may organize 804 (see e.g., FIG. 8A) at least some of original data 101 into the organizational units. In some embodiments, these organizational units may comprise one or more of: fields 812, subfields 814, segments 114, different subfields 816, and/or categories 818. See e.g., FIG. 8B. In some embodiments, at least some of the one or more of: fields 812, subfields 814, segments 114, different subfields 816, and/or categories 818 may be non-transitorily stored within one more storage units 708, the database, and/or the repositories. The process of organizing 804 the at least some of original data 101 into such organizational units may comprise one or more of: dividing 805 fields 812 into subfields 814; segmenting 400 some sequence (e.g., 110) into segments 114; categorizing 807 fields 812 into categories 818; and/or generalizing 806 fields 812 into different subfields 816. See e.g., FIG. 8B.

Now in FIG. 6, in some embodiments, this set of IDs 650 may be a plurality of unique linkage record IDs 650. In some embodiments, each segment 114 selected from the one or more segments 114, each organizational unit selected from the organizational units, each subfield 814 selected from the subfields 814, each category 818 selected from the categories 818, and each different subfield 816 selected from the different subfields 816, each may have associated with it a unique linkage record ID 650 selected from the plurality of unique linkage record IDs 650. See FIG. 6. That is, each: organizational unit, field 812, subfield 814, different field 816, category 818 may have assigned to it a unique linkage record ID 650.

In some embodiments, this plurality of unique linkage record IDs 650 may be the set of instructions for mapping one or more of the organizational units or the one or more segments 114 to original data 101. That is, the plurality of unique linkage record IDs 650 may not be the data itself in a given field 812, subfield 814, different subfield 816, and/or category 807; but that an ID 650 that may permit mapping to respective data. In some embodiments, a given unique linkage record ID 650 may be unique with respect to a type of field 812, subfield 814, different subfield 816, and/or category 818. For example, there may be different categories 818 for different eye colors (e.g., brown, blue, green, and/or hazel); where each different eye color category 818 may have a unique linkage record ID 650. In some embodiments, a given unique linkage record ID 650 may be unique with respect to a type of different subfield 816, for example, individuals over age 80 as one type of different subfield 816; or individuals residing in California as another example of one type of different subfield 816.

However, note in some embodiments, for some data (e.g., some of original data 101), a given unique linkage record ID 650 may also be the data itself. For example, and without limiting the scope of the present invention, social security numbers (or portions thereof) may be both a given unique linkage record ID 650 and a type of personal information 126. For example, and without limiting the scope of the present invention, different physicians working from different organizations, but treating the same patient may have different medical record numbers for that same patient, but may share the same social security number, and thus that same social security number may be used as a basis for grouping the different medical records of that same patient. Social security numbers may be both transmitted in an encrypted manner and non-transitorily stored in an encrypted manner.

In some embodiments, plurality of unique IDs 650 may comprise one or more of: a plurality of IDs 602, a plurality of personal information IDs 604, a plurality of genome segment IDs 606, a plurality of phenotype IDs 608, and/or a plurality of medical record IDs 610. See FIG. 6.

In some embodiments, access to a given linkage record 600 (or a given existing linkage record) may permit determination of at least some of the original data 101. For example, and without limiting the scope of the present invention, access to a given linkage record 600 (or a given existing linkage record) may permit determination of the identity of the individual who may be represented by at least some of original data 101. For example, and without limiting the scope of the present invention, access to a given linkage record 600 (or a given existing linkage record) may permit determination of disease predisposition(s) and/or current disease(s) of the individual who may be represented by at least some of original data 101.

However, note, in some applications of using a given linkage record 600, all original data 101 may not be determined, as some organizing 804 processes may permanently remove some original data 101. For example, the process of generalization 806 into a different subfield 816 or of categorizing 807 into a category 818 may lose some data. See e.g., FIG. 8B. For example, an individual with a date of birth of "Sep. 19, 1992," may have such date of birth information generalized 806 from full date of birth field 812 into just a birth year subfield of "1992," wherein the birth month and birth day may be lost. For example, a GWAS participant with an age of 34, might have such age information categorized 807 into a category 818 of "ages 30 to 35" and thus the specificity of the actual age of 34 may be lost.

In one example, the set of IDs 650 may comprise optional ID(s) 602 for linking extra information from an internal subsystem or an external system. In one embodiment, information associated with the set of IDs 650, i.e., the information that the set of IDs 650 may map to (such as least some of original data 101), may be completely uncorrelated; wherein without accessing linkage record 600, each piece of such information may not be associated with each other. This arrangement may encourage and promote anonymity. In another embodiment, information (such as least some of original data 101) associated with the set of IDs 650 may be partially uncorrelated; wherein without accessing linkage record 600, certain subgroup of information may not be associated with each other. In one embodiment, a data system may store (in a non-transitory manner in some embodiments) the organizational units, fields 812, subfields 814, different subfields 816, categories 818, and/or segments 114 into different repositories wherein the set of IDs 650 may be used to retrieve and/or combine such information from different repositories. In one example, the set of IDs 650 may be primary keys of different tables in one or more relational databases. In another example, the set of IDs 650 may be part of row keys in one or more NoSQL databases. In yet another example, the set of IDs 650 may be embedded in values of the repositories wherein linkage records 600 may be incorporated in exhausted searches for combining such information. In one embodiment, linkage records 600 may be stored (in a non-transitory manner in some embodiments) in a separate repository (separate from one or more of: the organizational units, fields 812, subfields 814, different subfields 816, categories 816, and/or segments 114) with access control; wherein such separate repository may be in communication the one or more of the organizational units, fields 812, subfields 814, different subfields 816, categories 816, and/or segments 114; wherein certain jobs or entities may or may not be permitted to access linkage records 600; or may only access some subgroup in linkage records 600. In another embodiment, certain information (such as the at least some original data 101) associated with linkage record 600 may be stored (in a non-transitory manner in some embodiments) in a separate repository with access control wherein certain jobs or entities cannot access certain information associated with linkage records 600.

FIG. 6 may also show an example of repeated information 620. In some embodiments, repeated information 620 may be used to retrieve and/or update an existing linkage record 600. In some embodiments, repeated information 620 may be used to retrieve and/or update at least some of original data 101 for a given individual. In some embodiments, linkage record 600 may comprise repeated information 620. In some embodiments, repeated information 620 may comprise a plurality of IDs, such as one or more of: ID 622, personal information ID 624, genome segment ID 626, phenotype 628, and/or medical record ID 630. For example, and without limiting the scope of the present invention, personal information ID 624 may comprise and/or may point to (map to) an individual's social security number, which may be used to retrieve and/or update various original data 101 for that individual. For example, repeated information 620 may be used to retrieve and/or update medical record information 124, such as with replicated diagnosis information and/or longitudinal treatment data. For example, repeated information 620 may be used to retrieve and/or update segment 114 and/or its sequence-associated-information 112, such as CpG sites 118 for the DNA methylation. In one embodiment, repeated information 620 may be used to retrieve and/or update information of original data 101 and/or to create a new entry for data associated with the existing set of IDs 650 in a given linkage record 600. In another embodiment, repeated information 620 may be used to generate new data associated with new IDs 650 in the given linkage record 600.

FIG. 6 may also show an example of statistical information 640 for the one or more of: the organizational units, fields 812, subfields 814, different subfields 816, categories 818, and/or segments 114 specified by unique linkage record IDs 650 in linkage record 600. In some embodiments, linkage record 600 may comprise statistical information 640. In some embodiments, statistical information 640 may comprise IDs that may point to statistical data. In some embodiments, statistical information 640 may comprise the statistical data. For example, and without limiting the scope of the present invention, statistical information 640 for an ID specifying age in personal information 126 may comprise one or more of: frequency, mean, and/or standard derivation for each year of birth. For example, and without limiting the scope of the present invention, statistical information 640 for an ID specifying age in personal information 126 may comprise IDs that may map to one or more of: the frequency, the mean, and/or the standard derivation for each year of birth. In one embodiment, a sample set for calculating the statistical information 640 may be data incorporated in the internal system, that may be an embodiment of the present invention. In another embodiment, a sample set may incorporate imported data or may incorporate imported statistical data from the external system; which may then be formatted into statistical information 640 and incorporated into the internal system.

Various aspects of the systems and the methods for practicing features of the present invention may be implemented on one or more computer systems 700. FIG. 7 may show an exemplary computer system 700. In some embodiments, computer system 700 may comprise processing unit(s) 702, input units(s) 704, output unit(s) 710, and storage unit(s) 708; all of which may be coupled, directly or indirectly, via interconnection mechanism 706. In some embodiments, interconnection mechanism 706 may comprise one or more: buses, switches, networks, circuits, cloud, and/or any other suitable interconnection. In some embodiments, input unit(s) 704 may receive input(s) from user(s) and/or from machine(s), e.g., via a network interface (e.g., from a wireless signal received at a radio antenna, from a router, from a network adapter, from a modem, from a gateway, and/or the like). For example, in some embodiments, such inputs may be receiving at least some of original data 101, such as, one or more genome sequences 110 and/or associated information 120. In some embodiments, output unit(s) 710 may display(s) and/or transmit(s) information to user(s) and/or to machine(s). Such information may comprise one or more of: received input feedback indicators; status indicators; confirmation indicators; progress indicators; error indicators; at least some of original data 101 that may have been received; linkage record 600 information; anonymized linkage record 1000 information; indicators associated with carrying out at least some steps of method 400, method 410, method 412, method 500, method 540, method 560, method 800, method 1100, method 1106, method 1122, method 1200, method 1200a, method 1200b, method 1214, method 1214a, method 1300, method 1314, method 1400, method 1402, method 1403, method 1404, method 1406, and/or method 1454; and/or user account information. In some embodiments, input unit(s) 704 and output unit(s) 710 may be used, among other things, to present a user interface; such as, but not limited to a graphical user interface (GUI). Examples of output unit(s) 710 that may be used to provide the user interface may comprise one or more of: printers, display screens for visual presentation of output, speakers, and/or other sound generating devices for audible presentation of output. Examples of input unit(s) 704 that may be used for the user interface may comprise one or more of: keyboards, touch screens, microphones, other audio listening devices, buttons, switches, levers, dials, slides, pointing devices, mice, touch pads, trackballs, joysticks, and/or digitizing tablets. As another example, computer system 700 may receive input information through speech recognition and/or in other audible format.

In some embodiments, processing unit(s) 702 may execute(s) a computer program known as an operating system (e.g., a Microsoft Windows operating system, a Linux operation system, an Apple and/or Macintosh operating system, a mobile computing device operating system, any other suitable operating system, and/or combinations thereof) which may control the execution of other computer programs (e.g., application programs); and may provide for scheduling, input/output and other device control, accounting, compilation, storage assignment, data management, memory management, communication; and/or dataflow control. Collectively, processing unit(s) 702 and the operating system may define a computer platform for which the application programs and other computer program languages may be written in. In some embodiments, processing unit(s) 702 may also execute one or more computer programs to implement various functions and/or method of the present invention. In some embodiments, processing unit(s) 702 may also execute one or more computer programs implementing at least some steps of one or more of the following methods: method 400, method 410, method 412, method 500, method 540, method 560, method 800, method 1100, method 1106, method 1122, method 1200, method 1200a, method 1200b, method 1214, method 1214a, method 1300, method 1314, method 1400, method 1402, method 1403, method 1404, method 1406, and/or method 1454. For example, and without limiting the scope of the present invention, in some embodiments, processing unit(s) 702 may also execute one or more computer programs to implement various functions and/or methods of the present invention, such as, but not limited to, building and/or updating linkage records 600 (and/or anonymized linkage records 1000), segmenting one or more genome sequences 110 into one or more segments 114, and organizing associated information 120 into one or more of: the organizational units, fields 812, subfield 814, different subfields 816, categories 818, and/or segments 114. These computer programs may be written in any type of computer program language, including, but not limited to, a procedural programming language, object-oriented programming language, macro language, and/or combinations thereof.

These computer programs may be stored in one or more storage unit(s) 708. Storage unit(s) 708 may store (hold) information on a volatile or non-volatile medium, and may be fixed and/or removable. Storage unit(s) 708 may include a tangible computer readable and computer writable non-volatile recording medium, on which signals are stored that define a computer program or information to be used by the computer program. The recording medium may, for example, be disk memory, flash memory, and/or any other article(s) of manufacture usable to record and store information (in a non-transitory fashion). In some embodiments, in operation, the processing unit(s) 702 may cause(s) data (such as, but not limited to, at least some of original data 101) to be read from the nonvolatile recording medium into a volatile memory (e.g., a random access memory, or RAM) that may allow for more efficient (i.e., faster) access to the information by the processing unit 702 as compared against the nonvolatile recording medium. The memory may be located in the storage unit 708 and/or in processing unit 702. See e.g., FIG. 7. The processing unit(s) 702 may manipulate(s) the data within integrated circuit memory and may then copy the data to the nonvolatile recording medium after processing may be completed. A variety of mechanisms are known for managing data movement between the non-volatile recording medium and the integrated circuit memory element, and the invention is not limited to any mechanism, whether now known or later developed. The invention is also not limited to a particular processing unit or storage unit.

Note, each and every method and/or step discussed herein and as depicted in the figures may be implemented as non-transitory computer-readable medium including codes executable by a processor. That is, such non-transitory computer-readable medium may be the one or more storage units 708. That is, such a processor may be processing unit(s) 702; or alternatively, processing unit(s) 702 may comprise such a processor.

The FIG. 8 series of figures may comprise FIG. 8A and FIG. 8B. These FIG. 8 series of figures may address a process for processing one or more genome sequences 110 and associated information 120. FIG. 8A may depict a flow diagram of exemplary steps for processing one or more genome sequences 110 and associated information 120. FIG. 8B may depict relationships among organizing 804, dividing 805, segmenting 400, generalizing 806, and/or categorizing 807.

FIG. 8A may depict method 800. In some embodiments, method 800 may be a method for processing one or more genome sequences 110 and associated information 120. In some embodiments, method 800 may comprise steps of: step 802, step 804, step 808, and step 810. In some embodiments, step 802 may be a step of receiving a record. In some embodiments, step 804 may a step of organizing the record (i.e., the received record) to produce one or more organizational unit, i.e., to produce an organized record. In some embodiments, step 808 may be a step of creating and/or finding linkage record(s) 600 so that the organizational units resulting from step 804 may be accessed by the user. In some embodiments, step 810 may be a step of storing one or more of the organizational units (i.e., the organized record) and/or storing the linkage record(s) 600 from step 808.

In some embodiments, step 802 may comprise receiving one or more genome sequences 110 and associated information 120 that may be associated with one or more genome sequences 110. In some embodiments, one or more genome sequences 110 and/or associated information 120 may be subsets of original data 101. Such original data 101 (e.g., one or more genome sequences 110 and/or associated information 120) received, may be received as electrical records and/or digital records. See FIG. 8A.

In one embodiment, the electrical record(s) and/or the digital record(s) may be received through input unit(s) 704. In another embodiment, the electrical record(s) and/or the digital record(s) may be batch uploaded (e.g., received) into one or more storage units 708; which may be for temporary storage until such received information and/or data may be processed, such as per method 800, e.g., by the received information and/or data being organized in step 804. In one embodiment, the received record resulting from step 802 may be processed by processing unit(s) 702. For example, in some embodiments, processing unit(s) 702 running software (i.e., programming and/or code) may carry out steps: step 804, step 808 and/or step 810.

In some embodiments, step 804 (of FIG. 8A) may comprise organizing aspects of associated information 120 into the organizational units by one or more of: dividing 805 fields 812 into subfields 814, segmenting 400 one or more genome sequences 110 (or portions thereof) into one or more segments 114, generalizing 806 fields into different subfields 816 and/or into categories 818, and/or categorizing 807 fields 812 into categories 818. In some embodiments, the step of organizing 804 may comprise the step of segmenting 400. In some embodiments, the step of organizing 804 may comprise the step of dividing 805. In some embodiments, the step of dividing 805 may comprise the step of segmenting 400. In some embodiments, the step of organizing 804 may comprise the step of generalizing 806. In some embodiments, the step of generalizing 806 may comprise the step of categorizing 807. See e.g., FIG. 8A and FIG. 8B.

An example of a field 812 may be a full birth date, e.g., of "Sep. 19, 1992" may be a field 812. And subfields 814 of this particular field 812 may be a subfield 814 for the month of September, a subfield 814 for a day of 19, and a subfield 814 for the birth year of 1992. Such subfields 814 may be arrived at from dividing 805. See e.g., FIG. 8B. Note, if not all subfields 814 from dividing 805 may be kept, then there may be some data loss for subfields 814 that may be discarded. An example of a different subfield 816, may be from a generalizing step 806 that the field 812 of "Sep. 19, 1992" may be generalized into a subfield 816 of only the birth year of 1992. Thus generalization 806 may result in some data loss. See e.g., FIG. 8B. An example of a category 818 may from taking a field 812 of "green eyes" and by categorizing step 807 that green eyes field 812 may be categorized as category 818 of "blue and green eyes." An example of a category 818 may from taking a field 812 of "age 34" and by categorizing step 807 that age 34 field 812 may be categorized as category 818 of "ages 30 through 35." See e.g., FIG. 8B. Thus, categorizing 807 may result in some data loss. Some data loss may be intentional and/or desirable, because such data loss may result in storage savings and/or promote anonymity.

In some embodiments, the step of segmenting 400 one or more genome sequences 110 (or portions thereof) into one or more segments 114 may be omitted and/or optional. For example, if the record received in step 802 may have already comprised a format of one or more segments 114, then the step of segmenting 400 may not be utilized. For example, if one or more genome sequences 110 received in the record was already segmented into one or more segments 114 then the step of segmenting 400 may not be utilized.

Note, in some embodiments a difference in "subfield 814" from "different subfield 816" may reflect how the "subfield" was generated, in that "subfield 814" may have been generated by dividing 805 and "different subfield 816" may have been generated by generalizing 806; yet both may be "subfields" in structural and functional meaning, i.e., comprising some subset of data from original data 101. See e.g., FIG. 8B. For example, in some embodiments, from a database operations and/or mechanics perspective, different subfields 816 and subfields 814 may be treated substantially identically.

In some embodiments, at least one subfield 814 selected from the subfields 814 may comprise some data from original data 101. In some embodiments, at least one subfield 814 selected from the subfields 814 may comprise a unique ID. In some embodiments, this unique ID may be unique per a type of subfield 814; e.g., the type of subfield could a particular birth year. In some embodiments, this unique ID may be unique with respect to the informational content (i.e., data) of a given subfield 814. In some embodiments, at least one subfield 814 selected from the subfields 814 may comprise both some data from original data 101 and the unique ID. In some embodiments, such unique IDs may be the unique linkage record IDs 650. In some embodiments, this discussion of subfields 814 may apply equally to the different subfields 816, to fields 812, and/or to categories 818.

In some embodiments, step 808 (of FIG. 8A) may comprise generating (i.e., creating) one or more linkage records 600 and/or finding and updating one or more existing linkage record 600. Such linkage records 600 are noted FIG. 6 and in the FIG. 6 discussion above. For example, and as noted, in some embodiments, a given linkage record 600 and/or a given existing linkage record 600 may be the set of instructions for mapping to one or more of: original data 101, one or more genome sequences 110, associated information 120, one or more segments 114, the organizational units, fields 812, subfields 814, different subfields 816, and/or categories 818. In some embodiments, such linkage record(s) 600 and/or such existing linkage record(s) 600 may be how the user may access at least some of the information and/or data received in step 802 of receiving the record.

In some embodiments, at least some such of the organizational units, may have assigned a unique linkage record ID 650, such that a given linkage record 600 may be generated (i.e., formed and/or created) and/or updated for a given set of relevant organizational units formed in the organizing step 804. In some embodiments, generation and/or assignment of unique linkage record IDs 650 may a step in the organizing step 804. In some embodiments, generation and/or assignment of unique linkage record IDs 650 may a step in the linkage record formation (or updating) step 808.

In some embodiments, determination of the individual's identity may be protected by the method (e.g., a method 800 embodiment) controlling and/or limiting access to linkage record 600 and/or to existing linkage record 600, such that determination of the individual's identity from at least some of original data 101 which the given linkage record 600 may map to, may be minimized without access to the given linkage record 600 or the given existing linkage record 600. In some embodiments, only appropriate login credentials may be permitted access to a given linkage record 600 and/or a given existing linkage record 600.

In some embodiments, at least some of: fields 812, subfields 814, different subfields 816, categories 818, and/or segments 114 may be non-transitorily stored and/or routed in encrypted formats.

In some embodiments, determination of the individual's identity may be protected by the method (e.g., a method 800 embodiment) controlling and/or limiting access to one or more of: fields 812, subfields 814, different subfields 816, categories 818, or segments 114 that may be populated with critical-identifying-information. In some embodiments, the critical-identifying-information may comprise one or more of the following of the individual: a full name (e.g., full legal name), a complete date of birth, a complete social security number, a complete address (e.g., physical or mailing), a complete phone number, or a genomic sequence with sufficient DNA markers for use in DNA fingerprinting. In some embodiments, only appropriate login credentials may be permitted access to the fields 812, subfields 814, different subfields 816, categories 818, or segments 114 that may be populated with the critical-identifying-information.

In some embodiments, step 810 (of FIG. 8A) may comprise non-transitory storing of one or more of: at least some original data 101, one or more genome sequences 110, associated information 120, one or more segments 114, the organizational units, fields 812, subfields 814, different subfields 816, categories 818, linkage record 600, existing linkage record 600, and/or portions thereof in one or more of: one or more storage units 708, databases, and/or repositories. In some embodiments, at least some such non-transitory storage may be in an encrypted format.

In some embodiments, method 800 may comprise additional processing steps of the record, that may be in addition to receiving 802, organizing, 804, generating linkage records 808, and/or storage 810.

In some embodiments, method 800 may further comprise modifying some data of one or more of: at least some of original data 101, one or more genome sequences 110, one or more segments 114, associated information 120, the organizational units, fields 812, subfields 814, different subfields 816, and/or categories 818 into one or more of: modified-original data from the at least some original data 101, modified-genome-sequences from one or more genome sequences 110, modified-segments from one or more segments 114, modified-associated-information from associated information 120, modified-organizational-units from the organizational units, modified-fields from fields 812, modified-subfields from subfields 814, modified-different-subfields from the different subfields 816, and/or modified-categories from categories 818. In some embodiments, at least some sequence of one or more genome sequences 110 may be modified to produce a modified-genome-sequence. In some embodiments, at least some sequence of one or more segments 114 may be modified to produce a modified-segment.

In some embodiments, the modifying may be one or more of: deleting, inserting, appending, and/or replacing some informational content of the some data. In some embodiments, the modifying may be one or more of deleting, inserting, appending, and/or replacing one or more nucleotides in a given sequence 110 (or portion thereof) to produce the modified-genome-sequence. In some embodiments, the modifying may be one or more of deleting, inserting, appending, and/or replacing one or more nucleotides in a given segment 114 (or portion thereof) to produce the modified-segment.

For example, and without limiting the scope of the present invention, the some data of one or more genome sequences 110 (e.g., a given sequence) (that may have been receive in step 802) may comprise at least some DNA markers used for DNA fingerprinting (or usable for DNA fingerprinting), such that modifying the some data (i.e. the given sequence) may minimize identifying (or re-identifying) of the individual associated with the modified-genome-sequence (or with the modified-segment). For example, and without limiting the scope of the present invention, such DNA markers used (or usable) for DNA fingerprinting may comprise one or more of the thirteen standard short tandem repeat (STR) loci commonly used in DNA fingerprinting, e.g., those noted in FIG. 2 and discussed in the FIG. 2 discussion above.

In some embodiments, one or more of: the modified-original-data, the modified-genome-sequences, the modified-segments, the modified-associated-information, the modified-organizational-units, the modified-fields, the modified-subfields, the modified-different-subfields, and/or the modified-categories may be non-transitorily stored in one or more of: one or more storage units 708, the databases, and/or the repositories.

FIG. 9 may show example of a genome wide association study (GWAS) record 900 or other genetic study record 900. Such a record 900 may be in accordance with one or more embodiments of the invention. Such a record 900 may comprise personal information 902, genome loci and/or variations information 904, phenotype information 906, and medical record(s) 908. In some embodiments, genome loci and/or variations information 904 may comprise at least one locus and/or at least one variation and/or at least one sequence or segment. In some embodiments, such a record 900 may comprise one or more of: personal information 902, genome loci and/or variations information 904, phenotype information 906, and medical record(s) 908. Such a record 900 may be a plurality of records 900. Such a record 900 may pertain to one or more individuals. One may note, that the information contained within a given record 900 may be substantially similar to at least some of original data 101 with respect to informational content. For example, personal information 902 may be substantially similar to personal information 126. For example, genome loci and variations information 904 may be substantially similar to one or more genome sequences 110. For example, phenotype information 906 may be substantially similar to phenotype information 122. For example, medical record(s) 908 may be substantially similar to medical record information 124.

Such a record 900 may have importance in various embodiments of the present invention in several ways. For example, the FIG. 13 series of figures and its corresponding discussion may discuss method(s) for processing genetic study results, such as GWAS results and/or other genetic study results and those results may be received in a format substantially similar to record 900 depicted in FIG. 9.

For example, the FIG. 12 series of figures and its corresponding discussion may discuss method(s) for processing a request for genetic study results of genetic variants from a plurality of different individuals; wherein such method(s)

may provide (and/or generate) a given record 900; wherein at least some of information in such a given record 900 may have processed to maximize anonymity. In one embodiment, the set of genome loci and/or variations 904 may be chosen so as to statistically manage the risk of re-identifying the individual. In another embodiment, certain genome loci and/or variations information 904 may have been deleted and/or modified (anonymized) so as to statistically manage the risk of re-identifying the individual. In one embodiment, fields 812, subfields 814, different subfields 816, and/or categories 818 in record 900 may be chosen so as to statistically manage the risk of re-identifying the individual. In another embodiment, certain fields 812, subfields 814, different subfields 816, and/or categories 818 have been deleted and/or modified (anonymized) so as to statistically manage the risk of re-identifying the individual.

FIG. 10 may show an example of an anonymized linkage record 1000 in accordance with one or more embodiments of the invention. A given anonymized linkage record 1000 may be conceptionally, functionally, and/or structurally substantially similar to a given linkage record 600, in that the given anonymized linkage record may comprise a plurality of IDs, wherein each of these IDs selected from the plurality of IDs may map (may point) to some given packet of information and/or data; however, at least some of this information and/or data that may be mapped to, may be anonymized and/or modified in some form, to minimize and/or mitigate against the ability to identify (and/or re-identify) the individual associated with the information and/or data. Thus one with access to a given anonymized linkage record 1000 may not be able to identify the individual that may be associated with the information and/or the data being mapped to.

With anonymized linkage records 1000, these IDs may be referred to as anonymized IDs 1012. In some embodiments, a given anonymized linkage record 1000 may comprise one or more anonymized IDs 1012. In some embodiments, anonymized IDs 1012 may be non-transitorily stored in one or more of: one or more storage units 708, at least one database, and/or at least one repository. A given anonymized ID 1012 may be conceptionally, functionally, and/or structurally substantially similar to a given unique linkage record ID 650.

For any given linkage record 600, a given anonymized linkage record 1000 may exist or be formed. Or instead of forming a linkage record 600, various embodiments may directly form an anonymized linkage record 1000. In some embodiments, such anonymized linkage record 1000 formation may progress according to method 1100 as noted in FIG. 11A and discussed in the FIG. 11 series of figures discussion below. Thus, for each unique linkage record ID 650 of the given linkage record 600, there may be a corresponding anonymized ID 1012. Likewise, for each piece of information 1114 that a given unique linkage record ID 650 may map to, a corresponding given anonymized ID 1012 may map to corresponding anonymized information 1116. Each piece of information 1114 may be compartmentalized and non-transitorily stored according to method 800 as one more of more: organizational units, fields 812, segments 114, subfields 814, different subfields 816, and/or categories 818. Likewise, each corresponding piece of anonymized information 1116 may be compartmentalized and non-transitorily stored according to method 800 as one more of more: organizational units, fields 812, segments 114, subfields 814, different subfields 816, and/or categories 818; except at least some of the information and/or the data in such organizational units may have been modified and/or anonymized according to method 1100 (such as via step 1104 and/or step 1110). This may be illustrated in an example of FIG. 11C and discussed further below. In terms of types of information, any given piece of information 1114 may be typed as one or more of: ID information, original data 101, one or more genome sequences 110, sequence-associated-information 112, one or more segments 114, associated information 120, phenotype information 122, medical record information 124, and/or personal information 126. Similarly, in terms of types of unique linkage record IDs 650, any given unique linkage record ID 650 may be typed as one or more of: ID information IDs 602, personal information IDs 604, genome segment IDs 606, phenotype IDs 608, and/or medical record IDs 610 (see e.g., FIG. 6). Likewise, in terms of types of information, any given piece of anonymized information 1116 may be typed as one or more of: ID information, original data 101, one or more genome sequences 110, sequence-associated-information 112, one or more segments 114, associated information 120, phenotype information 122, medical record information 124, and/or personal information 126; except at least some of the information and/or the data in such organizational units may have been modified and/or anonymized. Such modified and/or anonymized information and/or data may be denoted as: modified-original-data from the at least some original data 101, modified-genome-sequences from one or more genome sequences 110 (or a portion thereof), a modified-whole-genome-sequence from a whole genome sequence from one individual, a modified-partial-genome sequence from a partial genome sequence from the one individual, one or more modified-segments from one or more segments 114, modified sequence-associated-information from sequence-associated-information 112 (such as, but not limited to, DNA markers useful for DNA fingerprinting), modified-associated-information from at least some associated information 120, modified-phenotype-information from phenotype information 122, modified-medical-record-information from medical record information 124, modified-personal-information from personal information 126, modified-fields from fields 812, modified-subfields from subfields 814, modified-different-subfields from different subfields 816, and/or modified-categories from categories 818. Similarly, in terms of types of anonymized IDs 1012, any given anonymized ID 1012 may be typed as one or more of: anonymized ID information IDs 1002, anonymized personal information IDs 1004, modified genome segment IDs 1006, anonymized phenotype IDs 1008, and/or anonymized medical record IDs 1010 (see e.g., FIG. 10).

In some embodiments, anonymized IDs 1012 of a given anonymized linkage record 1000 may map to information 1114, if the given piece of information 1114 may not reveal the identity of the individual. In some embodiments, anonymized IDs 1012 of a given anonymized linkage record 1000 may refrain from mapping to information 1114 that might reveal the individual's identity.

Note, in some embodiments, determining whether the collective information and/or data, whether information 1114 and/or anonymized information 1116, that a given linkage record 600 and/or a given anonymized linkage record 1000 may map to, may be deemed safely anonymous (or sufficiently anonymous) may involve calculating a multiplied product of frequencies associated with each piece of information and/or data that is being mapped to (e.g., the frequency of some allele variation) and then comparing that multiplied product to some predetermined threshold figure for an appropriate comparison population; and if the calculated multiplied product may be greater than predetermined threshold figure then the information and/or data being mapped to via the given linkage record 600 and/or via the given anonymized linkage record 1000 may be sufficiently anonymous to mitigate against identifying the individual. In some embodiments, the predetermined threshold may be a ratio of a specific population in relation some larger population. For example, and without limiting the scope of the present invention, the specific may be a population of some region (e.g., a state population like California) and the some larger population may be a population of the respective nation (e.g., the United States of America) or the world population.

The FIG. 11 series of figures may comprise FIG. 11A through and including FIG. 11D. These FIG. 11 series of figures may address a process or processes for anonymizing linkage record 600 to produce (i.e., generate, create, and/or find) anonymized linkage record 1000.

FIG. 11A may depict a flow diagram of exemplary steps for the process for anonymizing linkage record 600 which may result in producing (i.e., generating, creating, finding, and/or updating) of anonymized linkage record 1000 of FIG. 10. FIG. 11B may depict a flow diagram of exemplary steps for a process of finding and/or creating anonymized IDs 1012. FIG. 11B may be disclosure of increased details, i.e., of additional steps for step 1106 where step 1106 may be first disclosed in FIG. 11A. FIG. 11C may depict an example of how a given anonymized linkage record 1000 subset may be created from a given linkage record 600 subset. FIG. 11C may be an example illustrating the steps of FIG. 11B. FIG. 11D may depict a flow diagram of exemplary steps of an example of an opt-out procedure to convert linkage record 600 into at least one anonymized linkage record 1000 in accordance with one or more embodiments of the invention.

Note, in some embodiments, prior to anonymizing a given linkage record 600 or a given existing linkage record 600, the method may receive an anonymization request, with information provided in a request, that may request to anonymize linkage record 600 or the existing linkage record 600. In some embodiments, receipt of this anonymization request may initiates anonymizing linkage record 600 or the existing linkage record 600 into the given anonymized linkage record 1000 according to method 1100 (see FIG. 11A) or method 1122 (see FIG. 11D). In some embodiments, the method may automatically generate anonymized linkage record 1000 once the linkage record 600 may be generated or the existing linkage record 600 may be updated.

FIG. 11A may depict method 1100. FIG. 11A may depict at least some steps of method 1100. In some embodiments, method 1100 may be a method for anonymizing linkage record 600 into anonymized linkage record 1000. In some embodiments, method 1100 may be a method for converting linkage record 600 into anonymized linkage record 1000. Note, in some embodiments, method 1100 producing, generating, creating, finding, and/or updating a given anonymized linkage record 1000 may leave a corresponding linkage record 600 intact; wherein such a corresponding linkage record 600 and this given anonymized linkage record 1000 may map to substantially similar informational content; with an exception that in some embodiments at least some of that information content that may be mapped to from the given anonymized linkage record 1000 may be anonymized (modified) information, as in anonymized information 1116 (an example of which may be shown in FIG. 11C). Note, in some embodiments, steps involved in producing, generating, creating, finding, and/or updating a given anonymized linkage record 1000 may or may not also involve deleting the corresponding linkage record 600 that may have been utilized to produce, generate, create, find and/or update the given anonymized linkage record 1000.

In some embodiments, method 1100 may comprise steps of: step 1104, step 1106, and step 1120. Step 1104 may pertain to modifying (anonymizing) one or more genome sequences 110. Step 1106 may pertain to finding and/or creating anonymized IDs 1012. Step 1120 may pertain to creating and/or updating anonymized linkage record 1100, which may involve utilizing such anonymized IDs 1012.

In some embodiments, step 1104 may comprise modifying at least some data (i.e., at least some of the informational content) of one or more genome sequences 110 for a purpose of anonymizing the at least some data, so as to minimize the ability to identify or re-identify the individual.

In some embodiments, one or more genome sequences 110 may be as discussed above in the FIG. 1 discussion. In some embodiments, one or more genome sequences 110 may comprise one or more of: a whole genome sequence of one individual, a partial genome sequence of the one individual, one or more segments 114 derived from the whole genome sequence, or one or more segments 114 derived from the partial genome sequence. In some embodiments, such segments 114 may be produced from segmenting method 400, see e.g., FIG. 4A and the above discussion of the FIG. 4 series of figures.

In some embodiments, step 1104 of modifying may produce one or more of: a modified-whole-genome-sequence from the whole genome sequence of the one individual, a modified-partial-genome sequence from the partial genome sequence of the one individual, and/or one or more modified-segments from the one or more segments 114. In some embodiments, step 1104 of modifying may be one or more of: deleting, inserting, appending, and/or replacing one or more nucleotides in the at least some data of the one or more genome sequences 110. In some embodiments, step 1104 of modifying may be one or more of: deleting, inserting, appending, and/or replacing one or more nucleotides in the at least some data of the one or more segments 114. In some embodiments, step 1104 of modifying may be accomplished, in whole or in part, by storing sequence information (of one or more genome sequences 110 and/or one or more segments 114) in standard IUB/IUPAC abbreviations for nucleic acids.

For example, and without limiting the scope of the present invention, the at least some data of the one or more genome sequences 110 (or of the one or more segments 114) that may be modified in step 1104 may comprise at least some DNA markers used for DNA fingerprinting, such that modifying the at least some data may minimize the ability to identify (or re-identify) the individual from a given nucleic acid sequence that has been thus modified. For example, and without limiting the scope of the present invention, those DNA markers used for DNA fingerprinting may comprise one or more of the thirteen standard short tandem repeat (STR) loci commonly used in DNA fingerprinting disclosed in FIG. 2 and discussed in the FIG. 2 discussion above. Note, such DNA markers may not be limited to the thirteen STR loci depicted in FIG. 2. Any nucleic acid sequence in the one or more genome sequences 110 and/or in the one or more segments 114, either alone or in aggregate with other sequences, that may provide sufficient information for identifying the individual, may be candidate sequences (and/or candidate segments) that may be processed according to step 1104 to minimize identification of the individual.

In FIG. 11A, in some embodiments, step 1106 may comprise one or more of finding and/or creating (i.e., producing and/or generating) anonymized IDs 1012. In some embodiments, step 1106 may be expanded in FIG. 11B by steps: step 1108, step 1110, and step 1112. In some embodiments, step 1106 (or method 1106) may comprise steps: step 1108, step 1110, and step 1112. Step 1108 may use a given linkage record 600 to identify information 1114 (see FIG. 11C for an example of information 1114) that the given linkage record 600 maps to. Continuing discussing FIG. 11B, step 1110 may modify at least some of this information 1114 that may be mapped to, creating at least some anonymized information 1116 (see FIG. 11C for an example of anonymized information 1116). Continuing discussing FIG. 11B, step 1112 may assign anonymized IDs 1012 to each such created anonymized information 1116. See e.g., FIG. 11B.

In some embodiments, before step 1106 of finding and/or creating anonymized IDs 1012, method 1100 may comprise receiving a request. This request may comprise at least some information sufficient to locate at least one unique linkage record ID 650 associated with a given linkage record 600 such that a plurality of unique linkage record IDs 650 associated with that given linkage record 600 may be identified. In some embodiments, the at least some information of this request may be substantially similar to at least some information in a given record 900. See e.g., FIG. 9 and its discussion. That is, step 1106 of finding and/or creating anonymized IDs 1012 may need one or more relevant unique linkage record IDs 650. In some embodiments, at least some anonymized IDs 1012 may be derived from at least some unique linkage record IDs 650 associated with a given linkage record 600. And in order to obtain the one or more relevant unique linkage record IDs 650, the request must provide the at least some information to key up this the one or more relevant unique linkage record IDs 650.

In some embodiments, the at least some information in this request may result in finding and/or pulling more than one relevant linkage record 600. In some embodiments, this request may be the request associated with the FIG. 12 series of figures and their discussion. In some embodiments, this request may comprise requesting from the individual to opt-out of their linkage record 600 as noted in FIG. 11D and discussed in the FIG. 11D discussion below.

As noted, step 1106, in some embodiments, may be expanded upon by additional steps as noted in FIG. 11B. In some embodiments, step 1106 (or as method 1106) may comprise steps: step 1108, step 1110, and step 1112. Collectively these steps may result in deriving anonymized IDs 1012 that may be necessary to form a given anonymized linkage record 1000.

Continuing discussing FIG. 11B, in some embodiments, step 1108 may comprise using a given finite plurality of unique linkage record IDs 650 of the corresponding linkage record 600 to identify information 1114 that the corresponding linkage record 600 may map to. As noted above, in some embodiments, this may first entail receiving the request which may include the at least some information sufficient to create, find, and/or pull the corresponding linkage record 600, from which the given finite plurality of unique linkage record IDs 650 may be identified, as well as the information 1114 that the corresponding linkage record 600 may map to. In some embodiments, this information 1114 that the corresponding linkage record 600 may map to may comprise one or more of: at least some original data 101, one or more genome sequences 110 (or a portion thereof), a whole genome sequence from one individual, a partial genome sequence from the one individual, one or more segments 114 derived from the whole genome sequence, one or more segments 114 derived from the partial genome sequence, at least some associated information 120, fields 812, subfields 814, different subfields 816, and/or categories 818.

Continuing discussing FIG. 11B, in some embodiments, step 1110 may comprise modifying at least some of the information 1114 identified from step 1108 to create the anonymized information 1116. In some embodiments, such modifying in step 1110 may comprise one or more of: deleting, inserting, appending, and/or replacing some informational content of the at least some of the information 1114 identified from step 1108 to create the anonymized information 1116. In some embodiments, such modifying in step 1110 may comprise one or more of: dividing 805 fields 812 into subfields 814, segmenting 400 sequences (e.g., one or more genome sequences 110 [or portions thereof]) into segments 114, generalizing 806 fields 812 into different subfields 816, and/or of categorizing 807 fields 812 into categories 818. In some embodiments, such modifying under step 1110 may modify one or more of: at least some original data 101, one or more genome sequences 110 (or a portion thereof), a whole genome sequence from one individual, a partial genome sequence from the one individual, one or more segments 114 derived from the whole genome sequence, one or more segments 114 derived from the partial genome sequence, at least some sequence-associated-information 112, at least some associated information 120 (e.g., at least some phenotype information 122, medical record information 124, and/or personal information 126), fields 812, subfields 814, different subfields 816, and/or categories 818 into the anonymized information.

In some embodiments, anonymized information 1116 produced by step 1110 may comprise one or more of: modified-original-data from the at least some original data 101, modified-genome-sequences from one or more genome sequences 110 (or a portion thereof), a modified-whole-genome-sequence from the whole genome sequence from one individual, a modified-partial-genome sequence from the partial genome sequence from the one individual, one or more modified-segments from one or more segments 114, modified-associated-information from at least some associated information 120, modified-fields from fields 812, modified-subfields from subfields 814, modified-different-subfields from different subfields 816, and/or modified-categories from categories 818.

For example, and without limiting the scope of the present invention, in some embodiments, various full dates which may comprise a month, a day, and a year; may be anonymized (modified) by retaining only the year. Such full dates may be birthdates, admission dates, discharge dates, dates of examination, dates of treatment, dates of events, dates of death, and/or the like. Similarly, any particular age may be anonymized (modified) by categorizing 807 an age field 812 (e.g., age 91) into some age range category 818 (see e.g., FIG. 8B) (e.g., "age 90 and older").

Continuing discussing FIG. 11B, in some embodiments, step 1112 may comprise assigning one anonymized ID 1012 for each such created unit of anonymized information 1116, created from step 1110. Each such assigned anonymized ID 1012 in aggregate as a group or groups may form the anonymized IDs 1012, which under step 1120 (see e.g., FIG. 11A) may form a given anonymized linkage record 1000. See e.g., FIG. 11B. In some embodiments, assignment of anonymized IDs 1012 may be done via an ID generation and assignment algorithm, which may be random based, rule based, derived from corresponding unique linkage record IDs 650, and/or combinations thereof. Such algorithms may check to make sure a generated and/or assigned ID has not already been assigned; and then once cleared for assignment, the ID may be assigned as a given anonymized ID 1012. In some embodiments, anonymized IDs 1012 may be non-transitorily stored in one or more of: one or more storage units 708, at least one database, and/or at least one repository.

In some embodiments, deriving a given anonymized ID 1012 may comprise a step of altering each relevant unique linkage record ID 650 (or of altering a copy of each relevant unique linkage record ID 650) to form the given anonymized ID 1012. In some embodiments, such altering may comprise one or more of: deleting, inserting, appending, and/or replacing one or more characters of each unique linkage record ID 650 (or the copy) to be altered to create each given anonymized ID 1012. That is, in some embodiments, the anonymized IDs 1012 may be derived directly from the plurality of unique linkage record IDs 650. For example, and without limiting the scope of the present invention, this may be a method for how step 1112 operates to generate and/or assign anonymized IDs 1012. In some embodiments, modifying a unique linkage record ID 650 into an anonymized ID 1012 may involve deleting some portion of the unique linkage record ID 650 (or the copy) being modified. For example, and without limiting the scope of the present invention, a unique linkage record ID 650 (or the copy) that may map to: a given field 812, a given subfield 814, a given category 818, and/or a given different subfield 816 might be modified by deletion, insertion, appending, and/or replacement of one or more characters in the unique linkage record ID 650 (or the copy) being modified. In some embodiments, modifying a unique linkage record ID 650 (or the copy) into an anonymized ID 1012 may involve inserting some character(s) into the unique linkage record ID 650 (or the copy) being modified. In some embodiments, modifying a unique linkage record ID 650 (or the copy) into an anonymized ID 1012 may involve appending some character(s) into the unique linkage record ID 650 (or the copy) being modified. In some embodiments, modifying a unique linkage record ID 650 (or the copy) into an anonymized ID 1012 may involve deletion, insertion, appending, reordering, or some combination thereof to create each given anonymized ID 1012 from a given unique linkage record ID 650 (or the copy).

In some embodiments, creating anonymized IDs 1012 may not utilize unique linkage record IDs 650, but rather, such created anonymized IDs 1012 may be created per an ID generation and/or assignment algorithm. In some embodiments, such algorithms may check to make sure a created ID has not already been assigned.

Irrespective of how anonymized IDs 1012 may be derived or created, in some embodiments, each unique linkage record ID 650 that maps to some information (e.g., information 1114), correspondingly, each anonymized ID 1012 may point to corresponding anonymized information (e.g., anonymized information 1116). For example, see FIG. 11C. In FIG. 11C, some given linkage record 600 may comprise a given unique linkage record ID 650 that may have an ID designation as "7727". ID_7727 in this example may map to a birthdate of "09/19/1992" (i.e., Sep. 19, 1992), wherein the birth year may be "1992". This birthdate may be an example of information 1114. That is, this birthdate may be the identified information 1114 that this particular unique linkage record ID 650 of this linkage record 600 may map to. This first portion of FIG. 11C may illustrate step 1108 of using the given linkage record 600 to identify information 1114 that this linkage record 600 may map to, such as information 1114, which may be this birthdate. Then FIG. 11C may illustrate step 1110 of how information 1114 may be modified to create (generate) anonymized information 1116, such as just the birth year of "1992". That is, in this example, the birth year "1992" may be the anonymized information 1116. This example of modification to create anonymized information 1116, may be an example of dividing 805 from field 812 into subfield 814 or of generalizing 806 from field 812 into different-subfield 816. This example of modification to create anonymized information 1116, may be an example of deleting the birth month and of deleting the birth day to leave just the birth year. Lastly, FIG. 11C may illustrate step 1112 of assigning (generating) an anonymized ID 1012 that may map to the created anonymized information 1116 of the birth year. In this example, anonymized ID 1012 of "9125" may map to the birth year of "1992."

In some embodiments, a given anonymized linkage record 1000 may have already been formed; e.g., according to method 1100. Likewise, given anonymized IDs 1012 and given anonymized information 1116 may have already been formed. Then, various methods and/or systems embodiments of the present invention may receive the request and/or may receive a new request. In some embodiments, the information provided in the request and/or in the new request may comprise at least some information sufficient to locate at least one anonymized ID 1012 associated with the given anonymized linkage record 1000 such that other anonymized IDs 1012 associated with that given anonymized linkage record 1000 may be identified.

FIG. 11C may depict an example illustration of method 1106, i.e., of steps: step 1108, step 1110, and step 1112 of FIG. 11B. FIG. 11C may begin (e.g., at an upper left) with a subset of a given corresponding linkage record 600; wherein for this subset one may be concerned with a unique linkage record ID 650 of "ID_7727". Note, this particular unique linkage record ID 650 may have been identified because prior to method 1106 (or step 1106), the method (e.g., method 1100) may have received the request which may have included at least some information that would enable finding and/or pulling this unique linkage record ID 650 of "ID_7727". For example, that request may have included a birthdate of "Sep. 19, 1992". In any event, this unique linkage record ID 650 of "ID_7727" may map to a birthday repository where field 812 may comprise information 1114 of a relevant birthday of "Sep. 19, 1992". This information 1114 may be non-transitorily stored in one or more of: one or more storage units 708, the databases, and/or the repositories that may be associated with the one or more method and/or with one or more systems of various embodiments of the present invention. The step of identifying this information 1114 of "Sep. 19, 1992" may be an example of step 1108. Next, step 1110 may modify information 1114 to produce anonymized information 1116. In FIG. 11C this may involve modifying "Sep. 19, 1992" into just a birth year of "1992". In FIG. 11C anonymized information 1116 may be this birth year of "1992". In some embodiments, this modification step 1110 may have been accomplished by deleting a birth month of "September" and by deleting a birth day of "19". In some embodiments, this modification step 1110 may have been accomplished by dividing 805 field 812 of "Sep. 19, 1992" into subfield 814 of "1992". In some embodiments, this modification step 1110 may have been accomplished by generalizing 806 field 812 of "Sep. 19, 1992" into different subfield 816 of "1992". Once information 1114 may have been modified into anonymized information 1116, step 1112 may proceed with assigning a given anonymized ID 1012 for that given anonymized information 1116, see e.g., FIG. 11C. For example, anonymized ID 1012 in FIG. 11C may be "9125". Other anonymized information 1116 (e.g., as relevant to the received request) may be produced as well as other anonymized IDs 1012 may also be produced and assigned, that may be relevant to the at least some information in the received request, such that a given anonymized linkage record 1000 may then be formed that comprises this set of anonymized IDs 1012.

In some embodiments, step 1120 (see FIG. 11A) may comprise one or more of creating and/or updating anonymized linkage record 1000 from anonymized IDs 1012. In some embodiments, a given anonymized linkage record 1000 may be a set of instructions for mapping to the set of anonymized information 1116. Any given anonymized linkage record 1000 may comprise the set of relevant anonymized IDs 1012; which may map to the set of the anonymized information 1116.

In some embodiments, when the anonymized linkage record 1000 or the linkage record 600 may be updated, various methods may check the anonymized linkage record 1000 that has been updated to see if the update compromised anonymity of the anonymized information 1116. In some embodiments, if the update compromised the anonymity of the anonymized information 1116, then the method will re-anonymize the update; and then in some embodiments, re-check for sufficient anonymity.

FIG. 11D may depict a flow diagram of exemplary steps of an example of an opt-out procedure to convert linkage record 600 into at least one anonymized linkage record 1000 in accordance with one or more embodiments of the invention. FIG. 11D may depict steps in method 1122. In some embodiments, method 1122 may comprise steps: step 1124, step 1104a, step 1106, and step 1120. In some embodiments, method 1122 may comprise steps: step 1124, step 1104a, step 1106, step 1120, and step 1126. In some embodiments of method 1122, step 1126 may be: omitted, optional, or mandatory. In some embodiments, step 1124 may comprise receiving an opt-out request with respect to a linkage record 600 for any individuals claimed as part of the opt-out request. In some embodiments, the information provided in the request may comprise the opt-out request, such that upon receiving this information provided in the request, the anonymized linkage record 1000 may be generated. In some embodiments, step 1104a may be substantially similar to step 1104 as described above. In some embodiment, step 1104a may be limited to modifying segments 114, as opposed to modifying one or more genome sequences 110. Step 1106 and step 1120 may be as described above.

In some embodiments, step 1126 may comprise deleting the corresponding linkage record 600 or deleting an existing corresponding linkage record 600. In some embodiments, step 1126 may comprise deleting the corresponding linkage record 600 or deleting an existing corresponding linkage record 600; and deleting information 1114 that may have been mapped to. In some embodiments, such deletion may be from one or more of: one or more storage units 708, the databases, and/or the repositories. Note, in some embodiments, deletion of linkage record 600 and/or deletion of information 1114, may not proceed until anonymized linkage record 1000 and anonymized information 1116 may have been formed.

In some embodiments of step 1126, original data 101, i.e., one or more genome sequences 110 and the associated information 120, as well as one or more segments 114, the organizational units, fields 812, subfields 814, different subfields 816, categories 818, plurality of unique linkage record IDs 650, linkage records 600, and the existing linkage records 600 that may be relevant to the received opt-out request may be deleted from one or more of: one or more storage units 708, the databases, and/or the repositories. While, and prior to such deletion, the modified-genome-sequences, the modified-segments, the modified-organizational-units, the modified-subfields, the modified-categories, the modified-different-subfields, the anonymized IDs 1012, and/or the anonymized linkage records 1000 may be non-transitorily stored on one or more of: one or more storage units 708, the databases, and/or the repositories.

In some alterative embodiments of step 1126, original data 101, i.e., one or more genome sequences 110 and the associated information 120, as well as the one or more segments 114, the organizational units, fields 812, subfields 814, different subfields 816, categories 818, plurality of unique linkage record IDs 650, linkage records 600, and the existing linkage records 600 may be non-transitorily stored on only secure and encrypted media, such as the one or more of: one or more storage units 708, the databases, and/or the repositories. While the modified-genome-sequences, the modified-segments, the modified-organizational-units, the modified-subfields, the modified-categories, the modified-different-subfields, anonymized IDs 1012, and/or anonymized linkage records 1000 may be non-transitorily stored in formats that may not be secure nor encrypted.

In some embodiments, the method may provide access anonymized information 1116 by providing access to one or more of: the modified-genome-sequence, the modified-segments, the modified-organizational-units, the modified-subfields, the modified-categories, the modified-different-subfields, anonymized IDs 1012, and/or the anonymized linkage record 1000. In some embodiments, anonymized information 1116 may be accessible by one or more of the requestors who provided a given request.

For example, and without limiting the scope of the present invention, one or more of: the modified-genome-sequences, the modified-segments, the modified-organizational-units, the modified-subfields, the modified-categories, the modified-different-subfields, the anonymized linkage record, and/or the like may be made publically available or available by logging into a website with preapproved credentials.

In some embodiments, the method may provide controlled and/or limited access to information 1114. Although, in some embodiments, the mere process of: segmenting 400; dividing 805 fields 812 into subfields 814; generalizing 806 fields 812 into different subfields 816; and/or categorizing 807 fields 812 into categories 818 may provide some anonymity and in some instances may be sufficient to anonymize identity of the individual whose data and/or information was segmented 400 and/or organized 804.

In some embodiments, access to unmodified data and/or information, e.g., one or more genome sequences 110 and/or associated information 120, i.e. original data 101, that has yet to be processed, organized 804, and/or modified/anonymized (e.g., via steps 1104, 1104a, and/or 1110) may be denied or restricted. In some embodiments, access to information 1114 may not be possible due to, for example, deletion of the linkage record 600 or deletion of the existing linkage record 600; and/or deletion of information 1114 that may have been mapped to.

The FIG. 12 series of figures may comprise FIG. 12A through and including FIG. 12E. These FIG. 12 series of figures may address processes for processing a request for genetic study results of genetic variants (i.e., "genetic study results"), such as, but not limited to, GWAS results. For example, the request could be a specific GWAS request. In some embodiments, systems and/or methods may non-transitorily store various genetic study results. For example, and without limiting the scope of the present invention, such storage may be in one or more of: one or more storage units 708, databases, and/or in repositories. Such storage of genetic study results may be in a format of the various organizational units (see e.g., FIG. 8B). Such storage may be accessible and/or retrievable by use of relevant linkage records 600 and/or anonymized linkage records 1000.

Various requestors, which may be third parties, such as, but not limited to, genetic researchers, research organizations, research institutions, and the like may have various desires and/or needs to access at least some of the genetic study results. The FIG. 12 series of figures and this corresponding discussion may address how much requestors might submit requests to receive back the at least some of the genetic study results, how such requests may be processed to provide anonymized information versions of relevant records that may be relevant to the given request. In some embodiments, providing the at least some of the genetic study results may be provided in an anonymized format.

Note, in some embodiments, the genetic study results may be selected from one or more of: case-controlled studies, cross-sectional studies, longitudinal studies, and/or the like. That is, in terms of types of results, at least some of the genetic study results may be typed as one or more of: case-controlled studies, cross-sectional studies, longitudinal studies, and/or the like.

Case-controlled studies may comprise at least one control group and at least one experimental group. Experimental groups may differ from the control group by one variable—a variable which may be the subject of a given study. For example, all data in one experimental group may be associated with one or more of: a given disease, a given genetic condition, and/or a given phenotype of interest; whereas, data in a corresponding control group may not be associated with the one or more of the given disease, the given genetic condition, and/or the phenotype of interest. But other key variables may be shared between (across) the control group and the experimental group. For example, the control group and the experimental group might share age ranges, races, and/or ethnicities; but not share the give disease.

Whereas, cross-sectional studies may comprise data across an entire population at one point in time. And longitudinal studies may comprise data over a period of time. For example, a genetic study results may track percentage of people with a specific genome polymorphism that may also have Jaundice, where the tracking may be done every five years over a 40 year span.

Briefly, FIG. 12A may depict a flow diagram of exemplary steps for processing the request for the genetic study results of the genetic variants. FIG. 12A may depict method 1200 and its steps. FIG. 12B may depict a flow diagram of exemplary steps for processing the request for the genetic study results of the genetic variants. FIG. 12B may depict method 1200a and its steps. FIG. 12C may depict a flow diagram of exemplary steps for processing the request for the genetic study results of the genetic variants. FIG. 12C may depict method 1200b and its steps. FIG. 12D may depict a flow diagram of exemplary steps for processing the request for the genetic study results of the genetic variants; wherein the process may comprise a grouping step, as well as an aggregating grouping step for similar relevant segments. FIG. 12D may depict method 1214 and its steps. FIG. 12E may depict a flow diagram of exemplary steps for processing the request for the genetic study results of the genetic variants; wherein the process may comprise a grouping step, as well as an aggregating grouping step for similar relevant segments. FIG. 12E may depict method 1214a and its steps.

Turning back to a more detailed discussion of FIG. 12A. FIG. 12A may depict method 1200 and its steps. In some embodiments, method 1200 may be a method for processing a request for genetic study results of genetic variants from a plurality of different individuals. In some embodiments, method 1200 may comprise steps: step 1202, step 1204, and step 1212. In some embodiments, step 1202 may comprise receiving the request. In some embodiments, step 1204 may comprise finding relevant records that may be relevant to parameters in the request. In some embodiments, step 1212 may comprise providing anonymized information versions of the relevant records.

In some embodiments, the request may be an electronic and/or a digital record and/or file. In some embodiments, the request may comprise parameters, wherein such parameters may help to identify types of relevant information that a requestor may be requesting. In some embodiments, the parameters in the request may comprise one or more of: at least one segment location information, at least one segment sequence information, or information-of-interest. For example, and without limiting the scope of the present invention, the parameters in the request may comprise the at least one segment location information and at least some information-of-interest; however, that request might not comprise the at least one segment sequence information, as the at least one segment sequence information may be information that the requestor wants to obtain and may not presently have.

In some embodiments, the information-of-interest (e.g., a type of parameter in the request) may comprise one or more of: associated information 120, phenotype information 122, medical record information 124, personal information 126, a disease of interest, a genetic condition of interest, treatment results of interest, one or more types of medicine being studied, and/or portions thereof.

For example, and without limiting the scope of the present invention, the disease of interest may be a disease (e.g., diabetes) that the researcher (requestor) is studying and wants the genetic variants data (i.e., the genetic study results) for the plurality of different individuals that may all share some segment 114.

For example, and without limiting the scope of the present invention, in some exemplary embodiments, the information-of-interest may comprise the disease being studied and one or more of: an age range of interest, an ethnicity of interest, a race of interest, and/or the like.

For example, and without limiting the scope of the present invention, in some exemplary applications of method 1200 the parameters in the request may comprise at least one segment location information, the disease being studied, and one or more of: an age range of interest, an ethnicity of interest, a race of interest, and/or the like.

For example, and without limiting the scope of the present invention, in some exemplary applications of method 1200 the parameters in the request may comprise at least one segment location information, the disease being studied, one or more medicines being studied, and one or more of: an age range of interest, an ethnicity of interest, a race of interest, and/or the like.

In some embodiments, this request may be specific, by the specificity of the included parameters in the request. For example, and without limiting the scope of the present invention, a given request may be specific to one or more of: a specific disease, a specific treatment, a specific group of individuals, a specific nucleic acid sequence of interest (e.g., a specific segment 114), a specific geographical region, various specific phenotypes, a specific age, a specific gender, and/or the like.

In some embodiments, step 1204 of finding the relevant records may operates by the method (e.g., method 1200, 1200a, 1200b, 1214, and/or 1214a) substantially matching at least some information in the request to similar information non-transitorily stored in one or more of: one or more storage units 708, databases, and/or in repositories.

In some embodiments, the system and/or the method may search one or more of: one or more storage units 708, the databases, and/or the repositories for this similar information. In some embodiments, this similar information may comprise received genetic study results (see e.g., the FIG. 13 series of figures and the FIG. 13 series discussion below). For example, and without limiting the scope of the present invention, this similar information may comprise one or more of: segments 114 relevant to the location specified in the request, the disease being studied (and specified in the request), one or more medicines being studied (and specified in the request), the age range of interest (and specified in the request), the ethnicity of interest (and specified in the request), and/or the race of interest (and specified in the request). Note, use of "substantially" above may indicate that a match need not be a perfect match, but rather may be deemed a match if some predetermined similarity may be present, such as a similarity of 90% or more between the information being compared.

In some embodiments, a given relevant record selected from the relevant records may be deemed relevant if the given relevant record may comprise at least one segment 114 that may substantially match one or more of at least one segment location information or at least one segment sequence information in the parameters of the request.

In some embodiments, the relevant record selected from the relevant records may be deemed relevant if the relevant record may comprise at least one segment 114 that may substantially match one or more of at least one segment location information or at least one segment sequence information in the parameters of the request; and/or the relevant record may comprise at least some associated information 120 that may substantially match information-of-interest in the parameters of the request. Thus, such a relevant record may be a relevant linkage record 600 and/or a relevant anonymized linkage record 1000.

In some embodiments, step 1212 of providing anonymized information versions of the relevant records found in step 1204 may comprise one or more of: printing, publishing, displaying, and/or otherwise making this anonymized information accessible to the requestor and/or to those the requestor may grant access to. For example, and without limiting the scope of the present invention, this anonymized information may be printed and/or published; wherein publication may be publicly available and/or available to the requestor and/or to those the requestor may grant access to. For example, and without limiting the scope of the present invention, this anonymized information may be published to a database (with public access or accessible by the requestor and/or to those the requestor may grant access to), published to a downloadable file (accessible by the requestor), published to a website (with public access or accessible by the requestor and/or to those the requestor may grant access to), and/or the like.

In some embodiments, the anonymized information provided in step 1212 may comprise one or more of: the organizational units, fields 812, subfields 814, different subfields 816, categories 818, segments 114, the modified-genome-sequences, the modified-segments, the modified-organizational-units, the modified-fields, the modified-subfields, the modified-different-subfields, the modified-categories, combinations thereof, and/or the like.

In some embodiments, when the request for the genetic study results of genetic variants from the plurality of different individuals may specifically be a request for GWAS results, then the anonymized information provided in step 1212 back to the requestor may be whole genome sequence information. In some embodiments, when the request for the genetic study results of genetic variants from the plurality of different individuals may not be a specific request for GWAS results, then the anonymized information provided in step 1212 back to the researcher may still be whole genome sequence information. In any event, in some embodiments of step 1212, such whole genome sequence information, which may be non-transitorily stored as segments 114 or anonymized segments, may be provided in substantially non-segmented format.

Turning to a more detailed discussion of FIG. 12B. FIG. 12B may depict method 1200a and its steps. Method 1200a may comprise additional steps as compared to method 1200. Where method 1200 may comprise steps: step 1202, step 1204, and step 1212; method 1200a may comprise these same steps, plus disposed between step 1204 and step 1212, method 1200a may comprise steps: step 1206, step 1208, and step 1210. That is, in some embodiments, method 1200a may comprise steps: step 1202, step 1204, step 1206, step 1208, step 1210, and step 1212.

In some embodiments, step 1206 may comprise grouping the relevant records into at least one group. In some embodiments step 1206 may proceed after step 1204 but before step 1212.

In some embodiments, after finding the relevant records of step 1204, but before providing the anonymized information of step 1212, the method (e.g., method 1200a and/or method 1200b) may check the relevant records (which may be grouped into at least one group per step 1206) for anonymity in step 1208. If the relevant records may not be anonymous, then the method may anonymize the relevant records via step 1210 to produce the anonymized information and may then proceed with step 1212 of providing the anonymized information versions of the relevant records. Whereas, if the relevant records may be anonymized according to step 1208 anonymity check, then the method may proceed with the step of providing the anonymized information versions of the relevant records of step 1212. See e.g., FIG. 12B.

In some embodiments, step 1208 of checking if the relevant records may be anonymous may comprise analyzing the relevant records to determine if any given individual may be identifiable from the relevant records. In some embodiments, the relevant records may comprise one or more frequencies of occurrence associated with one or more traits in the relevant records. These one or more frequencies of occurrence may be compared against a predetermined threshold value, and if the one or more frequencies of occurrence may be greater than the predetermined threshold value, then relevant records may be deemed anonymous; and if the one or more frequencies of occurrence may be less than or equal to this predetermined threshold value, then the relevant records may be deemed not anonymous.

In some embodiments, the one or more frequencies of occurrence may be identified by one or more of: statistical information 640, personal information 642, genome segments 644, phenotype 646, and/or medical record 648, as discussed in the FIG. 6 discussion above.

In determining a given predetermined threshold value to use in an anonymity check of step 1208, that given predetermined threshold value may be a function of a nature of the trait in relation to a particular population size. For example, the trait may be a phenotype, such as eye color and in particular green eyes. A frequency of green eyes in one population (e.g., a Scandinavian village) may not compromise anonymity because of a lack of rarity (i.e., green eyes may be sufficiently common in such a population of that Scandinavian village); whereas, a frequency of green eyes in another population (e.g., a Chinese village) may compromise anonymity because of rarity with respect to that particular relevant population. In some embodiments, different predetermined threshold values may be used for different traits and/or for different population sizes.

In some embodiments, the one or more frequencies of occurrence may be multiplied together to produce a resulting product frequency. That is, this resulting product frequency may be calculated in a same or similar manner as total probability 330 of FIG. 3 and the FIG. 3 discussion above. In some embodiments, the resulting product frequency may be compared against the predetermined threshold value, and if the resulting product frequency may be greater than the predetermined threshold value, then relevant records may be deemed anonymous; whereas, if the resulting product frequency may be less than or equal to the predetermined threshold value, then the relevant records may be deemed not anonymous.

However, as known in the statistical arts, presence of a small population size may introduce errors. For example, consider the green eyes in the Chinese village example. If there may be one family in that village routinely producing green eyes, but the overall population size for that Chinese village is small enough, then the frequency of green eyes in that village may be relatively high as compared to neighboring Chinese villages, such that an anonymity check against the predetermined threshold may yield a result that indicates the relevant records are anonymous when in fact those relevant records may be used to identify that particular Chinese family. Thus, the anonymity check of step 1208, in some embodiments, may comprise a further limitation in that if a frequency of occurrence may be from a small sample size, then that frequency of occurrence may be eliminated from use in the anonymity check of step 1208, to reduce a chance of introducing small population size errors. That is, in some embodiments, the frequency of occurrence used in the anonymity check of step 1208 must be of a sufficiently large population size. In some embodiments, the one or more frequencies of occurrence may be from sufficiently large population sizes to reduce introducing small population size error.

Note, if the relevant records may have already been anonymized, then such anonymized relevant records may be deemed "anonymized information." Likewise, if the relevant records may not be anonymized and may require anonymization prior to step 1212, the output of such anonymization (e.g., via step 1210) may be deemed "anonymized information."

In some embodiments, the step 1210 of anonymizing the relevant records may comprise creating anonymized linkage record 1000 from the relevant records (and/or utilizing a preexisting relevant anonymized linkage record 1000 mapping to the relevant records). See e.g., FIG. 10 and the FIG. 11 series figures and their discussions.

In some embodiments, step 1210 of anonymizing the relevant records may comprise one or more of: segmenting one or more genome sequences 110 into one or more segments 114; modifying one or more genome sequences 110 into the modified-genome-sequences;

modifying one or more segments 114 into the modified-segments; modifying the organizational units into the modified-organizational units; modifying fields 812 into the modified-fields; dividing 805 fields 812 into subfields 814; generalizing 806 fields 812 into different subfields 816; categorizing fields 807 into categories 818; modifying subfields 814 into the modified-subfields, modifying categories 818 into the modified-categories; and/or modifying different-subfields 816 into modified-different-subfields.

In some embodiments, the modifying of one or more genome sequences 110 or the modifying of one or more segments 114 may be done by one or more of: deleting, inserting, appending, and/or replacing one or more nucleotides; and/or by using the nucleotide nomenclature system to specify sequences of nucleotides. For example, and without limiting the scope of the present invention, the nucleotide nomenclature system may be the IUB/IUPAC standard nucleotide nomenclature system.

In some embodiments, the modifying of the one or more of the organizational units, fields 812, subfields 814, different subfields 816, and/or categories 818 may be done by one or more of: deleting, inserting, appending, or replacing some of the data in the relevant records.

In some embodiments, the anonymized information provided in step 1212 may comprise one or more of: the organizational units, fields 812, subfields 814, different subfields 816, categories 818, segments 114, the modified-genome-sequences, the modified-segments, the modified-organizational-units, the modified-fields, the modified-subfields, the modified-different-subfields, the modified-categories, combinations thereof, and/or the like.

Turning to a more detailed discussion of FIG. 12C. FIG. 12C may depict method 1200b and its steps. FIG. 12C may differ from FIG. 12B, in that where method 1200a in FIG. 12B may comprise step 1206; method 1200b in FIG. 12C may comprise step 1206b instead of step 1206. Otherwise, method 1200a (of FIG. 12B) and method 1200b (of FIG. 12C) may share substantially same steps.

In some embodiments, step 1206b may comprise a step of grouping the relevant records into one of at least two groups, a control group and at least one experimental group. That is, in some embodiments, step 1206b may produce at least two groups, the control group and the at least one experimental group. Note however, that while step 1206b may produce at least two groups, depending upon the parameters in the request, only one such group may be provided in step 1212.

In some embodiments, after step 1204 of finding the relevant records, but before step 1212 of providing the anonymized information versions of the relevant records, the method (e.g., method 1200b) may comprise step 1206b of grouping the relevant records into one of the at least two groups, the control group and the at least one experimental group. See e.g., FIG. 12C.

In some embodiments, the control group and the at least one experimental group may share at least one common variable. In some embodiments, the at least one experimental group may have at least one different variable, wherein this at least one different variable may not be within the control group. For example, and without limiting the scope of the present invention, a control group and an experimental group both may comprise people with high blood pressure, i.e., the at least one common variable may be high blood pressure in this example. However, the experimental group may further comprise people with high blood pressure and that have a BMI (body mass index) of over 30; while the control group may comprise people with high blood pressure but that do not have the BMI of over 30; thus the BMI of over 30 may the at least one different variable in this example.

In some embodiments, the at least one common variable may be selected from one or more of: at least some sequence-associated-information 112, at least one segment location (i.e., at least one segment location information), and/or at least some associated information 120.

Also note, in some embodiments, there may be no at least one common variable, but there may still be at least one different variable to distinguish between a given control group and the at least one experimental group.

In some embodiments, a given experimental group may comprise relevant records that further comprise one or more of: a disease being studied or a phenotype of interest; and wherein the control group may comprise relevant records that do not include the one or more of: the disease being studied or the phenotype of interest. That is, in some embodiments, the at least one different variable may be the disease being studied and/or the phenotype of interest. Note, the disease being studied may be the disease of interest of the information-of-interest, of the parameters, of the request. And the phenotype of interest may be the phenotype information 126 of the information-of-interest, of the parameters, of the request.

In some embodiments, the at least one experimental group may comprise at least one whole genome sequence (e.g., one or more genome sequences 110) associated with the at least one different variable. In some embodiments, the at least one whole genome sequence may be non-transitorily stored as one or more segments 114.

In some embodiments, in method 1200b, step 1212 of providing anonymized information versions of the relevant records, may comprise providing the anonymized information versions as grouped into at least two groups of the control group and the at least one experimental group.

In some embodiments, in method 1200b, step 1212 of providing the anonymized information versions of the relevant records, may comprise providing the anonymized information versions as grouped in one or more of: the control group and/or the at least one experimental group. In some embodiments, the anonymized information of the control group and/or the experimental group may be provided to the requestor of the request in step 1212.

In some applications a given requestor may be planning to conduct their own genetic study and may need relevant control group data for their planned study. In such applications, the requestor may specific by the parameters in the request a desire for only control group data. And then in step 1212 only the control group produced in step 1206b may be provided. For example, in some applications of method 1200b of FIG. 12C (and/or method 1214a in FIG. 12E), a given researcher (i.e., the given requestor) may only be interested in segment location and segment sequence information of the control group, in which case, only such anonymized information versions of that control group may be provided to that given researcher in step 1212 (and/or in step 1220 of method 1214a). For example, this may apply to when the given researcher plans to test and study a novel medicine and/or a novel treatment modality, and this given researcher may need an appropriate control group. For this test and study that this given researcher plans, data for the experimental group may not yet exist and may be generated by that given researcher's test and study.

However, other requestors may want both control group and experimental data and thus step 1212 may provide both the control group and the at least one experimental group, pursuant to relevant parameters in the request. For example, in some other applications of method 1200b of FIG. 12C (and/or method 1214a in FIG. 12E), a different given researcher (i.e., the other requestor) may be interested in both control group and experimental group(s). This may be a situation when that different given researcher may be more interested in studying the relevant (and anonymized) segment location and sequence information of segments 114 or of one or more genome sequences 110. In such applications of some embodiments, the at least one different variable may be the disease being studied.

Turning to a more detailed discussion of FIG. 12D. FIG. 12D may depict method 1214 and its steps. Method 1214 of FIG. 12D may comprise additional steps and/or replacement steps as compared to method 1200a (shown in FIG. 12B). Method 1214 may comprise steps of: step 1202, step 1204, step 1206a, step 1216, step 1218, and step 1220. Step 1202 and step 1204 in method 1214 (of FIG. 12D) may be as described above for methods 1200, 1200a, and 1200b (of FIG. 12A, FIG. 12B, and FIG. 12C, respectively). Step 1206a in method 1214 may replace step 1206 in method 1200a. In some embodiments, step 1206a may comprise grouping the relevant records (produced by step 1204) into at least two separate groups. Whereas, recall step 1206 may comprise grouping the relevant records into at least one group. Step 1220 in method 1214 may replace step 1212 in method 1200a.

In some embodiments, step 1216 and step 1218 may operate to produce relevant segments 114 that may be relevant to at least some of the parameters in the request. In some embodiments, such relevant segments 114 may be anonymized segments. This may be accomplished by step 1216 finding and/or creating linkage record(s) 600 that may then be used to identify the relevant segments 114. See e.g., FIG. 6 and the FIG. 8 series of figures, as well as their corresponding discussion in forming, updating, and utilizing linkage records 600. And step 1218 may then comprise anonymizing each (or at least one) such identified relevant segment 114. In some embodiments, step 1216 and step 1218 may be replaced by steps utilized to produce anonymized linkage records 1000 and anonymized segments 114, see e.g., FIG. 10 and the FIG. 11 series of figures, as well as their corresponding discussion, such as step 1104 and/or step 1110.

In some embodiments, after grouping the relevant records into the at least two separate groups of step 1206a, the method (e.g., method 1214) may perform step 1216 of finding and/or creating linkage record(s) 600 with respect to at least one segment 114 associated with the relevant records. Such at least one segment 114 that may be associated with the relevant records may be deemed a relevant segment 114. In some embodiments, relevant segments 114 may be relevant because such relevant segments 114 may all share a common segment location; which may have identified and/or specified in the parameters of the request.

In some embodiments, step 1218 may anonymize each of the at least one segments 114 associated with the relevant records. In some embodiments, step 1218 may anonymize each of the relevant segments 114. In some embodiments, step 1218 may anonymize at least one of the relevant segments 114. In some embodiments, such anonymization may proceed by step 1104 and/or by step 1110.

In some embodiments, step 1220 of providing the anonymized information may comprise providing the relevant segments 114 that have been anonymized (e.g., via step 1218) in at least one aggregate group of anonymized segments for one or more of: the control group or the experimental group. Each such of the at least one aggregate group of anonymized segments 114 may share a common segment location.

In some embodiments, the at least one aggregate group of anonymized segments 114 may comprise a table populated with data. In some embodiments, such a table may comprise the common segment location. In some embodiments, such a table may comprise each anonymized segment 114 of the at least one aggregate group of anonymized segments denoted as a single nucleotide polymorphism (SNP) along with a given frequency for that single nucleotide polymorphism within that at least one aggregate group of anonymized segments.

For example, and without limiting the scope of the present invention, pursuant to the steps of method 1214 (and/or method 1214a) processing of a given request for the genetic study results of the genetic variants from the plurality of different individuals may result in providing a plurality of such tables, wherein each such table may comprise aggregated anonymized segments relating a common segment location for that given table. A single individual, from that plurality of different individuals, may then have their entire genome (minus modifications dues to anonymization) split up amongst these plurality of tables. However, even one with access to a totality of this plurality of tables may not be able identify any of the different individuals.

In some embodiments, the data (populating the tables) may further comprise sequence-associated-information 112 for any of the anonymized segments 114 of the at least one aggregate group of anonymized segments.

In some embodiments, the data (populating the tables) may further comprise frequencies of the at least one segments 114 associated with the relevant records (i.e., the relevant segments 114) with respect to a given population greater than the at least one aggregate group of anonymized segments.

In some embodiments, the data (populating the tables) may further comprise at least one overall frequency. The at least one overall frequency may be with respect to one or more of: the each anonymized segment of the at least one aggregate group of anonymized segments; the single nucleotide polymorphisms (SNPs); and/or at least some of the sequence-associated-information 112. Note, in this context, "overall frequency" may refer to the frequency of a given trait or characteristic with respect to an entire population, which in some embodiments, the entire population may be larger than a population size of the database, the repository, and/or one or more storage unit 708. Thus, in some embodiments, "overall frequency" may be an imported frequency from a given entire population.

Turning back to a more detailed discussion of FIG. 12E. FIG. 12E may depict method 1214a and its steps. Method 1214a of FIG. 12E may be similar to method 1214 of FIG. 12D; except in method 1214a there may be step 1206b rather than step 1206a. In some embodiments, method 1214a may comprise steps: step 1202, step 1204, step 1206b, step 1216, step 1218, and step 1220. Step 1202, step 1204, step 1216, step 1218, and step 1220 may be as described and discussed above.

In some embodiments, step 1206b may comprise grouping the relevant records into the at least two groups of the control group and the at least one experimental group. In some embodiments, after grouping the relevant records into the control group or the at least one experimental group of step 1206b, the method (e.g., method 1214a) may perform step 1216 of finding and/or creating linkage record(s) 600 with respect to at least one segment 114 associated with the relevant records. Such at least one segment 114 that may be associated with the relevant records may be deemed a relevant segment 114. In some embodiments, relevant segments 114 may be relevant because such relevant segments 114 all share a common segment location.

While the above FIG. 12 series of figures discussion may have addressed how various methods and/or systems may process the request to provide genetic study results in a manner that mitigates identification of individuals; the FIG. 13 series of figures may focus on how genetic study results may be received and processed by various methods and/or systems of the invention. The FIG. 13 series of figures may comprise FIG. 13A through and including FIG. 13C. These FIG. 13 series of figures may address a process for processing received genetic study results.

The FIG. 13 series of figures may depict flowcharts of various steps in method 1300, method 1314, and combinations thereof for receiving various genetic study results, i.e., for receiving at least one result. For example, and without limiting the scope of the present invention, in some embodiments, the genetic study results may be results from a GWAS study, i.e., GWAS results. In some embodiments, the genetic study results may not be GWAS results. In some embodiments, the at least one received result may comprise results-information that may summarize and/or demonstrate various patterns found in various segments 114 (and/or whole genome sequences 110) that may have been analyzed in a given genetic study. That is, such patterns may be of statistical linkages (i.e., associations) between certain segments 114 and various disease(s), phenotypes, and/or genetic conditions studied in the given genetic study.

Thus presence of such certain segments 114 in a given person's genome, may indicate predispositions for the various disease(s), genetic conditions, and/or certain phenotypes. Such received results may be sought by a patient or a healthcare provider of that patient in seeking some personalized medicine recommendation as noted in the FIG. 14 series of figures and that FIG. 14 series of figures discussion as discussed below. For example, and without limiting the scope of the present invention, a given genetic researcher may provide genetic study results according to method 1300, method 1314, combinations thereof and/or at least one of the FIG. 13 series figures, wherein those received results may yield a recommendation for a best medicine or treatment modality for specific polymorphisms associated with a given disease of interest. Likewise, a given genetic researcher may provide genetic study results according to method 1300, method 1314, combinations thereof, and/or at least one of the FIG. 13 series figures, wherein those received results may convey certain percentage (or similar statistical linkages) predispositions for the various disease(s), genetic conditions, and/or phenotypes associated with sequence or segment information in the received results.

Briefly, FIG. 13A may depict a flow diagram of exemplary steps for processing the received genetic study results. FIG. 13A may depict method 1300 and its steps. FIG. 13B may depict a flow diagram of exemplary steps for processing the received genetic study results. FIG. 13B may depict method 1314 and its steps. Method 1314 may comprise additional steps as compared to method 1300. FIG. 13C may depict additional steps for checking and/or anonymizing the received genetic study results that may be incorporated into various embodiments of method 1300 and/or method 1314.

Turning back to a more detailed discussion of FIG. 13A and method 1300. FIG. 13A may depict method 1300. Method 1300 may be a method for processing genetic study results. In some embodiments, method 1300 may comprise steps of: step 1302, step 1306, and step 1312. In some embodiments, step 1302 may comprise a step of receiving at least one result. In some embodiments, the at least one result once received may be deemed at least one received result. In some embodiments, at least one received result may comprise results-information. In some embodiments, step 1306 may comprise a step of cataloging the results-information into cataloged-results-information. That is, step 1306 may catalog the at least one received result. In some embodiments, step 1312 may comprise a step of non-transitorily storing the cataloged-results-information (i.e., the cataloged at least one received result) in one or more of: one or more storage units 708, the databases, and/or the repositories.

In some embodiments, the results-information may comprise one or more of: at least one genome sequence 110 from at least one individual; at least one segment 114 of the at least one individual; sequence-associated-information 112 of the at least one genome sequence 110 and/or of the at least one segment 114; at least one marked allele of the at least one individual; and/or information-of-interest. In some embodiments, the at least one marked allele may indicate that this allele (or alleles) may associate with one or more of: a disease of interest, a genetic condition of interest, and/or a phenotype of interest at some minimal frequency. In some exemplary embodiments, the results-information may at least comprise the at least one marked allele and at least some of the information-of-interest.

In some embodiments, the information-of-interest may comprise one or more of: at least some associated information 120; at least some phenotype information 122; at least some medical record information 124; at least some personal information 126; a disease of interest; a genetic condition of interest; treatment results of interest per the at least one individual; or results of a given genetic study.

In some exemplary embodiments, the at least one result may comprise a plurality of results for a plurality of individuals. Collectively, step 1302 may involve receiving the plurality of results, with one result for each individual in a given genetic study results received. Each such result selected from the plurality of results may in total (i.e., in aggregate) comprise the at least one result. And/or, step 1302 may entail receiving at least one result, wherein the at least one result may pertain to the plurality of individuals (which may be different individuals). Thus in some applications of method 1300 and/or method 1314, there may be a plurality of information-of-interest. And thus there may be a plurality for each of the at least some associated information 120, the at least some phenotype information 122, the at least some medical record information 124, the at least some personal information 126, the diseases of interest, the genetic conditions of interest, the treatment results of interest, and/or the like that may make up the plurality of the information-of-interest for the plurality of individuals. Thus, in some embodiments, the treatment results of interest may be total results for a given genetic study of the plurality of individuals. Likewise, there may then be a plurality of sequences 110 and/plurality of segments 114 received from a given researcher and/or research institution. It may be this collective body of information that step 1302 may receive and that step 1306 (or step 1306a) may then catalog. In some embodiments, at least some of this collective body of information may be accessed and/or utilized by others. For example, and without limiting the scope of the present invention, at least some associated information 120 and/or segments 114 of the at least one result may be used as key(s) to later retrieve such results-information as pertinent records in applications of the FIG. 14 series of methods.

Note, in some embodiments, the at least one genome sequence 110 may be selected from one or more of: one or more genome sequences 110; one or more segments 114 derived from the one or more genome sequences 110; modified-genome-sequences derived from the one or more genome sequences 110; and/or modified-segments derived from the one or more segments 114.

Turning to a more detailed discussion of FIG. 13B and method 1314. FIG. 13B may depict method 1314. Method 1314 may be a method for processing genetic study results. In some embodiments, method 1314 may comprise steps of: step 1302, step 1304, step 1306a, and step 1312a. As compared to method 1300, method 1314 may comprise additional step 1304; and method 1314 may substitute step 1306a for 1306; and method 1314 may substitute step 1312a for step 1312. Step 1302 in method 1314 may substantially similar to step 1302 in method 1300, i.e., a receiving step.

In some embodiments, step 1304 may comprise a step of associating at least one marked allele with at least one relevant segment. In some embodiments, step 1306a may comprise a step of cataloging the received results and/or cataloging the association. So step 1306a may be a cataloging step, similar to step 1306, but in step 1306a, the association may also be cataloged. In some embodiments, step 1312a may comprise a step of non-transitorily storing the cataloged-results-information and/or non-transitorily storing the association in one or more of: one or more storage units 708, the databases, and/or the repositories. So step 1312a may be a non-transitory storage step, similar to step 1312, but in step 1312a, the association (and/or a marking) may also be non-transitorily stored.

The at least one genome sequence 110 from the at least one individual and/or the at least one segment 114 from the at least one individual may be marked at at least one locus. This marking may be the at least one marked allele. This marking of the at least one locus may indicate that one or more of: the disease of interest, the genetic condition of interest, and/or the phenotype of interest associates with the at least one locus, e.g., at some minimal frequency. Recall, the at least one genome sequence 110 from the at least one individual and/or the at least one segment 114 from the at least one individual may be types of results-information of the at least one received result of step 1302. And the at least one marked allele may also be a type of results-information of the at least one received result of step 1302.

In some embodiments, after step 1302 of receiving the at least one received result, but before step 1306a of cataloging, the method (e.g., method 1314) may comprise step 1304 of associating the at least one marked allele with at least one relevant segment 114. The at least one relevant segment 114 may be relevant if the at least one segment 114 may comprise an allele or some nucleic acid sequence that may match the at least one marked allele.

In some embodiments, step 1304 of associating may comprise marking the at least one relevant segment 114 at the at least one locus on the at least one relevant segment 114 that may indicate a location of the allele or of the some nucleic acid sequence on the at least one relevant segment 114 that may match the at least one marked allele.

For example, and without limiting the scope of the present invention, in some embodiments the results-information of the at least one received result may include the at least one marked allele of the least one individual. This marking may be on the at least one genome sequence 110 from the at least one individual and/or this marking may be on the at least one segment 114 of the at least one individual that may be received as part of the results-information. Note, such marking may be done by the researcher and/or attributed to the research group who had provided the at least one received result. Additionally, this marking may be received either in physical marked nucleic acid format and/or a digital representation of such physical nucleic acid marking. Further note, that various method and/or system embodiments of the present invention may equivalently associate and/or mark the at least one relevant segment 114 to denote equivalent location(s) in the at least one relevant segment 114 that correspond to locations marked in the at least one marked allele of the least one individual. Likewise, various method and/or system embodiments of the present invention may non-transitorily store digital representations of such association(s) and/or marking(s) in the at least one relevant segment 114. Also, in some applications, note there may not be a need for the method and/or system to associate and/or mark the at least one relevant segment 114.

Note, in some embodiments, this at least one relevant segment 114 may not be a segment 114 from any one individual. Associating and/or marking this at least one relevant segment 114 may be for at least a purpose of storing information about at least one locus of nucleotide regions of interest and/or allele(s) of interest that may be linked to one or more of a given disease, a given genetic condition, and/or some phenotype of interest. This at least one relevant segment 114 may be selected from one or more of: an arbitrary segment of the least one individual; a non-arbitrary segment of the least one individual; an anchor segment 510 (associated with a linkage record 600 used); a "blank segment" created specifically for a purpose of storing information about the at least one locus of nucleotide regions of interest and/or allele(s) of interest; the align sequence(s) (see FIG. 4 series discussion above), and/or some preexisting segment.

In this context, the "arbitrary segment" may simply mean the at least one relevant segment 114 that may be associated and/or marked, may be chosen on a random basis. Whereas, the "non-arbitrary segment" may mean the at least one relevant segment 114 that may be associated and/or marked, may be chosen on a non-random basis. For example, and without limiting the scope of the present invention, the at least one relevant segment 114 may be chosen (or generated) on a basis that is statistically least likely to require modification in order to preserve anonymity, i.e., including sequences in the at least one relevant segment 114, in addition to the marked sequences, that may be statistically common with respect to a certain population. For example, and without limiting the scope of the present invention, the "linkage record 600 used" may be respect to a linkage record 600 used to generate segments 114 that may have been provided to researcher(s) pursuant to a method of the FIG. 12 series of figures.

In some embodiments, the marking of the at least one relevant segment 114 may be facilitated by using a given align sequence (or align segment) to align the at least one marked allele with the at least one relevant segment 114; to minimize errors that might arise by marking the at least one relevant segment 114 in an incorrect location if aligning the at least one marked allele to the at least one relevant segment is not carried out. In some embodiments, the align segment and the at least one relevant segment 114 may be the same segment.

Turning to a more detailed discussion of FIG. 13C. FIG. 13C may comprise two additional steps of step 1308 and step 1310, which in some embodiments, may occur after step 1306 (or step 1306*a*) and/or after step 1312. Step 1308 may be an anonymity check step. And step 1310 may be an anonymizing step. If step 1308 determines that what was checked may not be anonymous, then step 1308 may proceed to step 1310 to anonymize what was checked. And once anonymized pursuant to step 1310, step 1310 may then feed back into step 1308 to re-check for anonymity. Once step 1308 finds there may be anonymity, then step 1308 may proceed to step 1312 (or to step 1312*a*) of the non-transitory storage.

In some embodiments, step 1308 (e.g., of FIG. 13C) may be a sub-step of the cataloging steps of 1306 or 1306*a*. In some embodiments, step 1306 (or step 1306*a*) of cataloging the results-information may further comprise scanning the results-information for information that compromises anonymity of at least one individual. This scanning anonymity check may be step 1308.

Or alternatively, in some embodiments, such a scanning anonymity check may be a standalone step 1308, which may be performed after step 1306 (or step 1306*a*) or after step 1312.

In some embodiments, step 1308 of checking if the results-information may be anonymous may comprise analyzing the results-information to determine if any given individual may be identifiable from the results-information. In some embodiments, this may entail analyzing the at least one genome sequence 110 of one individual and/or the at least one segment 114 of that one individual for sequence-associated-information 112 that may be associated with identifying the individual. For example, the more rare (with respect to some larger population) one or more variations (e.g., one or more polymorphisms) are in the at least one genome sequence 110 of one individual or the at least one segment 114 of that one individual, the more likely there may be risk that the individual may be identified. And this may require anonymizing the at least one genome sequence 110 of one individual or the at least one segment 114 of that one individual. This may also entail deleting the linkage record 600 or what was formerly an anonymized linkage record 1000, that may be affected by information that may result in revealing an identity.

In some embodiments, step 1308 may be scanning (checking) one or more of: the at least one received result from step 1302, the received results-information from step 1302, the cataloged results-information from step 1306 (or from step 1306*a*), the associated and/or marked at least one relevant segment 114 from step 1304, and/or any of these which may have already been non-transitorily stored per step 1312 (or step 1312*a*).

For example, and without limiting the scope of the present invention, such information that may compromise anonymity of the at least one individual may be one or more sequences 110 and/or one or more segments 114 received in the results-information, wherein such received sequence information (i.e., of one or more sequences 110 and/or one or more segments 114) may have a frequency versus a given population that identifies that sequence information as rare, such that due to that rarity, there may be an increased likelihood of identifying the at least one individual. Also note, that such sequence information may at one point in time may be deemed safe without compromising anonymity, but may later in time as more genetic study results are received, become sequence information that may compromise anonymity of the at least one individual. Which is why step 1308 of the anonymity check may need to be performed periodically.

In some embodiments, periodically, after step 1312 (or of step 1312a) of non-transitorily storing the cataloged-results-information (and/or non-transitorily storing the cataloged association), the method (e.g., method 1300 and/or method 1314) may comprise scanning the cataloged-results-information (and/or scanning the cataloged association) for information that compromises anonymity of at least one individual. This scanning anonymity check may be step 1308.

In some embodiments, this periodically, may be predetermined by the system and/or method and may be some discrete block of time. For example, and without limiting the scope of the present invention, this discrete block of time may be selected from every half second to every year. That is, in some embodiments, the system and/or the method may periodically perform this scanning check anywhere from every half second up to and including every year. In some embodiments, other discrete blocks of time may be employed. In some embodiments, this periodically, may be on a basis of some triggering event. For example, and without limiting the scope of the present invention, this triggering event may be anytime the system and/or the method receives genetic study results under step 1302.

In some embodiments, if at least some of the information scanned in step 1308 may reveal an anonymity problem, then the method may proceed to anonymize the at least some of the information via step 1310.

For example, and without limiting the scope of the present invention, a region of "junk DNA" for a given segment 114 of some specific individual may be received (e.g., via step 1302), and within that "junk DNA" may be one or more sequences of nucleotides that may be rare enough to provide a possible compromise in revealing that specific individual's identity. What may have formerly been an anonymized linkage record 1000, may become a linkage record 600 that may need to be deleted; and/or that given segment may need to be anonymized (modified).

Also note, that a determination that this DNA may be junk and/or that this one or more sequences of nucleotides may be rare, may be a determination that occurs after this given segment 114 may have been received via step 1302. For example, as a byproduct of additional genetic study research and receiving additional genetic study results that may occur at some point in the future. Thus, there may be a need to periodically scan per step 1308 the one or more databases, repositories, and/or one or more storage units 708 for data that may become at risk for revealing identities as further research is conducted, cataloged, and stored.

In some embodiments, when various methods and/or systems carries out an anonymity check (such as step 1308 and/or of step 1208) and that check indicates an anonymity problem then one or more of the following may be done: a warning message may be generated and/or transmitted; generation of a log entry memorializing the anonymity check's findings; and/or proceeding to an anonymization step (such as step 1310, step 1210, step 1104, and/or step 1110).

In some embodiments, if the results-information (e.g., received in step 1302) may be determined to not be anonymous, then the method and/or the system may send a warning to the provider of the genetic study results. Irrespective of such a warning, in some embodiments, if the results-information may be determined to not be anonymous per step 1308, then the method and/or the system may anonymize the results-information via step 1310 producing anonymized results-information. Whereas, in some embodiments, the method and/or the system may not proceed with step 1310 of anonymizing the results-information without receiving approval from the provider, which may have been requested in the warning.

In some embodiments, step 1310 (e.g., of FIG. 13C) of anonymizing the at least some of the information of the at least one received result (or of the results-information) may comprise creating (or updating) an anonymized linkage record 1000 from the results-information according to at least one of methods and/or steps of the FIG. 11 series of figures as discussed above.

In some embodiments, step 1310 of anonymizing the at least some of the information of the at least one received result (or of the results-information) may comprise one or more of: modifying one or more genome sequences 110 into modified-genome-sequences; modifying one or more segments 114 into modified-segments; modifying organizational units into modified-organizational-units; segmenting one or more genome sequences 110 into one or more segments 114; dividing 805 fields 812 into subfields 814; generalizing 806 fields 812 into different-subfields 816; categorizing 807 fields 812 into categories 818; modifying subfields 814 into modified-subfields; modifying different-subfields 814 into modified-different-subfields; and/or modifying categories 818 into modified-categories.

In some embodiments, the modifying of the one or more genome sequences 110 or of the one or more segments 114 may be done by one or more of: deleting, inserting, appending, or replacing one or more nucleotides, and/or by using a nucleotide nomenclature system to specify sequences of nucleotides. For example, and without limiting the scope of the present invention, the nucleotide nomenclature system may be the IUB/IUPAC standard nucleotide nomenclature system and/or a similar nomenclature system.

In some embodiments, the modifying of the one or more of: the organizational units, fields 812, subfields 814, different subfields 816, and/or categories 818 may be done by one or more of: deleting, inserting, appending, or replacing some of the data in the results-information. In some embodiments, the modifying of the one or more of: the organizational units, fields 812, subfields 814, different subfields 816, and/or categories 818 may be done by one or more of: deleting, inserting, appending, or replacing some of the data in the one or more of: the organizational units, fields 812, subfields 814, different subfields 816, and/or categories 818, respectively.

In some embodiments, the anonymized results-information produced by step 1310 may comprise one or more of: subfields 814, different subfields 816, categories 818, segments 114, the modified-genome-sequences, the modified-segments, the modified-organizational-units, the modified-fields, the modified-subfields, the modified-different-subfields, and/or the modified-categories.

The FIG. 14 series of figures may comprise FIG. 14A through and including FIG. 14G (i.e., seven figures). These FIG. 14 series of figures may address processes for generating personalized information of interest pertaining to at least one individual, such as, but not limited to, generating a personalized healthcare recommendation for that at least one individual.

Note, presently from a prior art problem perspective, at least one present problem in the area of personalized feedback from an individual's own personal genome is information overload, as well as the individual receiving information that the individual may not even want to know. For example, presently in various prior art implementations, the individual would submit their entire genome and receive a report back (e.g., with analysis broken down per chromosome), and may generally contain not only too much information, but information that the individual may not even want to know about themselves. Whereas, methods addressed in the FIG. 14 series of figures may provide to this individual only learn specifics pertinent to this individual's inquiry (in the form of a request), thus eliminating the problem of information overload and/or of the problem of providing information that the individual may not want to know.

For example, and without limiting the scope of the present invention, this individual may want to only know predisposition for a specific heart disease, but may not want to know any other personalized information determinable from analysis of the individual's own genome; and by using method and/or system embodiments of the present invention only the specifically requested personalized information of interest may be reported back to the individual, i.e., the predisposition for the specific heart disease. Furthermore, the personalized information of interest may be selected from one or more of: at least one predisposition for developing a given disease; at least one predisposition for developing a given phenotype; at least one personalized healthcare recommendation; and/or genetic research results. Thus the individual may be able to determine how much or how little personalized information of interest that the individual might learn from information codified in the individual's own genome. This may require receiving specific segment(s) 114 from the individual that may be pertinent to the personalized information of interest.

Briefly, describing each FIG. 14 series figures in this paragraph. FIG. 14A may depict a flow diagram of exemplary steps for generating the personalized information of interest pertaining to the at least one individual which may be triggered by receiving a request for the personalized information of interest. FIG. 14A may depict method 1400. FIG. 14B may depict a flow diagram of exemplary steps for generating the personalized information of interest pertaining to the at least one individual which may be triggered by receiving the request for the personalized information of interest. FIG. 14B may depict method 1402. Method 1402 may share beginning (i.e., a receiving step) and ending steps (i.e., a presenting step) with method 1400, but may have different middle steps as compared to method 1400. FIG. 14C may depict a flow diagram of exemplary steps for generating the personalized information of interest pertaining to the at least one individual which may be triggered by receiving the request for the personalized information of interest. FIG. 14C may depict method 1403. Method 1403 may be a more detailed embodiment of method 1402. Method 1403 may depict additional steps disposed between a step 1408 and a step 1424; and may provide for optional filtering step(s) prior to ending the method in the presenting step. FIG. 14D may depict a flow diagram of exemplary steps for generating the personalized information of interest pertaining to the at least one individual which may be triggered by receiving the request for the personalized information of interest. FIG. 14D may depict method 1404. Method 1404 may be a combination of method 1400 and method 1402, as well as some additional steps to facilitate integration of method 1400 with method 1402. FIG. 14E may depict a flow diagram of exemplary steps for receiving sequence information of at least one segment 114. FIG. 14E may depict additional steps 1406, which may comprise a series of steps after step 1434 but before an ending presenting step. These additional steps 1406, in some embodiments, may be integrated into method 1400 (FIG. 14A) and/or into method 1404 (FIG. 14D), as both methods include step 1434. FIG. 14F may depict a flow diagram of exemplary steps for narrowing and/or filtering pertinent records. FIG. 14F may depict optional steps 1454. Optional steps 1454 may comprise some additional steps which may be performed after step 1436. Step 1436 may be a step of method 1404 (FIG. 14D) and/or may be a step of the additional steps 1406 (of FIG. 14E). Thus, optional steps 1454 may be incorporated into various embodiments of method 1404 and/or into additional steps 1406. FIG. 14G may depict a flow diagram of exemplary steps for generating a personalized recommendation pertaining to the at least one individual which may be triggered by receiving the request for the personalized information of interest. FIG. 14G may depict steps of method 1470.

Now turning back to a more detailed discussion of FIG. 14A. FIG. 14A may depict method 1400. In some embodiments, method 1400 may be a method for generating the personalized information of interest pertaining to at least one individual. In some embodiments, method 1400 may comprise steps: step 1408, step 1434, and step 1427. In some embodiments, step 1408 may comprise receiving a request for the personalized information of interest; wherein the personalized information of interest pertains to the at least one individual. In some embodiments, step 1434 may comprise receiving sequence information of at least one segment 114. In some embodiments, the at least one segment 114 may relate to the request for the personalized information of interest. In some embodiments, step 1427 may comprise presenting pertinent records. In some embodiments, method 1400 may end in a different presenting step, other than step 1427.

Note, a provider (i.e., a requestor) of the request for the personalized information of interest may be the at least one individual, e.g., a patient, or it may be an agent of the at least one individual, or some combination thereof. The agent may be selected from one or more of: physicians, healthcare practitioners, parents, legal guardians, third party provider of genetic study results, an operator of the system and/or the method, and the like of the at least one individual. For example, and without limiting the scope of the present invention, it may be the at least one individual who may be request the personalized information of interest, but it may be the physician, the health care practitioner, and/or the third party provider of genetic study results that may provide requested sequence information (per a step 1434) that may be necessary to further process the request for the personalized information of interest so that the pertinent records that are presented are indeed personalized, at a genetic level, to the at least one individual.

In some embodiments, the personalized information of interest may comprise one or more of: at least one predisposition for developing a given disease; at least one predisposition for developing a given phenotype; at least one personalized healthcare recommendation; and/or genetic research results; such that the requestor (and/or the provider of the request) may be requesting any one or more of these types of personalized information of interest. For example, and without limiting the scope of the present invention, in some embodiments, the request for the personalized information of interest may comprise a request for the at least one personalized healthcare recommendation.

In some embodiments, the at least one personalized healthcare recommendation may be one or more of: a determination specific to the at least one individual's genome of a preferred treatment modality; a determination specific to the at least one individual's genome of a preferred medicine (or medicines); and/or a determination specific to the at least one individual's genome of a preferred dosage regimen.

In some embodiments, the request for the personalized information of interest, with respect to the at least one individual, may comprise one or more of the following: at least some genome sequence 110 and/or at least some associated information 120.

In some embodiments, the at least some genome sequence 110 may be a subset of one or more genome sequences 110. In some embodiments, the at least some genome sequence 110 or the one or more genome sequences 110 may comprise one or more of: sequence-associated-information 112 and/or one or more segments 114.

In some embodiments, the at least some associated information 120 may comprise one or more of: at least some phenotype information 122, at least some medical record information 124, and/or at least some personal information 126. For example, and without limiting the scope of the present invention, the request for the personalized information of interest may comprise at least a disease or a genetic condition of the at least one individual. In some embodiments, this disease of the at least one individual may be communicated in a form of ICD code(s) (international classification of diseases) and/or the like. For example, such ICD code(s) may be component(s) of the at least some medical record information 124. In some exemplary embodiments, the request for the personalized information of interest may comprise at least the disease or the genetic condition of the at least one individual and at least one segment 114 of that at least one individual, relevant to the disease or genetic condition. In some embodiments, the request for the personalized information of interest may also comprise some phenotype information 122 (e.g., weight, race, ethnicity, age, and the like); some personal information 126 (e.g., age, geographic location, and the like); and/or some medical record information 124 (e.g., ICD code, allergies, present medications, medications and/or treatment modalities already tried for the disease, and the like).

In some embodiments, the request for the personalized information of interest, with respect to the at least one individual, may comprise one or more of the following: one or more genome sequences 110 and/or associated information 120; wherein the one or more genome sequences 110 received may be in an anonymized format; and/or wherein at least some of the associated information 120 received may be in an anonymized format.

In some embodiments, method 1400 (FIG. 14A), method 1402 (FIG. 14B), method 1403 (FIG. 14C), method 1404 (FIG. 14D), and/or method 1470 (FIG. 14G) may all end (terminate) in a presenting step. For example, and without limiting the scope of the present invention, both method 1400 (FIG. 14A) and method 1402 (FIG. 14B) may end in presenting step of step 1427, of presenting the pertinent records. Method 1403 (FIG. 14C) may end in presenting step of step 1428, of presenting filtered pertinent records. Method 1404 (FIG. 14C) may end in presenting step of step 1438, of presenting narrowed pertinent records. Step 1458 (of FIG. 14F) may comprise presenting filtered and/or narrowed pertinent records. Step 1484 (of FIG. 14G) may comprise presenting at least one personalized recommendation.

In some embodiments, such presenting steps may comprise one or more of: publishing to a publicly accessible website; publishing to a website accessible by account; printing and mailing a physical copy; publishing to a file (which may be downloadable); publishing a link to the file; publishing a password protected link to the file; emailing the file; emailing information in a body of an email; texting the file; texting the information in a body of a text; and/or uploading the information to one or more medical records 124 of the at least one individual. The information that may be presented may be the pertinent records and/or the personalized information of interest.

In some embodiments, the step of presenting the pertinent records (e.g., step 1427, step 1428, step 1438, and/or step 1458) may comprise one or more of: publishing the pertinent records to a publicly accessible website; publishing the pertinent records to a website accessible by account; printing and mailing a physical copy of the pertinent records; publishing the pertinent records to a file (which may be downloadable); publishing a link to access the file; publishing a password protected link to the file; emailing the file; emailing the pertinent records in a body of an email; texting the file; texting the pertinent records in a body of a text; and/or uploading the pertinent records to one or more medical records 124 of the at least one individual. Differences as between step 1427, step 1428, step 1438, and/or step 1458, may reflect whether or not the pertinent records may have been filtered or not, narrowed or not, or both narrowed and filtered or not.

In some embodiments, the pulled pertinent records (e.g., from step 1424) that may be pertinent to the request for the personalized information of interest may be provided to the provider (requestor) of the request in one of these presentation steps of: step 1427, step 1428, step 1438, and/or step 1458. For example, and without limiting the scope of the present invention, these pulled pertinent records may be printed and/or published; wherein publication may be publicly available and/or available to the provider (requestor). For example, and without limiting the scope of the present invention, these pulled pertinent records may be published to a database (with public access or accessible by the provider), published to a downloadable file (accessible by the provider), published to a website (with public access or accessible by the provider), and/or the like.

In some embodiments, at least some of the pertinent records may be presented in a table. In some embodiments such a table may be an electronic or digital table. At least some of data of the pertinent records in the table may be sortable by the table comprising at least one sortable column header. In some embodiments, this table may comprise one or more of the following table column headers: disease of interest, genetic condition of interest, ages of interest, races of interest, ethnicity of interest, loci of segments 114 examined, recommended medicine or recommended treatment modality, prior treatment results, allergies, other present medications, and/or the like. In some embodiments, at least one of these table column headers may be sortable. In some embodiments, at least some of data of the pertinent records in the table may be filtered. In some embodiments, the at least some of the data in the table may be hyper-linked to expanded information, such as, but not limited to, further details on a particular treatment modality. Note, in some embodiments, filtering and presenting steps may be integrated together.

In some embodiments, substantially simultaneously with one of the presenting steps, or after one of the presenting steps, the method may delete any (or at least some) information of the request for the personalized information of interest that may not be anonymized. Recall such presenting steps may be selected from the group comprising: step 1427, step 1428, step 1438, step 1458, and/or step 1484.

Now turning to a more detailed discussion of FIG. 14B. FIG. 14B may depict method 1402. In some embodiments, method 1402 may be a method for generating personalized information of interest pertaining to at least one individual. In some embodiments, method 1402 may share beginning (i.e., a receiving step) and ending steps (i.e., a presenting step) with method 1400 (of FIG. 14A). For example, both method 1400 and method 1402 may begin with step 1408. For example, both method 1400 and method 1402 may end with step 1427 or other similar presenting step. However, in some embodiments, after step 1408 and before step 1427 (or another presenting step), method 1402 may comprise step 1424. In some embodiments, step 1424 may comprise pulling records pertinent to the request for the personalized information of interest; wherein these records may be the pertinent records.

In some embodiments, step 1424 of pulling the pertinent records may operate by the method (e.g., method 1402, 1404, method 1470, and/or the like) substantially matching at least some of information in the request for the personalized information of interest to similar information already non-transitorily stored in one or more of: one or more storage units 708, the databases, and/or the repositories. That is, pertinent records may be records already non-transitorily stored by the method and/or system, which is why they may be pulled, as in retrieved. Note, use of "substantially" in this paragraph may indicate that a match need not be a perfect match, but rather may be deemed a match if some predetermined similarity may be present, such as, but not limited to, a similarity of 90% or more between the information being compared.

For example, and without limiting the scope of the present invention, one or more storage units 708, the databases, and/or the repositories may non-transitorily store various genetic study results, such as GWAS results and/or other genetic study results (e.g., that may have been received pursuant to one or more methods of the FIG. 13 series of figures). In some embodiments, such one or more storage units 708, databases, and/or repositories may non-transitorily store such genetic study results information as noted in FIG. 1 and in the FIG. 1 discussion, e.g., stored as various original data 101. For example, and without limiting the scope of the present invention, the method (e.g., method 1402, 1404, method 1470, and/or the like) may search one or more of: one or more storage units 708, the databases, and/or the repositories for one or more of: similar diseases, similar genetic conditions, similar weights, similar ages, similar gender, similar race, similar ethnicity, similar allergies, similar present medications, similar family history, similar genetic markers, similar segments, and/or the like. This may be how step 1424 of pulling the pertinent records operates. Also recall, that such original data 101 may be non-transitorily stored in formats dictated in the FIG. 8 series of figures, i.e., non-transitorily stored as various organizational units, that may also be further modified; and that may be accessible by using linkage records 600 and/or anonymized linkage records 1000.

In some embodiments, step 1424 of pulling the pertinent records may operates by the method substantially matching at least some of information in the request for the personalized information of interest to at least some original data 101, such as, but not limited, at least some associated information 120.

In some embodiments, a pertinent record selected from the pertinent records may be deemed pertinent if the pertinent record may comprise at least one segment 114 (e.g., already in storage) that may substantially match one or more of: at least one segment 114 or at least one disease in the request for the personalized information of interest for that at least one individual. In some embodiments, the pertinent record selected from the pertinent records may be deemed pertinent if the pertinent record may also comprise one or more of: similar genetic conditions, similar weights, similar ages, similar gender, similar race, similar ethnicity, similar allergies, similar present medications, similar family history, similar genetic markers, and/or the like that may substantially match such similar information in the request for the personalized information of interest for that at least one individual.

Now turning back to a more detailed discussion of FIG. 14C. FIG. 14C may depict method 1403. In some embodiments, method 1403 may be a method for generating the personalized information of interest pertaining to at least one individual. Method 1403 may be a more detailed embodiment of method 1402. Method 1403 may depict additional steps disposed between step 1408 and step 1424; and may provide for optional filtering step(s) prior to ending the method in the presenting step. These additional steps disposed between step 1408 and step 1424 may be of at least one check, a sufficiency check (e.g., step 1410, step 1412, and step 1414) and/or an anonymity check (e.g., step 1416, step 1418, step 1420, and step 1422). And the optional filtering step, may be step 1426, which may be disposed between step 1424 of pulling the pertinent records and the ending step, a presenting step, of step 1428 of presenting filtered pertinent records.

In some embodiments, either or both checks (i.e., the sufficiency check and the anonymity check) may be incorporated into any method after step 1408 of receiving the request for the personalized information of interest. So either or both of these checks may be incorporated into embodiments of method 1400 (FIG. 14A), 1402 (FIG. 14B), 1404 (FIG. 14D), and/or method 1470 (FIG. 14G).

Similarly, the optional filtering step of step 1426, of filtering the pulled pertinent records to produce filtered pertinent records may be incorporated into any method after step 1424 of pulling the pertinent records, such as, but not limited to, method 1402 (FIG. 14B), method 1404 (FIG. 14D), and method 1470 (FIG. 14G).

In some embodiments, before the pertinent records may be pulled (e.g., via step 1424), the request for the personalized information of interest may be examined for a sufficiency of the request for the personalized information of interest. This may be step 1410. In some embodiments, after receiving the request for the personalized information of interest (e.g., via step 1408), the request for the personalized information of interest may be examined for the sufficiency of the request for the personalized information of interest. This may be step 1410.

In some embodiments, if the request for the personalized information of interest may comprise at least one segment 114 and at least one disease or genetic condition of the at least one individual, then the request for the personalized information of interest may be sufficient.

In some embodiments, if the request for the personalized information of interest may be missing a segment 114 or a disease or a genetic condition of the at least one individual, then the request for the personalized information of interest may be insufficient, and such missing information may be requested via step 1412 of requesting additional information. In some embodiments, the requested additional information may be received via step 1414. Step 1414 may then proceed back to step 1410 to test whether or not the received additional information may be sufficient. See e.g., FIG. 14C. In some embodiments, the missing information (that may be request in step 1412 and received in step 1414) may be tested for sufficiency, via step 1410, using same criteria as applied to the request for the personalized information of interest.

If the sufficiency check of step 1410 may be met, then the method may progress, such as to progressing to step 1416 of the anonymity check or progressing to step 1424 of pulling the pertinent records.

In some embodiments, before step 1424 of pulling the pertinent records and in some embodiments, after successfully examining the request for the personalized information of interest for sufficiency per step 1410, the request for the personalized information of interest may be examined for anonymity of the request for the personalized information of interest. This anonymity check may be step 1416. In some embodiments, after receiving the request for the personalized information of interest (e.g., via step 1408), the request for the personalized information of interest may be examined for anonymity of the request for the personalized information of interest. This anonymity check may be step 1416.

If the request for the personalized information of interest may comprise at least one anonymized-segment 114, then the request for the personalized information of interest may be anonymized. Note, in some embodiments, step 1416 of checking for anonymity of the request for the personalized information of interest may be optional.

In some embodiments, if the request for the personalized information of interest may be missing the at least one anonymized-segment 114 of the at least one individual, then the method may either: anonymize at least some of the information in the request already received, via step 1422 (e.g., the at least one segment 114 from the request for the personalized information of interest may be anonymized); or the method may request for at least one anonymized-segment relevant to a disease or a genetic condition of the least one individual be transmitted, as in step 1418; wherein this requesting step of step 1418, may be followed by a receiving step of step 1420. See e.g., FIG. 14C. Step 1420 may comprise receiving the request for the at least one anonymized-segment. Once this additional request may be received, step 1420 may feed back into step 1416 of the anonymity check; wherein this additional request may be tested for anonymity. See e.g., FIG. 14C. Same criteria as applied to the request for the personalized information of interest tested in step 1416 may be applied to the additional received request of step 1420. Once the anonymity check step of step 1416 may be successfully passed, the method may progress to pulling the pertinent records of step 1424.

In some embodiments, before step 1428 of presenting the pertinent records, the method may comprise a step of filtering the pertinent records. This may be step 1426. See e.g., FIG. 14C. In some embodiments, step 1426 of filtering the pertinent records may be optional.

In some embodiments, the pulled pertinent records may be filtered before presenting. See e.g., step 1426. In some embodiments, any filtering or a portion thereof may be automated. In some embodiments, any filtering (or at least some filtering) may be done manually by staff of the method and/or system. In some embodiments, any filtering (or at least some filtering) may be done manually by the at least one individual and/or their agent(s) (i.e., by the requestor or the provider of the request for the personalized information of interest).

In some embodiments, a need for some filtering after pulling the pertinent records may be mitigated and/or reduced by requiring certain information in the request for the personalized information of interest. This may be accomplished by questionnaires and/or online forms for receiving the request for the personalized information of interest, or for requests for missing information (e.g., step 1412 and/or step 1418). In some embodiments, receipt of this certain information may result in more specific pertinent records being pulled, as compared with embodiments wherein some filtering may occur after pulling the pertinent records.

In some embodiments, step 1426 of filtering the pertinent records may comprise filtering according to one or more of: similar diseases, similar genetic conditions, similar weights, similar ages, similar gender, similar race, similar ethnicity, similar allergies, similar present medications, similar family history, similar genetic markers, or similar segments, with respect to similar information in the request for the personalized information of interest. In some embodiments, the step of filtering the pertinent records may be accomplished by filtering any of associated information 120 that may have been pulled in step 1424.

In some embodiments, step 1426 of filtering the pertinent records may be a step of analysis of the pertinent records, wherein the step of analysis reduces the pertinent records down to a summary of pertinent information. In some embodiments, wherein the system and/or the method may pull three or more pertinent records, such pulled pertinent records may be analyzed to produce the summary of pertinent information. In some embodiments, that analysis may be automated, manual, or combinations thereof. In some embodiments, that analysis may at least involve some statistical analysis.

In some embodiments, the summary of pertinent information may comprise one or more of: at least one recommended medicine or at least one recommended treatment modality for a given segment 114 and a given disease or a given genetic condition; at least one predisposition for developing the given disease; and/or at least one predisposition for developing a given phenotype. In some embodiments, the summary of pertinent information may also comprise presenting the at least one recommended medicine or the at least one recommended treatment modality with a given age (or age range), a given race (or races), a given ethnicity (or ethnicities), a given gender, a given weight (or weight range), a given allergy (or allergies), a given present medication, and/or the like. Note, in some embodiments, filtering and presenting steps may be integrated together.

Now turning back to a more detailed discussion of FIG. 14D. FIG. 14D may depict method 1404. In some embodiments, method 1404 may be a method for generating the personalized information of interest pertaining to at least one individual. Method 1404 may be a combination of method 1400 and method 1402, as well as some additional steps to facilitate integration of method 1400 with method 1402. In some embodiments, method 1404 may comprise steps: step 1408 (the initial receiving step), step 1424, step 1430, step 1432, step 1434, step 1436, and step 1438 (the terminating presenting step). Note, step 1408 of receiving the request for the personalized information of interest has been discussed. And step 1424 of pulling the pertinent records has been discussed.

In some embodiments, after step 1424 of pulling the pertinent records, the method may comprise a step of identifying at least one segment 114 that may be pertinent to the pertinent records. This may be step 1430 in method 1403 of FIG. 14D. For example, and without limiting the scope of the present information, segments 114 which may associate with a given disease or a given genetic condition at some predetermined frequency may be pertinent to the pertinent records; where the given disease or the given genetic condition may have been included in the request for the personalized information of interest. Note, in identifying the at least one segment 114 that may be pertinent to the pertinent records, method and/or system embodiments of the present invention may utilize (already non-transitorily stored) cataloged-results-information that may have been cataloged pursuant to the method and/or system embodiments operating per one of the FIG. 13 methods.

In some embodiments, the at least one segment 114 may comprise genetic location information pertinent to the disease or the genetic condition of the at least one individual; wherein this disease or this genetic condition may be included in the request for the personalized information of interest. In some embodiments, the at least one segment 114 may comprise length information such as a number of nucleotides and genetic location information relevant to the disease or the genetic condition of the at least one individual; wherein this disease or this genetic condition may be included in the request for the personalized information of interest.

In some embodiments, the method may comprise a step of requesting sequence information of the at least one individual pertaining to the at least one segment 114 identified in step 1430. This requesting step may be step 1432 of method 1404 of FIG. 14D. That is, in some embodiments, the at least one individual (or their agent) (who may have provided the request for the personalized information of interest) may then need to provide sequence information of that individual's own segment(s) 114 that may match the location information and/or length information of the at least one segment 114 identified in step 1430. In some embodiments, the method may comprise a step of receiving the sequence information requested in step 1432. This may be step 1434 of method 1404 of FIG. 14D.

In some embodiments, the method may comprise a step of narrowing the pertinent records to narrowed pertinent records by using the sequence information received in step 1434. This may be step 1436 of method 1404 of FIG. 14D. In some embodiments, this narrowing step 1436 may involve deleting less pertinent records from an existing pool of the pertinent records. In some embodiments, this narrowing step 1436 may involve creating a pool of narrowed pertinent records from the pool of pertinent records. For example, and without limiting the scope of the present invention, pertinent records may be eliminated if such records may not have an associated segment 114 that may be similar to the sequence information provided by the at least one individual in step 1434. Conversely, in some embodiments, the narrowed pertinent records may comprise associated segments 114 that may be similar to the sequence information provided by the at least one individual in step 1434.

In some embodiments, method 1404 after step 1436 may conclude with the presenting step. In some embodiments, this presenting step may be step 1438 of presenting the narrowed pertinent records.

Note, in some embodiments of method 1404, such a terminating presenting step, as in step 1438, may be preceded or integrated with a filtering step, such as step 1426.

Note, in some embodiments of method 1404, step 1408 of receiving the request for the personalized information of interest may be followed by either or both of the checks of method 1403, i.e., of the sufficiency check 1410 and/or of the anonymity check 1416.

Now turning back to a more detailed discussion of FIG. 14E. FIG. 14E may depict additional steps 1406, which may comprise a series of steps after step 1434 but before an ending presenting step. These additional steps 1406, in some embodiments, may be integrated into method 1400 (FIG. 14A) and/or integrated into method 1404 (FIG. 14D), as both methods include step 1434. FIG. 14E may depict two checks, a sufficiency check and an anonymity check, which may be similar to the checks depicted in FIG. 14C, except in FIG. 14E these checks may be carried after step 1434 of receiving the sequence information pertinent to the at least one segment identified in step 1430. Additionally, the checks in FIG. 14E may be operating upon different information that the checks in method 1403 of FIG. 14C.

In some embodiments, after receiving the sequence information of step 1434, the method (e.g., an embodiment of method 1404 of FIG. 14D or an embodiment of method 1400 of FIG. 14A) may comprise a step of checking that sequence information for sufficiency. This sufficiency check may be step 1440 of FIG. 14E.

In some embodiments, if this sequence information of step 1434 may comprise information that may be similar to the at least one segment 114 identified in step 1430, by at least some predetermined threshold, then the sequence information received in step 1434 may be sufficient and the method may then proceed to either step 1436 or to the anonymity check of step 1446.

In some embodiments, if this sequence information of step 1434 may match a location of the at least one segment 114 identified in step 1430, by at least some predetermined threshold, then the sequence information received in step 1434 may be sufficient and the method may then proceed to either step 1436 or to the anonymity check of step 1446.

In some embodiments, if this sequence information of step 1434 may not match a location of the at least one segment 114 identified in step 1430, by the at least some predetermined threshold, then this sequence information received in step 1434 may be insufficient; and then method may request additional sequence information. Such requesting of the additional sequence information may be step 1442 of FIG. 14E. Step 1442 may lead into step 1444 of receiving the requested additional sequence information. See FIG. 14E. Upon receiving the additional sequence information, the method may proceed back to the sufficiency check step of step 1440 to examine the sufficiency of the received additional sequence information. In some embodiments, the additional sequence information (that may have requested in step 1442 and received in step 1444) may be tested for sufficiency using same criteria as applied to the sequence information received in step 1434.

In some embodiments, once the sufficiency check step of step 1440 may be successfully completed (i.e., a determination that either the sequence information or the additional sequence information may be sufficient), the method may then proceed to either step 1436 or to the anonymity check of step 1446.

In some embodiments, after receiving the sequence information of step 1434, the method may comprise a step of checking that sequence information for anonymity. This may be step 1446 of FIG. 14E.

In some embodiments, if the sequence information received in step 1434 may comprise information that permits identification of the at least one individual then that sequence information may not be anonymous. In some embodiments, if an identity of the at least one individual cannot be determined from the sequence information received in step 1434, then that sequence information may be anonymous. Note, in some embodiments, checking for anonymity of the sequence information received in step 1434 may be optional. That is, step 1446 may be optional in some embodiments.

In some embodiments, if the sequence information received in step 1434 may be deemed anonymous per step 1446, then the method may proceed with step 1436. See e.g., FIG. 14E. Note, what additional steps step 1436 may lead to may be depicted in FIG. 14D (e.g., step 1438) and/or in FIG. 14F (e.g., FIG. 1456). However, in alternative embodiments, the anonymity check of step 1446 may occur before the sufficiency check of step 1440, in such embodiments, upon successful completion of step 1446 (i.e. of finding the sequence information received in step 1434 may be anonymous), a given method may then proceed to step 1440. This embodiment may not be depicted in the FIG. 14 series of figures.

In some embodiments, if the sequence information received in step 1434 may be deemed not anonymous per step 1446, then the method may proceed down one of two different options. See FIG. 14E. One option may be for the method to proceed to step 1448, then to step 1450, and back to step 1446. Whereas, the other option may be for the method to proceed to step 1452 and then back to step 1446.

In some embodiments, step 1448 may comprise requesting anonymized-sequence-information. This request may be directed to the at least one individual and/or their agent(s). This request of step 1448 may be made electronically, for example, by text, email, phone call, fax, publishing to a website and/or the like. Or this request of step 1448 may be made by mailing the request.

In some embodiments, step 1450 may comprise receiving this requested anonymized-sequence-information. An exemplary step 1450 may involve receiving this requested anonymized-sequence-information via an electronic means. Upon receiving the anonymized-sequence-information of step 1450, step 1450 may proceed back to step 1446, wherein the anonymized-sequence-information may be examined for its anonymity. In some embodiments, the anonymized-sequence-information (that may have requested in step 1448 and received in step 1450) may be tested for anonymity using same criteria as applied to the sequence information received in step 1434.

In some embodiments, once the anonymity check step of step 1446 may be successfully completed (i.e., a determination that either the sequence information or the anonymized-sequence-information may be anonymous), the method may then proceed to step 1436 (or to the sufficiency check of step 1440, in some embodiments).

Regarding the other option of the method proceeding via step 1452 and then back to step 1446, in some embodiments, the method may proceed via step 1452 of anonymizing the sequence information received in step 1434 into anonymized-sequence-information. See step 1452 of FIG. 14E. Anonymizing mechanics and options of such sequence information has been addressed above. For example, and without limiting the scope of the present invention, in some embodiments, step 1452 of anonymizing the sequence information may comprise one or more of: deleting, inserting, appending, and/or replacing one or more nucleotides in the sequence information such that the resulting anonymized-sequence-information may not reveal the identity of the at least one individual. Once anonymized per step 1452, step 1452 may proceed back to step 1446, wherein the resulting anonymized-sequence-information may be examined for anonymity via step 1446.

Note, anonymizing option of step 1448 and step 1450 may place an anonymization burden upon the at least one individual and/or their agent(s); whereas, under step 1452, this anonymization burden may be upon the method and/or the system.

In any event, upon successfully completing step 1440 and/or successfully completing step 1446, step 1436 may ensue. See e.g., FIG. 14E. Recall step 1436 may comprise the step of narrowing the pertinent records to narrowed pertinent records by using the anonymized-sequence-information (or by using the sequence information).

Now turning to a more detailed discussion of FIG. 14F. FIG. 14F may depict optional steps 1454. Optional steps 1454 may comprise some additional steps which may be performed after step 1436. Step 1436 may be a step of method 1404 (FIG. 14D) and/or may be a step of the additional steps 1406 (of FIG. 14E). Thus, optional steps 1454 may be incorporated into various embodiments of method 1404 and/or into additional steps 1406. In some embodiments, optional steps 1454 may comprise steps: step 1436, step 1456, and step 1458.

In some embodiments, step 1456 may comprise a step of filtering the narrowed pertinent records. Step 1456 may be similar to step 1426 of filtering the pertinent records. In some embodiments, step 1456 of filtering the narrowed pertinent records may be optional.

In some embodiments, the pulled and narrowed pertinent records may be filtered before presenting. See e.g., step 1456 of FIG. 14F. In some embodiments, any filtering or a portion thereof may be automated. In some embodiments, any filtering (or at least some filtering) may be done manually by staff of the method and/or system. In some embodiments, any filtering (or at least some filtering) may be done manually by the at least one individual and/or their agent(s) (i.e., by the requestor or the provider of the request for the personalized information of interest).

In some embodiments, a need for some filtering after pulling and narrowing the pertinent records may be mitigated and/or reduced by requiring certain information in the request for the personalized information of interest. This may be accomplished by questionnaires and/or online forms for receiving the request for the personalized information of interest, or for requests for missing information (e.g., step 1412, step 1418, step 1442, and/or step 1448). In some embodiments, receipt of this certain information may result in more specific pertinent records being pulled, as compared with embodiments wherein some filtering may occur after pulling the pertinent records.

In some embodiments, step 1456 of filtering the pertinent records may comprise filtering according to one or more of: similar diseases, similar genetic conditions, similar weights, similar ages, similar gender, similar race, similar ethnicity, similar allergies, similar present medications, similar family history, similar genetic markers, or similar segments, with respect to similar information in the request for the personalized information of interest. In some embodiments, the step of filtering the narrowed pertinent records may be accomplished by filtering any of associated information 120 that may have been pulled in step 1424.

In some embodiments, step 1456 of filtering the narrowed pertinent records may be a step of analysis of the narrowed pertinent records, wherein the step of analysis reduces the narrowed pertinent records down to a summary of pertinent information. In some embodiments, wherein the system and/or the method may pull three or more pertinent records, such pulled pertinent records may be analyzed to produce the summary of pertinent information. In some embodiments, that analysis may be automated, manual, or combinations thereof. In some embodiments, that analysis may at least involve some statistical analysis.

In some embodiments, the summary of pertinent information may comprise one or more of: at least one recommended medicine or at least one recommended treatment modality for a given segment 114 and a given disease or a given genetic condition; at least one predisposition for developing the given disease; and/or at least one predisposition for developing a given phenotype. In some embodiments, the summary of pertinent information may also comprise presenting the at least one recommended medicine or the at least one recommended treatment modality with a given age (or age range), a given race (or races), a given ethnicity (or ethnicities), a given gender, a given weight (or weight range), a given allergy (or allergies), a given present medication, and/or the like. Note, in some embodiments, filtering and presenting steps may be integrated together.

In some embodiments, after the filter step of step 1456, the method may progress to the presenting step of step 1458. See FIG. 14F. In some embodiments, step 1458 may comprise presenting the filtered and/or narrowed pertinent records. Note, in some embodiments, the requestor (e.g., the at least one individual and/or their agent(s)) upon reviewing what may be presented via step 1458, may desire and/or require additional filtering. Various embodiments may permit such additional filtering, in that step 1458 may progress back to the filtering step of 1456, which may then proceed to the presenting step of step 1458. See e.g., FIG. 14F. In some embodiments, the method may permit different profiles of filtering to be saved simultaneously, such that the requestor (e.g., the at least one individual and/or their agent(s)) may utilize such different filtering profiles to present different filtered and narrowed pertinent record in step 1458 according to different needs of the requestor.

Now turning back to a more detailed discussion of FIG. 14G. FIG. 14G may depict method 1470. Method 1470 may comprise exemplary steps for generating a personalized recommendation pertaining to the at least one individual which may be triggered by receiving the request for the personalized information of interest. In some embodiments, method 1470 may comprise steps of: step 1408, step 1424, step 1472, step 1474, step 1476, step 1432, step 1434, step 1482, and step 1484. In some embodiments, at least some aspects of some of these steps have previously been discussed, such as for step 1408, step 1424, step 1432, step 1434, and the presenting step of step 1484.

In some embodiments, the request for the personalized information received in step 1408 may comprise a disease of interest. In some embodiments, after step 1408 of receiving the request for the personalized information of interest pertaining to the at least one individual, the method may request the disease of interest, if the disease of interest was not included in the request for the personalized information. In some embodiments, the method may receive the disease of interest. In some embodiments, these two steps of requesting the disease of interest and of receiving the disease of interest may be sub-steps of step 1408.

In some embodiments, step 1424 of pulling the pertinent records may operate by the method substantially matching the disease of interest to at least some associated information 120 non-transitorily stored in one or more of: one or more storage units 708, the database, and/or the repositories.

In some embodiments, step 1424 of pulling the pertinent records may comprise a step of presenting these pertinent records that were pulled. Such presenting may be in preparation of step 1472, i.e., such a presenting step may not be a final presenting step (i.e., an ending or a terminating step). Rather this presenting step may be intermediate and/or temporary.

In some embodiments, after the step of pulling and presenting the pertinent records (e.g., as in step 1424), the method may comprise a step of receiving a selection for one or more of the pertinent records that were presented. This receiving selection step may be step 1472 of method 1470 of FIG. 14G.

In some embodiments, after step 1472, the method may proceed to step 1432 of requesting the sequence information; or the method may alternatively proceed down an optional filtering route via step 1474. See FIG. 14G.

In some embodiments, after step 1472 of receiving the selection, the method may receive a command to filter the one or more pertinent records selected in step 1472, resulting in narrowed and/or filtered of the one or more pertinent records selected in step 1472. This may be step 1474 of method 1470 of FIG. 14G.

In some embodiments, the method may receive and/or utilize at least some associated information 120 that may aid in filtering the one or more pertinent records selected in step 1472. This may be step 1476 of method 1470 of FIG. 14G.

Note, in some embodiments, step 1474 and step 1476 may be optional. In some embodiments step 1472 may proceed to step 1432. In some applications of method 1470, when in step 1472 only one pertinent record may be received as the selection, then no further filtering may be necessary, and step 1472 may proceed to step 1432.

In some embodiments and/or in some applications, where filtering and/or additional filtering may be desired and/or necessary, step 1474 or step 1474 with step 1476, may proceed back to step 1472, in which one or more of the pulled and now filtered pertinent records may be selected. See FIG. 14G.

In some embodiments, the method may comprise a step of identifying at least one segment 114 that may be pertinent to the one or more pertinent records that were selected (e.g., selected via step 1472). In some embodiments, this identifying step may be disposed between step 1472 and step 1432. In some embodiments, this identifying step may lead into step 1432. In some embodiments, this identifying step may be substantially similar to step 1430 of FIG. 14D. In some embodiments, the method may comprise the step of requesting the sequence information that may pertain to the at least one segment 114 that was identified. In some embodiments, this may be step 1432. See FIG. 14G. In some embodiments, the method may receive this sequence information. In some embodiments, this may be step 1434. See FIG. 14G.

In some embodiments, the method may retrieve at least one personalized recommendation from one or more of: one or more storage units 708, the databases, and/or the repositories. In some embodiments, this may be step 1482. See FIG. 14G. In terms of mechanics, step 1482 may function substantially similarly to step 1436, in some embodiments. In some embodiments, the at least one personalized recommendation may be associated with the sequence information received in step 1434. In some embodiments, this sequence information received in step 1434 may be used as a basis for the retrieving. In some embodiments, the at least one personalized recommendation may be associated with the sequence information and may also be associated with a given disease and/or a given genetic condition.

In some embodiments, the at least one personalized recommendation may comprise one or more of: at least one predisposition for developing the given disease; at least one pre-disposition for developing the given phenotype; and/or at least one personalized healthcare recommendation.

In some embodiments, the at least one personalized healthcare recommendation may be one or more of: a determination specific to the at least one individual's genome of a preferred treatment modality; a determination specific to the at least one individual's genome of a preferred medicine; and/or a determination specific to the at least one individual's genome of a preferred dosage regimen.

In some embodiments, sufficiency checks may occur after step 1434 of method 1470, such as steps similar to step 1440, step 1442, and step 1444 shown in FIG. 14E. In some embodiments, anonymity checks may occur after step 1434 of method 1470, such as steps similar to step 1446, step 1448 (and step 1450) or step 1452, shown in FIG. 14E.

In some embodiments, the method may then present the at least one personalized recommendation. In some embodiments, this may be step 1484 of method 1470. See FIG. 14G.

Note, the various requests discussed in the FIG. 12 series of figures methods and/or in the FIG. 14 series of figures methods may be from an application running on a computing device, which may be a computer system as discussed in the FIG. 7 figure discussion and as depicted in the FIG. 7 figure. In some embodiments, these requests may be made through a website being hosted upon a computer system as discussed in the FIG. 7 figure discussion and as depicted in the FIG. 7 figure. In some embodiments, these requests may be received at a computer system as discussed in the FIG. 7 figure discussion and as depicted in the FIG. 7 figure. In some embodiments, the various receiving and/or requesting steps may be carried out on a computer system as discussed in the FIG. 7 figure discussion and as depicted in the FIG. 7 figure. In some embodiments, these requests received at the computer system may be through offline submission and/or through third-party submission. In one embodiment, these requests may be submitted by an individual, such as the at least one individual noted in some of the FIG. 14 series discussion. In another embodiment, these requests may be submitted by a healthcare provider, e.g., of the at least one individual. In yet another embodiment, these requests may be submitted by a third-party service. In some embodiments, any of: original data 101, including modifications; linkage records 600; anonymized linkage records 1000; anonymized information; the genetic study results; the pertinent records, the at least one personalized recommendation; and/or the like may be non-transitorily stored in one or more of: one or more storage units 708, the databases, and/or the repositories. In one example, at least some of the: one or more storage units 708, the databases, and/or the repositories may be owned and/or controlled by the at least one individual and/or their agent(s).

FIG. 15 may show examples of communicating with system(s) that may process and store the genome sequence(s) 110 and at least some of their associated information 120 in accordance with one or more embodiments of the present invention. Alternatively, or in conjunction, FIG. 15 may depict various operating environments for various computing systems 700 and/or systems; wherein one or more storage units 708 of the one or more computing systems 700 may non-transitorily store codes executable by one or more processing units 702; wherein such codes may be implementing any one or more method and/or steps discussed herein and in the accompanying figures. Such systems may comprise one or more computer systems 700.

In FIG. 15, nucleotide sequence information 1502 may be generated from one or more nucleotide sequencing devices. Such nucleotide sequence information 1502 may be of at least some of one or more genome sequences 110. In some embodiments, this at least some of one or more genome sequences 110 may comprise, but not be limited to, at least some: sequence-associated-information 112 and/or one or more segments 114. Such nucleotide sequencing devices may be implemented as one or more computer systems 700.

In one embodiment, such generated nucleotide sequence information 1502 may be non-transitorily stored in non-transitory computer-readable medium (e.g., memory) of a computing device such as, but not limited to: a mobile phone, a smart phone, a wearable, a desktop, a server, a laptop, and/or a tablet computing device; collectively or individually assigned reference numeral 1504 in FIG. 15. That is, in some embodiments, reference numeral 1504 may be assigned to one or more computing devices 1504, wherein computing device 1504 may be selected from the group comprising one or more of: mobile phones, smart phones, wearables, desktops, servers, laptops, and/or tablet computing devices. That is, in some embodiments, at least some of one or more computing devices 1504 may be mobile computing devices such as, but not limited to: the mobile phones, the smart phones, the wearables, the laptops, and/or the tablet computing devices. In some embodiments, one or more computing devices 1504 may have the architecture and/or configuration of a given computing system 700.

In another embodiment, such generated nucleotide sequence information 1502 may be non-transitorily stored in non-transitory computer-readable medium (e.g., memory) of a storage device that may be connected, via communication pathway 1506, to one or more computing devices 1504. In some embodiments, communication pathway 1506 may be a direct communication pathway between the storage device non-transitorily storing nucleotide sequence information 1502 and one or more computing devices 1504. In some embodiments, communication pathway 1506 may be one or more of a wired connection and/or a wireless connection.

Alternatively, or in addition to (e.g., as in a redundancy or a backup) communication pathway 1506 may be replaced (or augmented) with an indirection communication pathway utilizing communication pathway 1514, network 1508, and communication pathway 1512. See FIG. 15. In some embodiments, network 1508 may comprise one or more of: the internet, a wide area network (WAN), and/or a local area network (LAN). In some embodiments, communication pathways 1506, 1514, 1512, 1510, and/or 1516 may be wired and/or wireless connections.

As shown in FIG. 15, various system embodiments of the present invention may be configured in a client-server configuration and/or in a cloud based computing configuration. For example, and without limiting the scope of the present invention, the requestors (i.e., the providers, submitters, and/or the at least one individual or their agent(s)) may have client software on their one or more computing device 1504, which may interact with server software running on one or more storage units 708 (and/or memory unit of processing unit 702) of the one or more computing systems 700, wherein the one or more computing systems 700 may be one or more servers. Such a client-server configuration may permit implementation of each and every method and/or step disclosed herein. Communication in such a client-server configuration between any given client and any given server may be via communication pathway 1514, network 1508, and communication pathway 1516. For example, and without limiting the scope of the present invention, various requests (see e.g., the FIG. 12 series of figures and its corresponding discussion; as well as the FIG. 14 series of figures and its corresponding discussion) and/or any other necessary input information may be sent from such clients wherein such various requests and/or the any other necessary input information may be received by the server(s). For example, and without limiting the scope of the present invention, various genetic study results (see e.g., the FIG. 13 series of figures and its corresponding discussion) and/or any other necessary input information may be sent from such clients wherein such genetic study results and/or the any other necessary input information may be received by the server(s). Such clients may download and non-transitorily store their appropriate client software from such servers.

Similarly, in the cloud configuration, these servers may serve various web-based applications, such that one or more computing devices 1504 need not have any specific nor particularized client software, apart from a web browser to access these various web-based applications being served by such servers. Similarly, such a cloud configuration may permit implementation of each and every method and/or step disclosed herein. For example, and without limiting the scope of the present invention, various requests (see e.g., the FIG. 12 series of figures and its corresponding discussion; as well as the FIG. 14 series of figures and its corresponding discussion) and/or any other necessary input information may be sent from such one or more computing devices 1504 (and/or generated in the web-based application) wherein such various requests and/or the any other necessary input information may be received by the server(s). For example, and without limiting the scope of the present invention, various genetic study results (see e.g., the FIG. 13 series of figures and its corresponding discussion) and/or any other necessary input information may be sent from such one or more computing devices 1504 wherein such genetic study results and/or the any other necessary input information may be received by the server(s).

In some embodiments, nucleotide sequence information 1502 may reside on one or more computing devices 1504, as noted above; however, in other embodiments, nucleotide sequence information 1502 may reside in one or more repositories and/or databases. In some scenarios, such one or more repositories and/or databases may be owned and/or operated (managed) by third parties with respect to owners, operators, managers, and/or licenses of various embodiments of the present invention. In some scenarios, such one or more repositories and/or databases may be owned and/or operated (managed) by the owners, operators, managers, and/or licenses of various embodiments of the present invention. In either scenario, communication between such one or more repositories and/or databases may utilize direct communication pathway 1510 to one or more computing systems 700 (e.g., servers). In either scenario, communication between such one or more repositories and/or databases may utilize indirect communication pathway 1512, network 1508, and communication pathway 1516 to one or more computing systems 700 (e.g., servers).

In some embodiments, at least some of any of the information and/or data discussed herein may be non-transitorily stored in one or more storage units 708 (and/or in the memory unit of a given processing unit 702) of one or more computing systems 700. For example, and without limiting the scope of the present invention, at least some of one or more genome sequences 110 and at least some of associated information 120 may be non-transitorily stored in one or more storage units 708 (and/or in the memory unit of a given processing unit 702) of one or more computing systems 700. Formats of such non-transitory storage, may make use of the organizational units (e.g., segments 114), linkage records 600, anonymized linkage records 1000, and/or including anonymized and/or modified versions.

Some system embodiments of the present invention may comprise one or more computing systems 700. In some such system embodiments, such one or more computing systems 700 may comprise the code, which upon execution per processing units 702, may perform at least some of the steps of any method disclosed herein. Such code may be non-transitorily stored in one or more storage units 708 (and/or in the memory unit of a given processing unit 702). In the client-server configuration, in some embodiments, system embodiments of the present invention may further comprise at least some such of this code that may be non-transitorily stored in memory of one or more computing devices 1504.

For example, in FIG. 15, in one embodiment, the generated nucleotide sequence information 1502 may be submitted into system 700, such that system 700 may receive this the generated nucleotide sequence information 1502; wherein this generated nucleotide sequence information 1502 may be segmented 400 into segments 114 and a linkage record 600 (and/or anonymized linkage record 1000) may be created to non-transitory store such segments 114. See also the FIG. 8 series of figures and its corresponding discussion, as well as FIG. 6; and the FIG. 4 series of figures and the FIG. 5 series of figures, as well as their corresponding discussions.

For example, in FIG. 15, in another embodiment, the previously submitted genome sequence may be opted-out from the system 700 wherein an anonymized linkage record 1000 may be created from the linkage record 600 and at least one segment 114 of the previous submitted genome sequence may be retained in the system 700. In one example, this retained segment 114 may be modified (anonymized). See also the FIG. 11 series of figures and its corresponding discussion, as well as FIG. 10.

For example, in FIG. 15, in another embodiment, the request for genetic study results, such as, but not limited to, GWAS results may be received to system 700; wherein a set of anonymized information (e.g., with the relevant segments 114) may be generated and/or provided by system 700. See also the FIG. 12 series of figures and its corresponding discussion.

For example, in FIG. 15, in another embodiment, the genetic study results may be received into system 700; wherein such received genetic study results may be cataloged and/or associated as non-transitorily stored system 700. See also the FIG. 13 series of figures and its corresponding discussion.

For example, in FIG. 15, in another embodiment, the request for the personalized information of interest may be received into system 700; wherein system 700 may receive the sequence information pertinent to the at least one segment 114, such that this received sequence information may be analyzed in order to provide a required info created by the instruction from the personalized information of interest that may be personalized with respect to this received sequence information. See also the FIG. 14 series of figures and its corresponding discussion.

While the invention has been described with respect to a limited number of embodiments, those skilled in the art, having benefit of this disclosure, will appreciate that other embodiments may be devised which clearly do not depart from the scope of this present invention as disclosed herein. Accordingly, the scope of this present invention must only be limited by the attached claims.

Methods and systems for anonymizing genome segments, genome sequences, and associated information have been described. The foregoing description of the various exemplary embodiments of the invention has been presented for the purposes of illustration and disclosure. It is not intended to be exhaustive nor to limit the invention to the precise form disclosed. Many modifications and variations are possible in light of the above teaching without departing from the disclosed scope of the invention.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

(b) generating one or more referring segments for each anchor segment assigned in the step (a), wherein a given referring segment selected from the one or more referring segments is one or more variations between the anchor segment that is associated with the given referring segment and the pool of genome nucleotide segments, such that by using the one or more referring segments and the anchor segment that is associated with the one or more referring segments, full sequence information of the pool of genome nucleotide segments is known; and (c) non-transitorily storing the one or more anchor segments and the one or more referring segments in one or more storage units, which saves storage space as compared to storing full sequence information of the pool of genome nucleotide segments.

2. The method according to claim 1, wherein the pool of genome nucleotide segments comprises two or more genome samples, wherein prior to the step (a) of assigning

What is claimed is:

1. A method for using one or more anchor segments for a purpose of minimizing storage space, wherein the method comprises the steps of:

(a) assigning the one or more anchor segments from a pool of genome nucleotide segments by using the pool of genome nucleotide segments as a basis for one or more of generating, deriving, computing, calculating, or determining the one or more anchor segments;

the one or more anchor segments, the method comprises a step of receiving the two or more genome samples, wherein each genome sample selected from the two or more genome samples is associated with a different individual.

3. The method according to claim 1, wherein the pool of genome nucleotide segments is non-transitorily stored in one or more of: the one or more storage units, at least one database or at least one repository.

4. The method according to claim 1, wherein the pool of genome nucleotide segments is selected from: whole genome sequences, partial genome sequences, or segments.

5. The method according to claim 1, wherein the pool of genome nucleotide segments comprises two or more genome samples, wherein the two or more genome samples are each from a different individual.

6. The method according to claim 5, wherein each of the two or more genome samples share at least one locus, such that the two more genome samples are alignable for a purpose of identifying the one or more variations.

7. The method according to claim 5, wherein each of the two or more genome samples share at least one locus with a given anchor segment selected from the one or more anchor segments, such that the two more genome samples are alignable with the given anchor segment for a purpose of identifying the one or more variations.

8. The method according to claim 1, wherein the one or more variations are selected from one or more of: an insertion, a deletion, or a replacement of one or more nucleotides as between a given anchor segment selected from the one or more anchor segments and the pool of genome nucleotide segments.

9. The method according to claim 1, wherein the one or more variations comprises one or more polymorphisms as between a given anchor segment selected from the one or more anchor segments and the pool of genome nucleotide segments.

10. The method according to claim 1, wherein the pool of genome nucleotide segments comprises two or more genome samples, wherein the one or more anchor segments is used as a basis for aligning the two or more genome samples for the purposes of identifying the one or more variations.

11. The method according to claim 1, wherein the one or more variations used to generate the given referring segment is anonymized to minimize identification of an individual associated with the given referring segment.

12. The method according to claim 11, wherein the anonymization is accomplished by modifying the one or more variations.

13. The method according to claim 12, wherein the modifying is selected from one or more of: inserting, deleting, or replacing of one or more nucleotides associated with the one or more variations.

14. The method according to claim 11, wherein a record of the anonymization is non-transitorily stored in the one or more storage units or other storage unit.

15. The method according to claim 1, wherein prior to the step (a) of assigning the one or more anchor segments, the method further comprises subdividing the pool of genome nucleotide segments into two or more groups of segments.

16. The method according to claim 15, wherein then the step (a) of assigning the one or more anchor segments, proceeds by assigning an anchor segment for each of the two or more groups of segments, resulting in multiple anchor segments, with one such multiple anchor segment per each of two or more groups of segments.

17. The method according to claim 16, wherein the step (b) of generating the one or more referring segments, proceeds by generating a referring segment for each segment of the two or more groups of segments that is not also one of the multiple anchor segments.

18. The method according to claim 17, wherein each multiple anchor segment selected from the multiple anchor segments is non-transitorily stored in a different repository.

19. The method according to claim 18, wherein each referring segment is non-transitorily stored in the different repository that includes the multiple anchor segment used to generate that referring segment.

20. The method according to claim 15, wherein the pool of genome nucleotide segments comprises two or more genome samples, wherein the step of subdividing the pool of genome nucleotide segments into the two or more groups of segments, is done by grouping the two or more genome samples on a basis of commonality.

* * * * *